United States Patent
Weiss et al.

(10) Patent No.: US 6,835,699 B2
(45) Date of Patent: Dec. 28, 2004

(54) BICYCLE LACTONES, PERFUMERY USES THEREOF, PROCESSES FOR PREPARING SAME AND INTERMEDIATES THEREFOR

(75) Inventors: Richard A. Weiss, Livingston, NJ (US); Mark A. Sprecker, Sea Bright, NJ (US); Marie R. Hanna, Hazlet, NJ (US); Charles E. J. Beck, Summit, NJ (US); Harold W. Jackson, Hazlet, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 164 days.

(21) Appl. No.: 10/401,824

(22) Filed: Mar. 28, 2003

(65) Prior Publication Data

US 2003/0224966 A1 Dec. 4, 2003

Related U.S. Application Data

(62) Division of application No. 10/210,386, filed on Aug. 1, 2002, now Pat. No. 6,608,010, which is a division of application No. 09/709,109, filed on Nov. 10, 2000, now Pat. No. 6,462,015.

(51) Int. Cl.[7] .............................. C11D 3/50; A61K 7/46; C07D 311/94
(52) U.S. Cl. .......................... 510/105; 512/15; 549/283
(58) Field of Search .......................... 510/105; 512/15; 549/283

(56) References Cited

U.S. PATENT DOCUMENTS

| | | | |
|---|---|---|---|
| 3,505,432 A | | 4/1970 | Neuwald |
| 3,632,396 A | | 1/1972 | Perez-Zamora |
| 3,948,818 A | | 4/1976 | Tomiyama et al. |
| 4,159,258 A | * | 6/1979 | Ohloff et al. ............. 512/13 |
| 4,223,167 A | * | 9/1980 | Willis et al. ............. 568/820 |
| 4,360,682 A | | 11/1982 | Klenk et al. |
| 5,300,489 A | | 4/1994 | Boden et al. |
| 6,479,456 B1 | * | 11/2002 | Holzner ................. 512/1 |

FOREIGN PATENT DOCUMENTS

| | | |
|---|---|---|
| WO | WO 95/12379 | 5/1995 |
| WO | WO 98/58899 | 12/1998 |

OTHER PUBLICATIONS

"The FEMA GRAS Assessment of Lactones Used as Flavour Ingredients", Adams, et al, Food and Chemical Toxicology 36 (1998), 249–278.
The Evaluation in Vitro of Fragrance Materials for Phototoxic Activity, Weinberg, et al, J.Soc.Cosmet.Chem., 32, 303–315 (Sep./Oct. 1981).

* cited by examiner

*Primary Examiner*—John Hardee
(74) *Attorney, Agent, or Firm*—Joseph F. Leightner

(57) ABSTRACT

Described are bicyclic lactones, both fused ring lactones defined according to the generic structure:

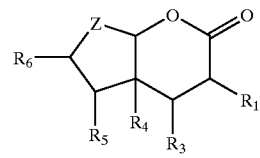

and spiro lactones defined according to the generic structure:

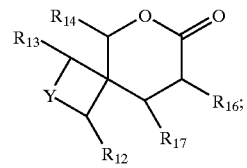

uses thereof in augmenting, enhancing or imparting aromas in or to perfume compositions, perfumed articles, colognes and perfumed polymers; processes for preparing such bicyclic lactones and intermediates therefor.

In the structure:

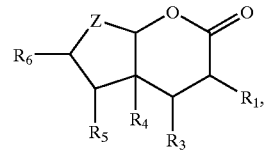

Z is one of the moieties:

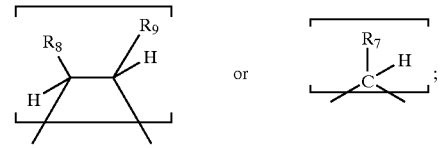

one of $R_1$ or $R_3$ is methyl and the other is hydrogen; and $R_4$, $R_5$, $R_6$, $R_7$, $R_8$ and $R_9$ are hydrogen or nonadjacent $C_1$–$C_3$ alkyl. In the structure:

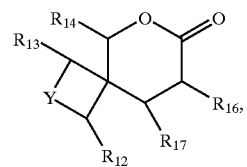

Y represents $C_2$–$C_{12}$ substituted or unsubstituted alkylidenyl, alkenylidenyl or alkadienylidenyl having the structure:

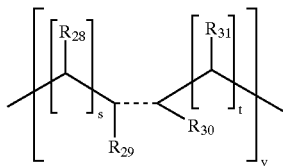

and completes a $C_5$–$C_{15}$ cycloalkyl, cycloalkadienyl or cycloalkenyl ring moiety; and wherein $R_{12}$, $R_{13}$, $R_{14}$, $R_{16}$, $R_{17}$, $R_{28}$, $R_{29}$, $R_{30}$ and $R_{31}$ represent hydrogen or $R_1$ or $R_3$ nonadjacent alkyl; wherein s is an integer of from 0 up to 10; t is an integer of from 0 up to 10; and v is an integer of 1 or 2; with the proviso that the sum of s and t is between 0 and 10 according to the inequalities: $0 \leq s+t \leq 10$; $0 \leq s \leq 10$; and $0 \leq t \leq 10$.

7 Claims, 55 Drawing Sheets

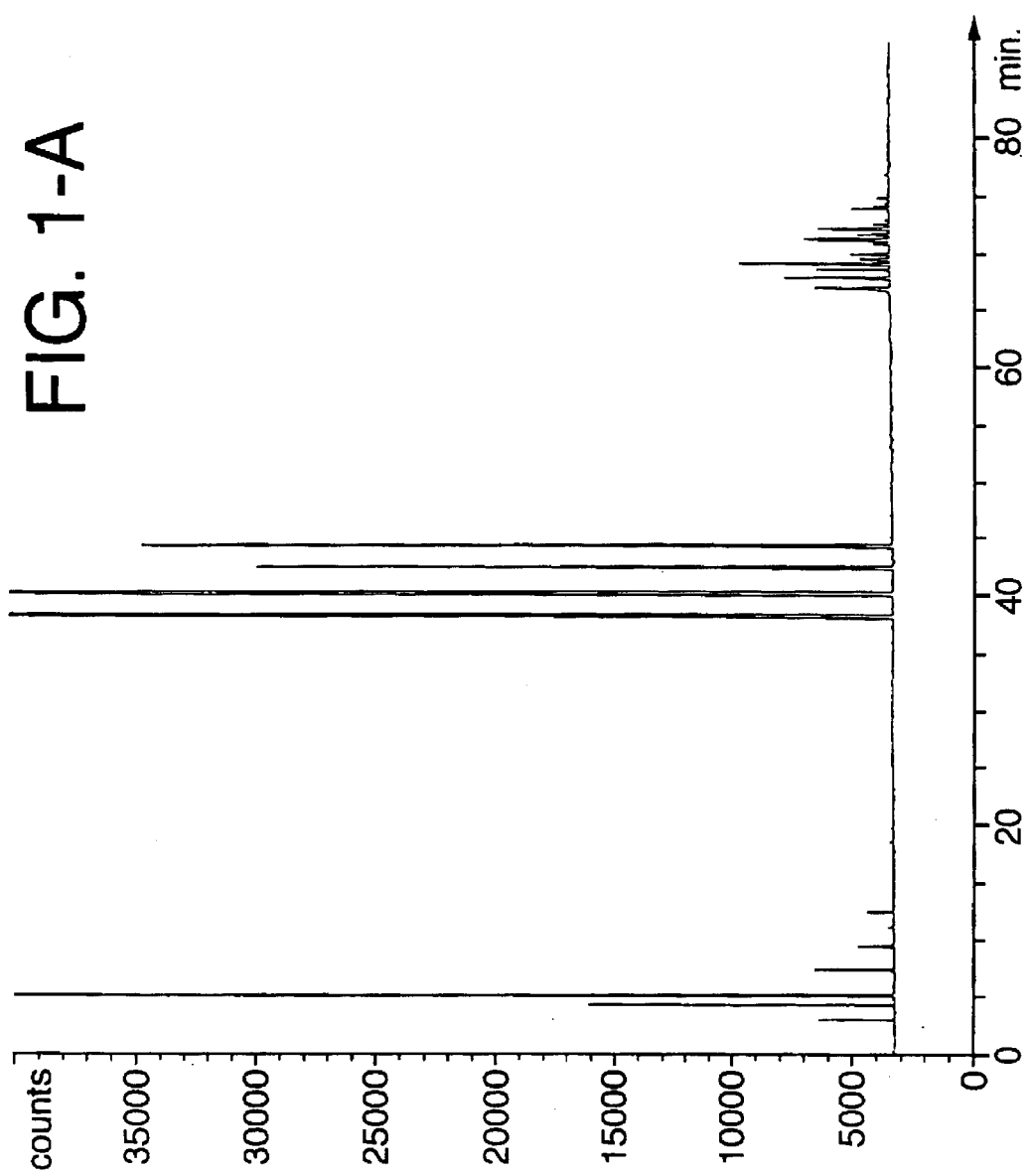
FIG. 1-A

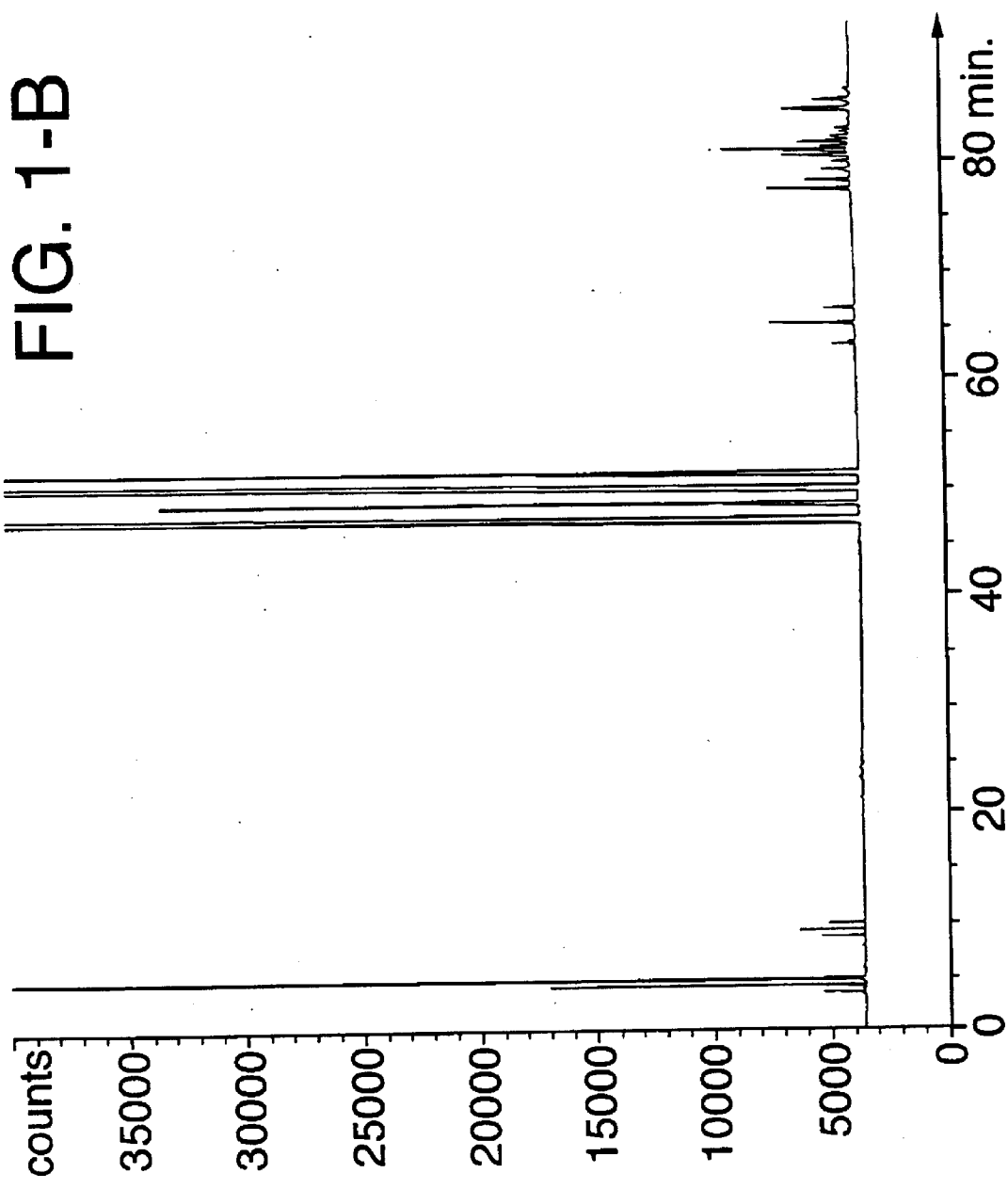
FIG. 1-B

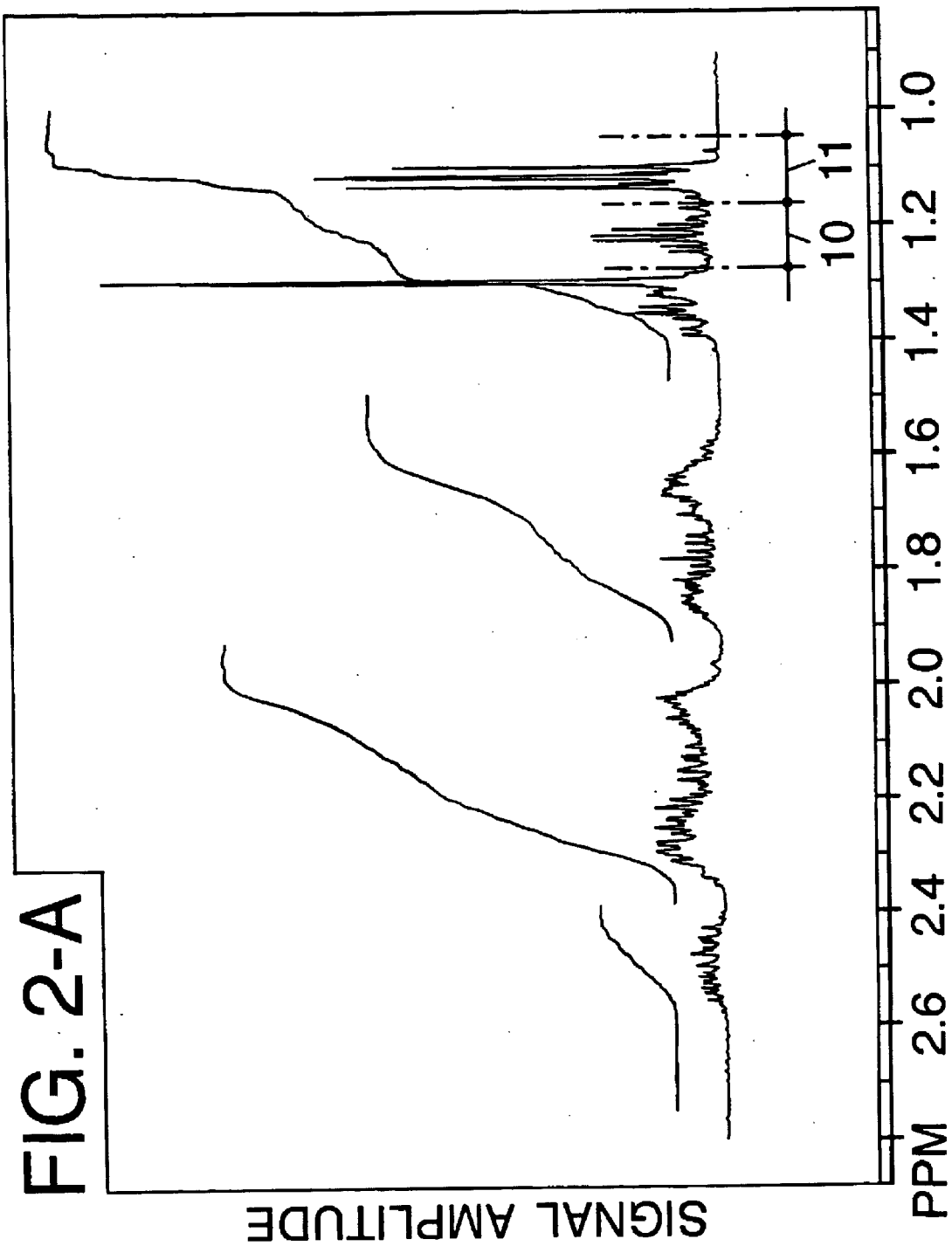
FIG. 2-A

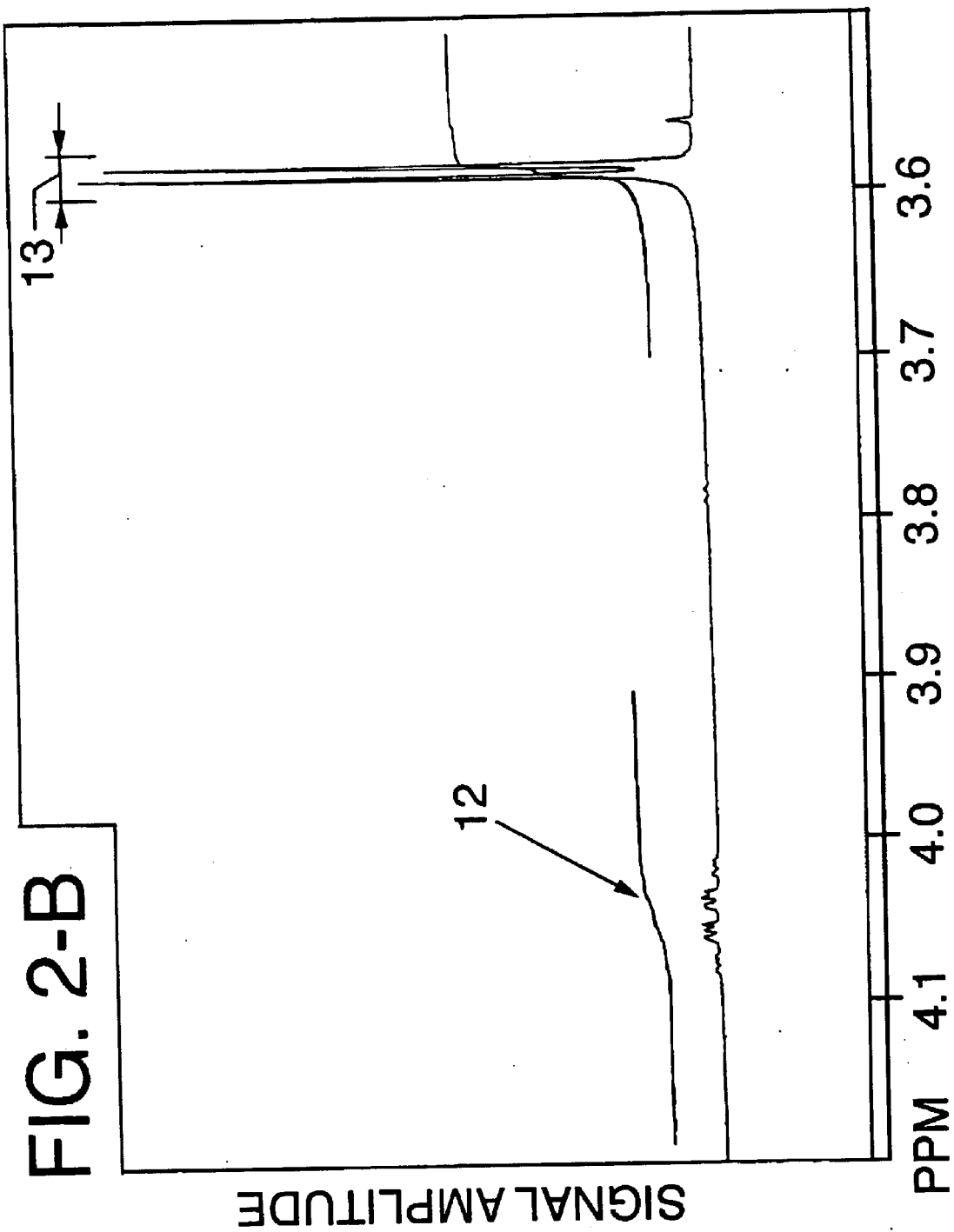

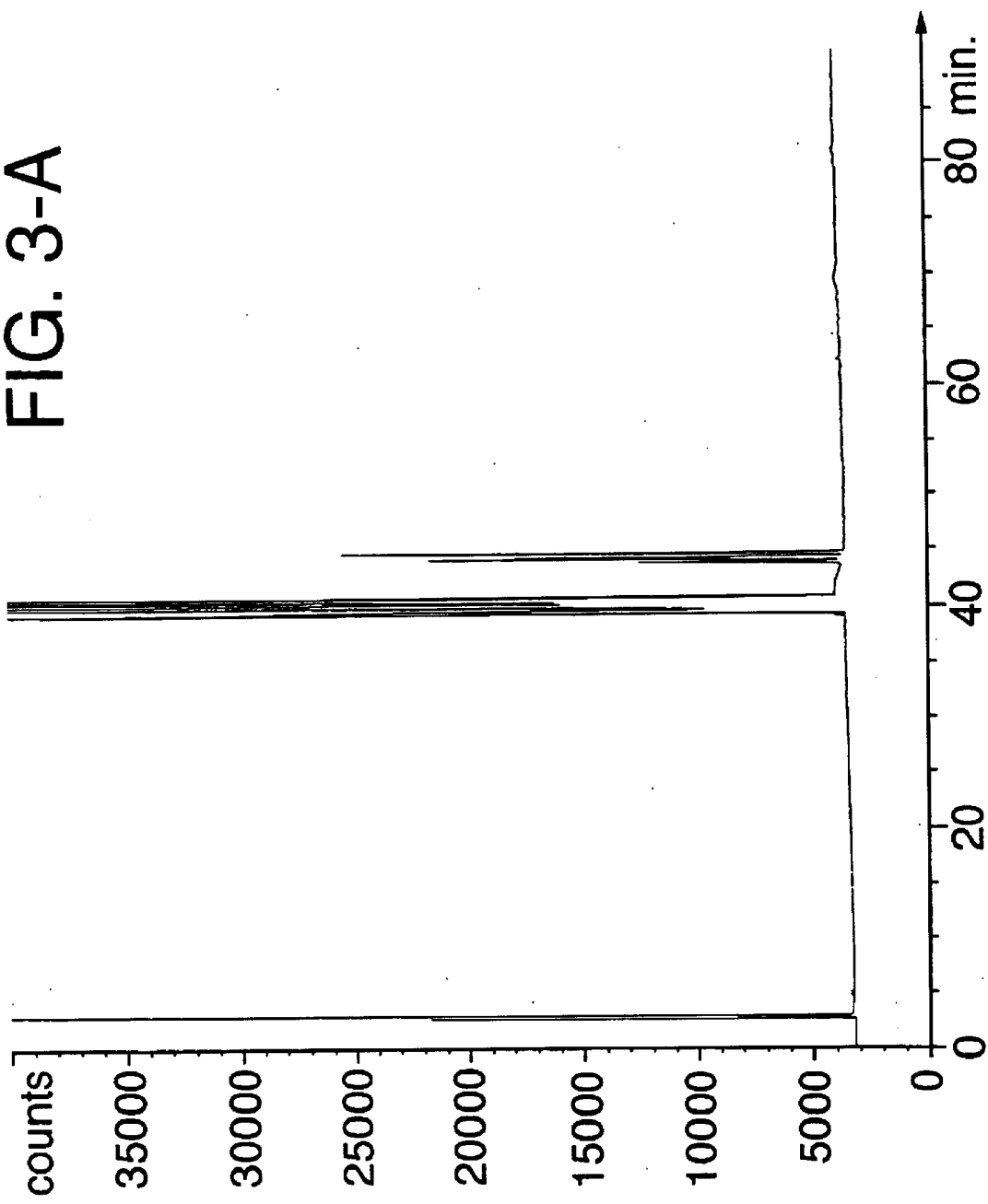

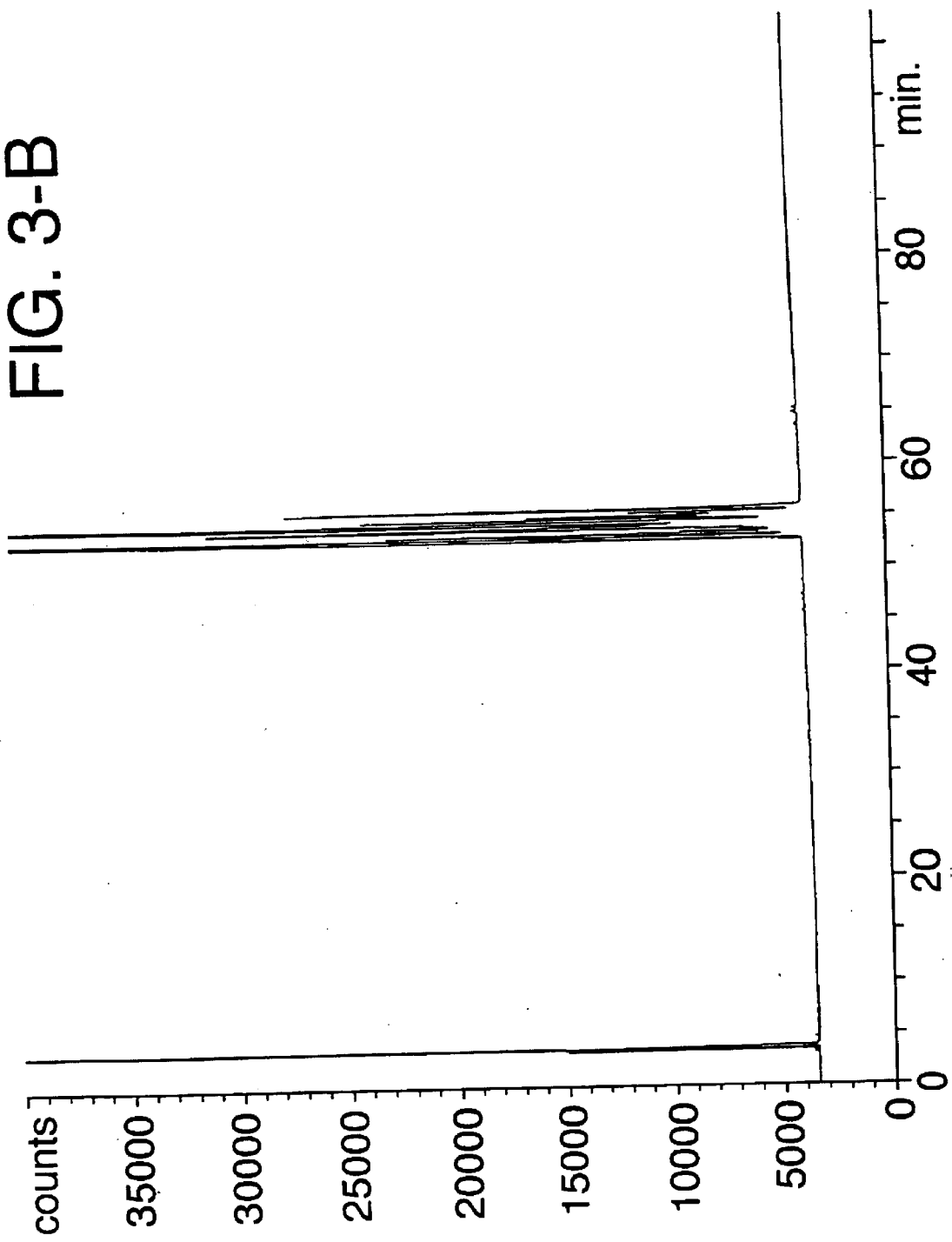

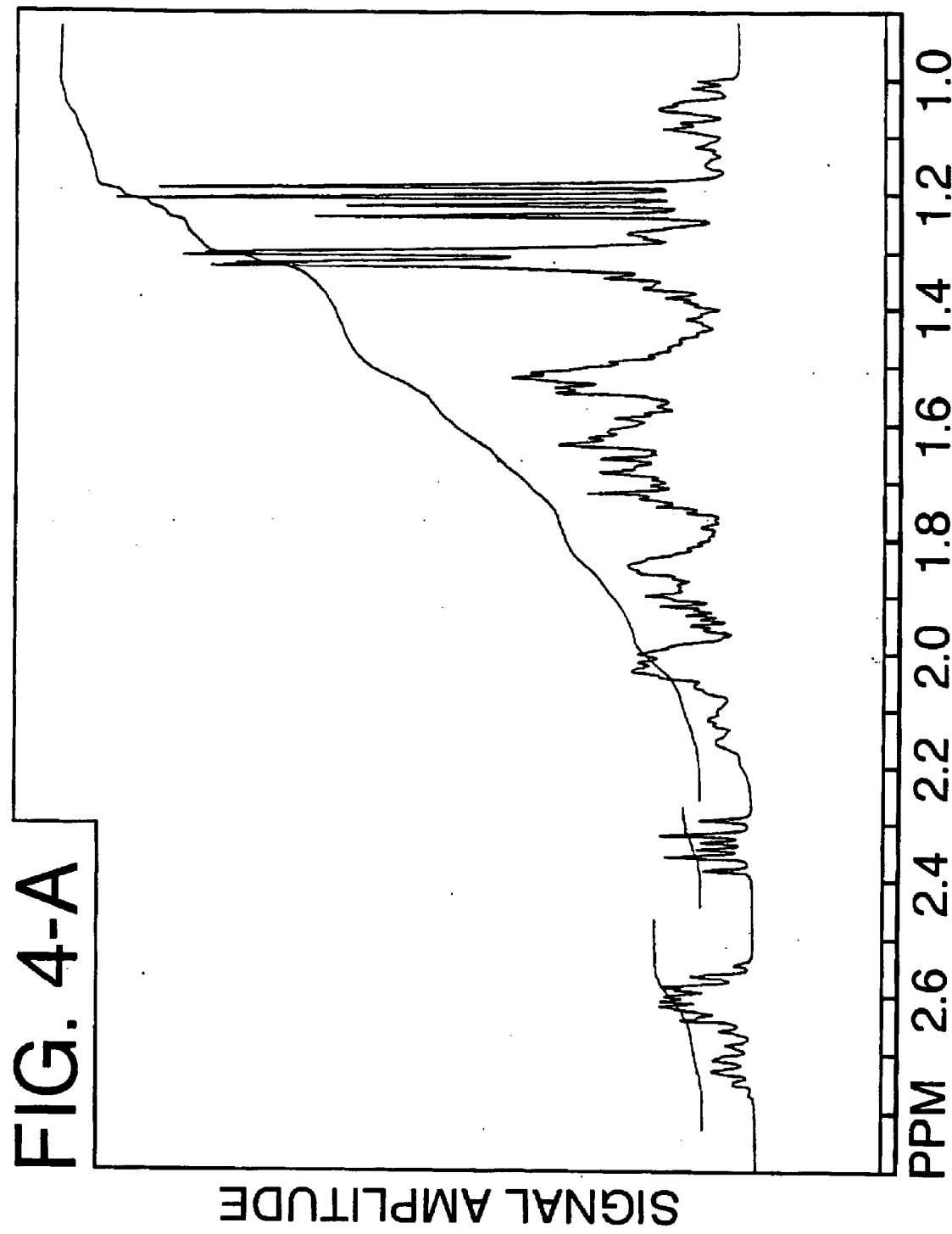
FIG. 4-A

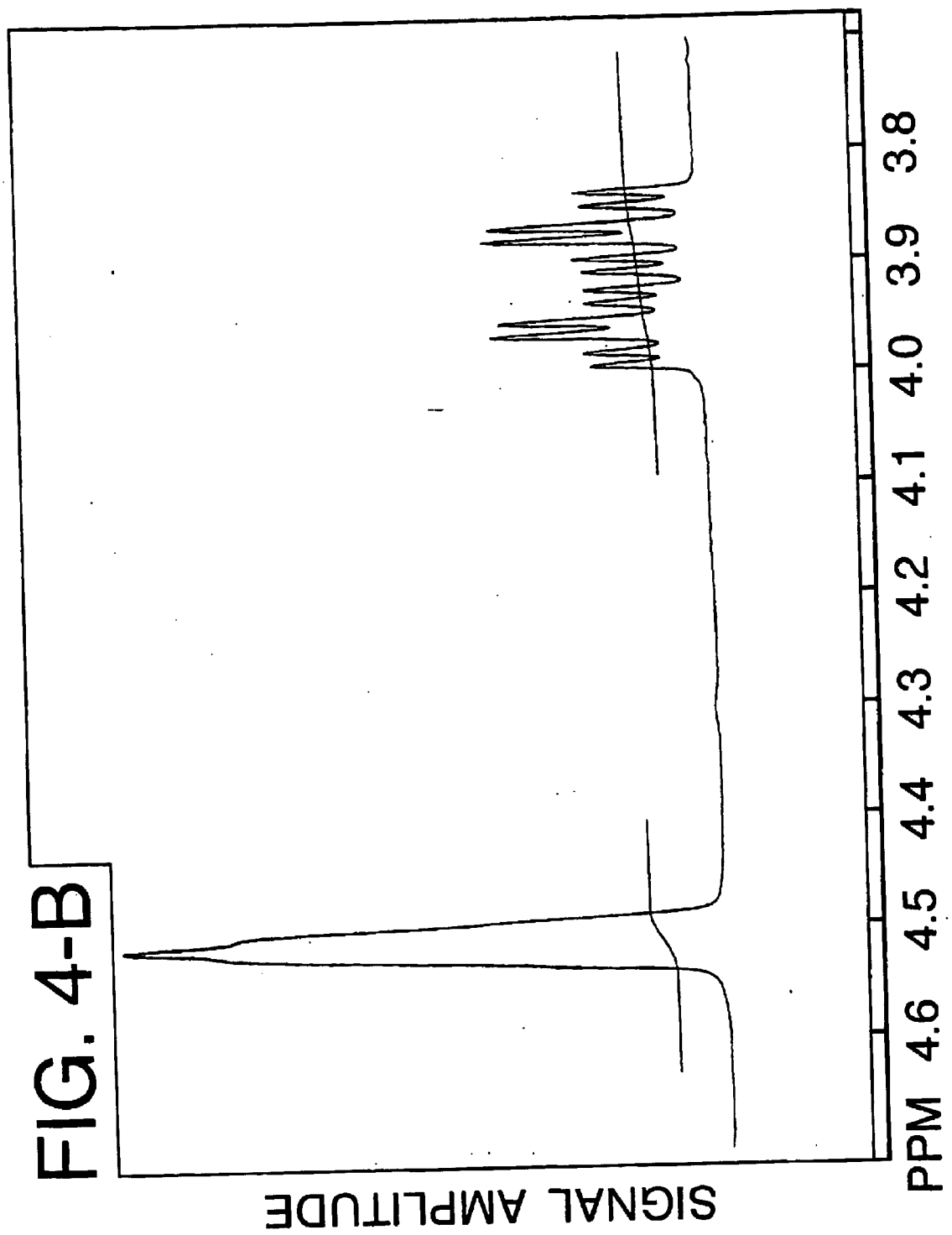

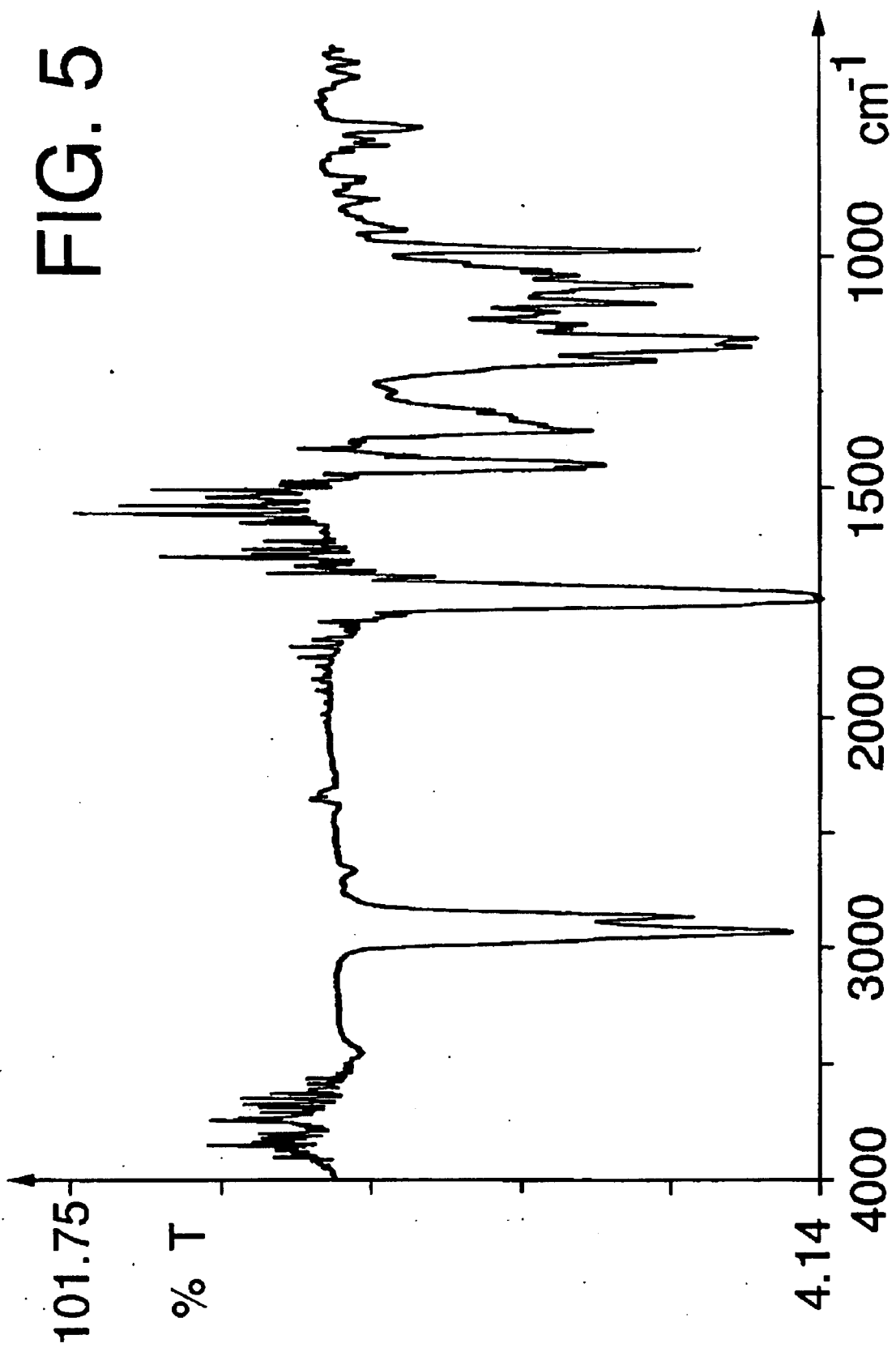

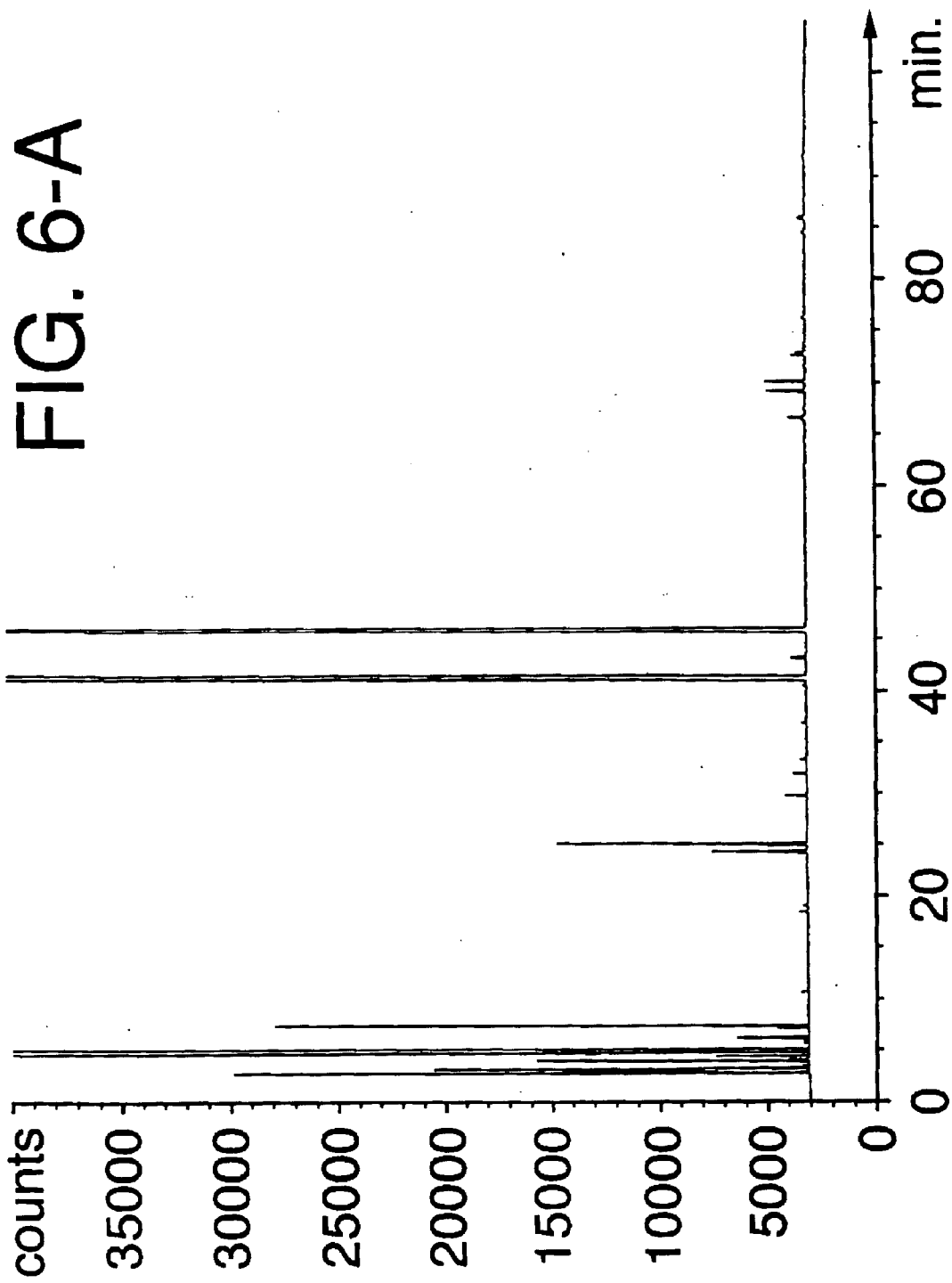

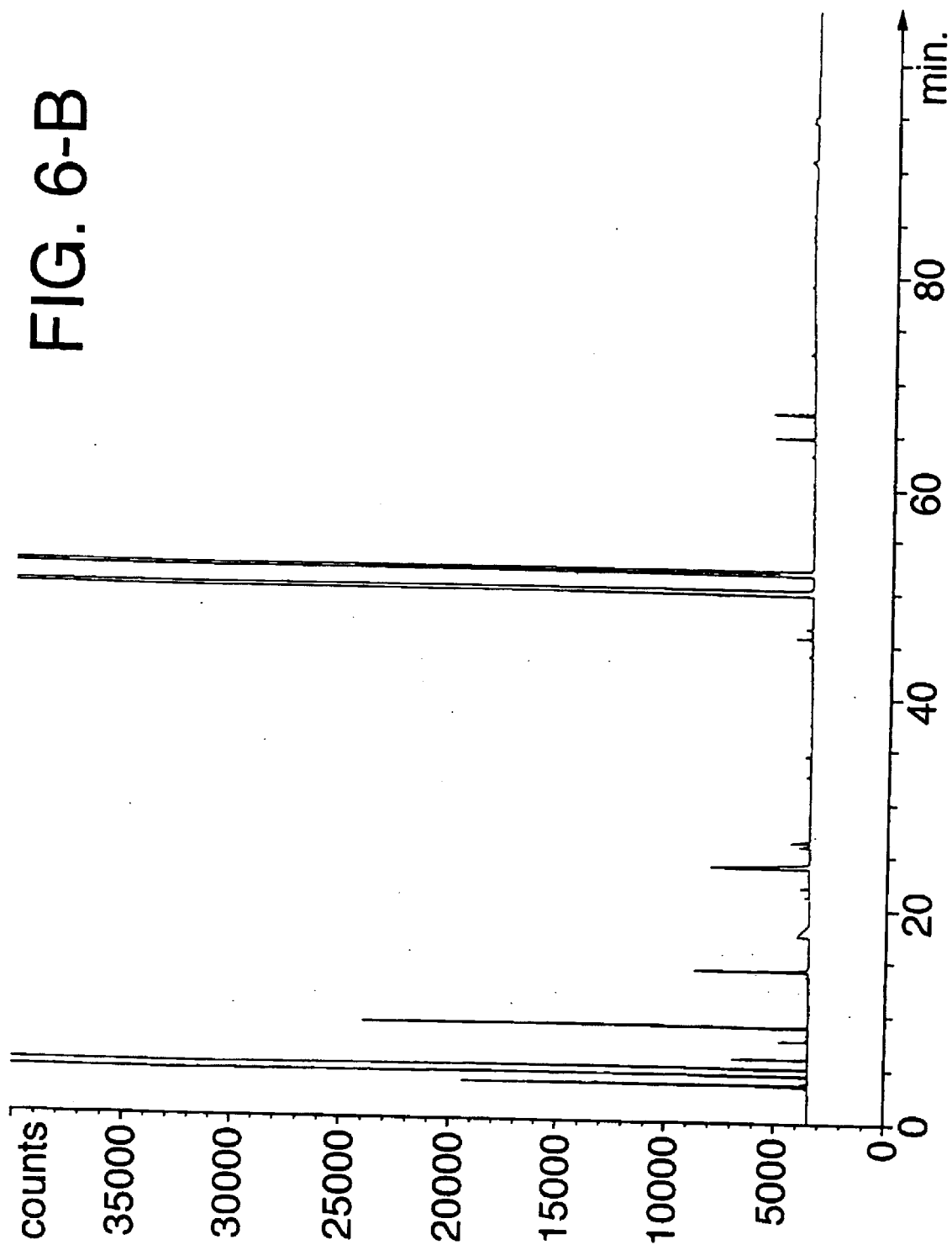

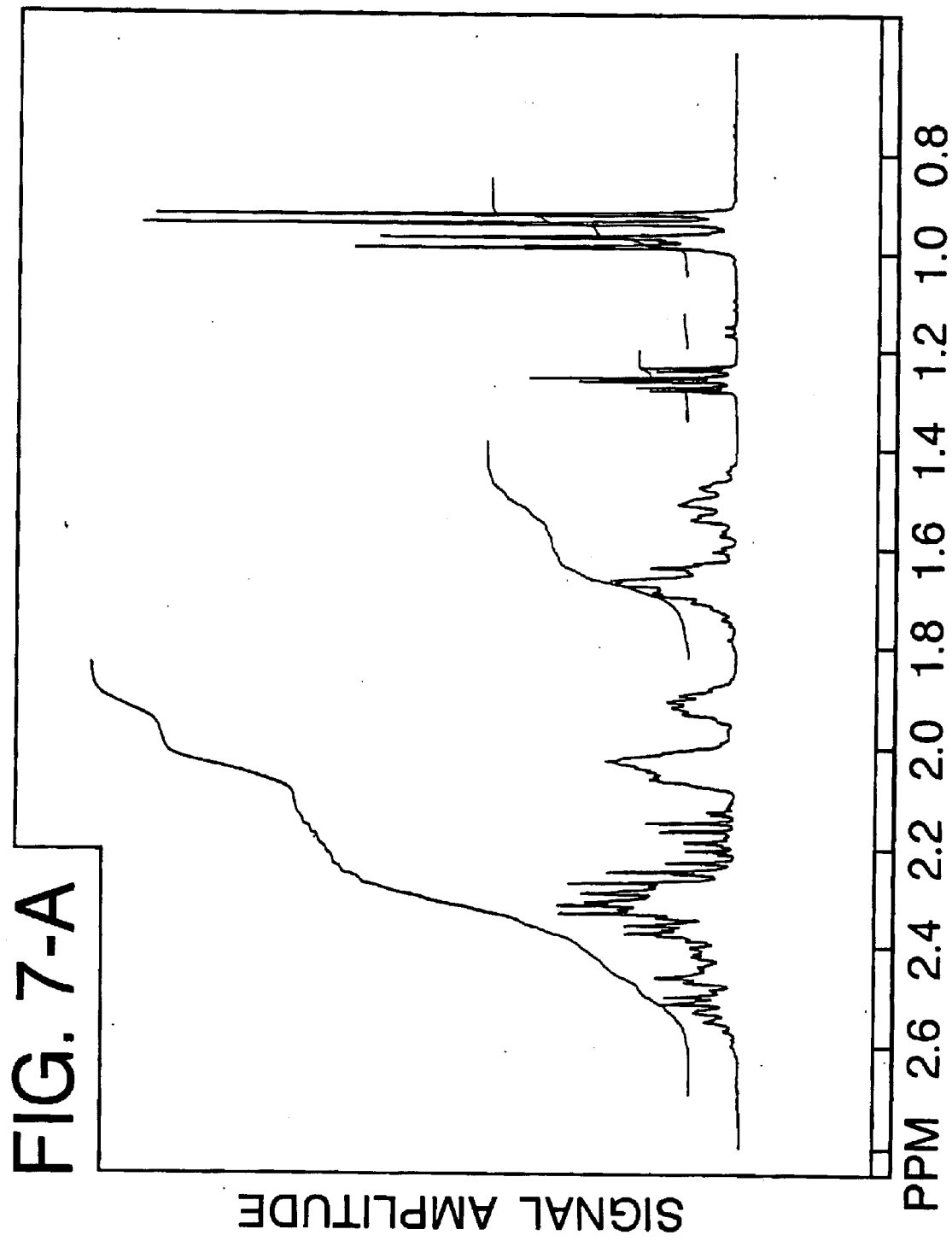

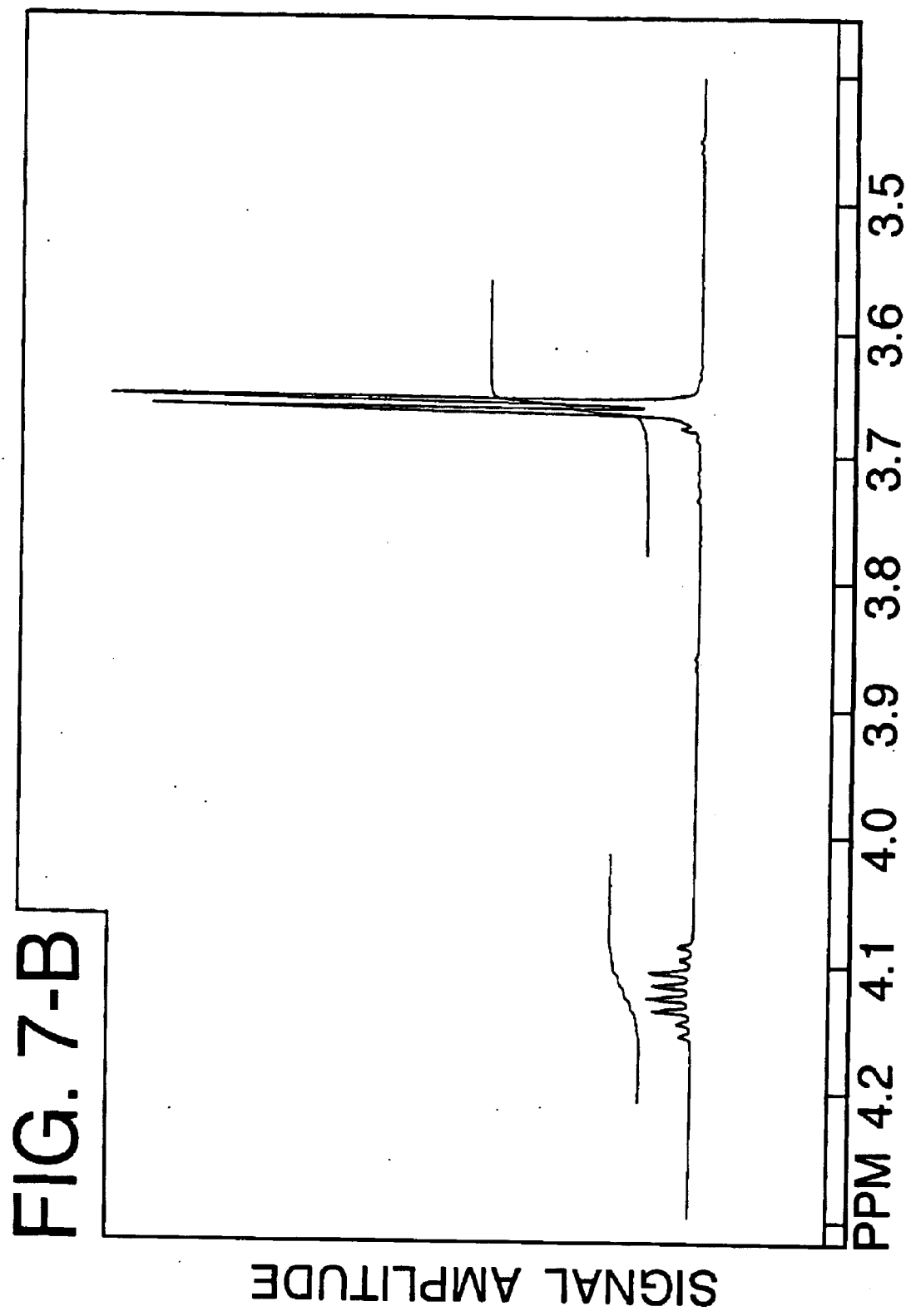

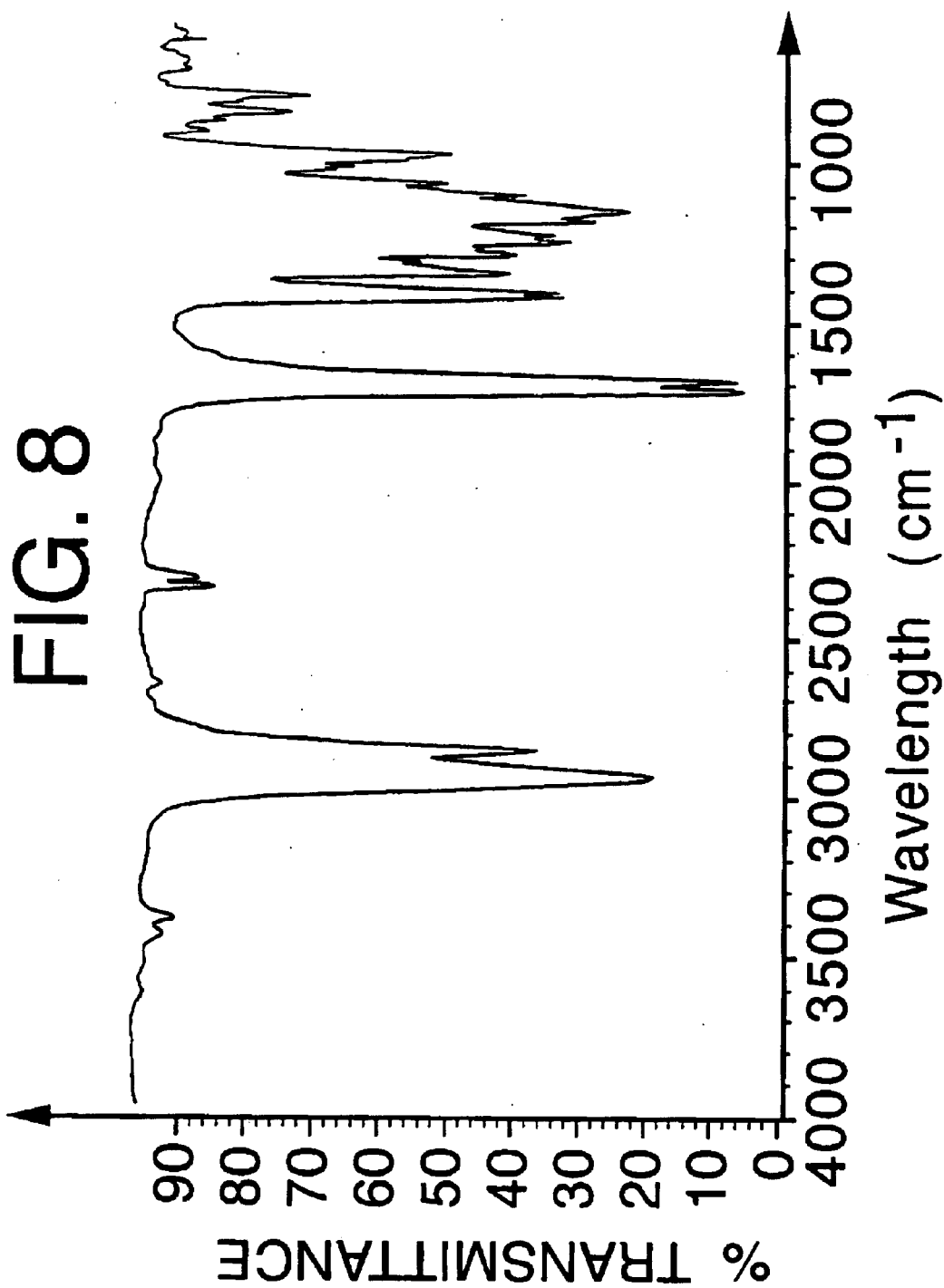

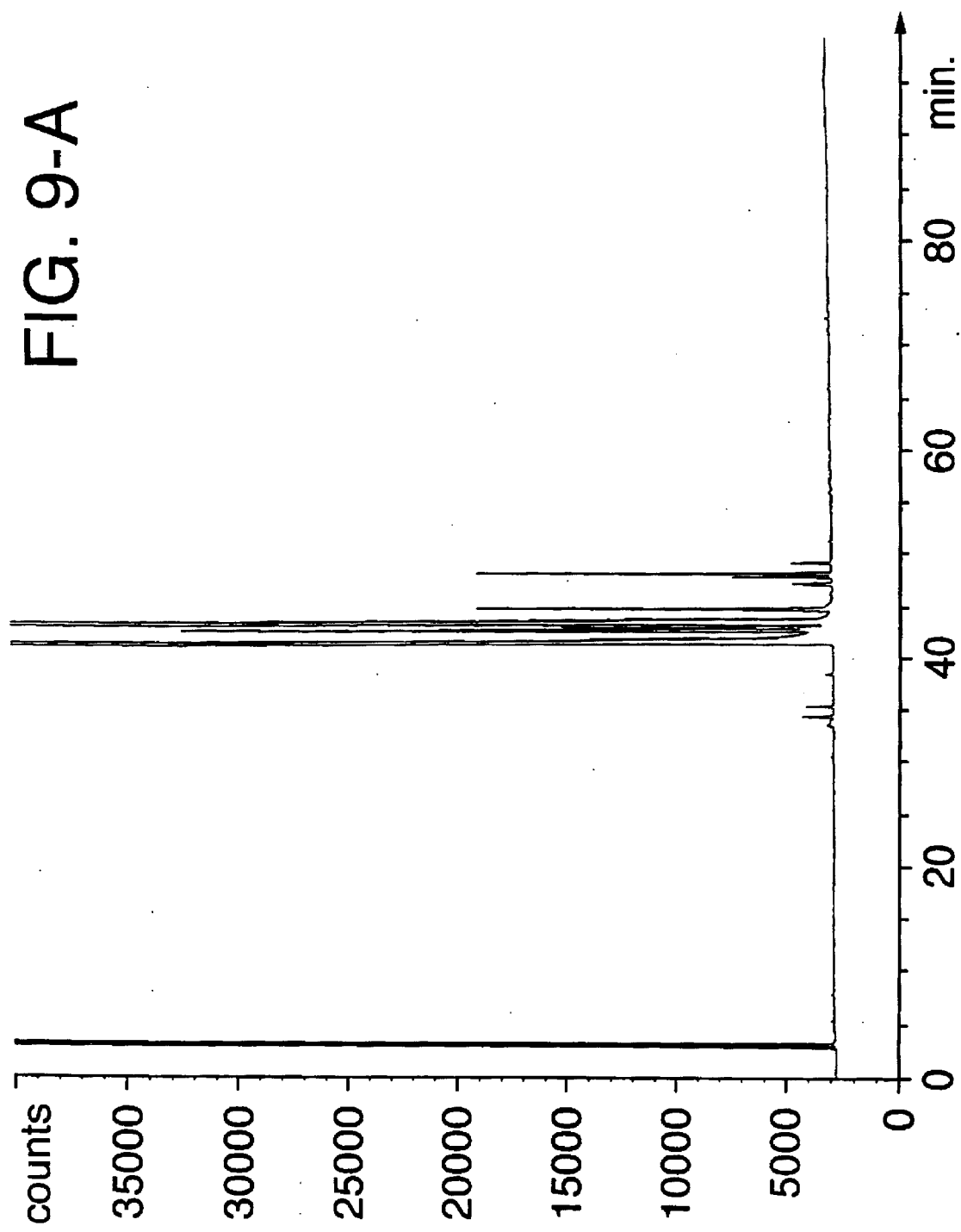

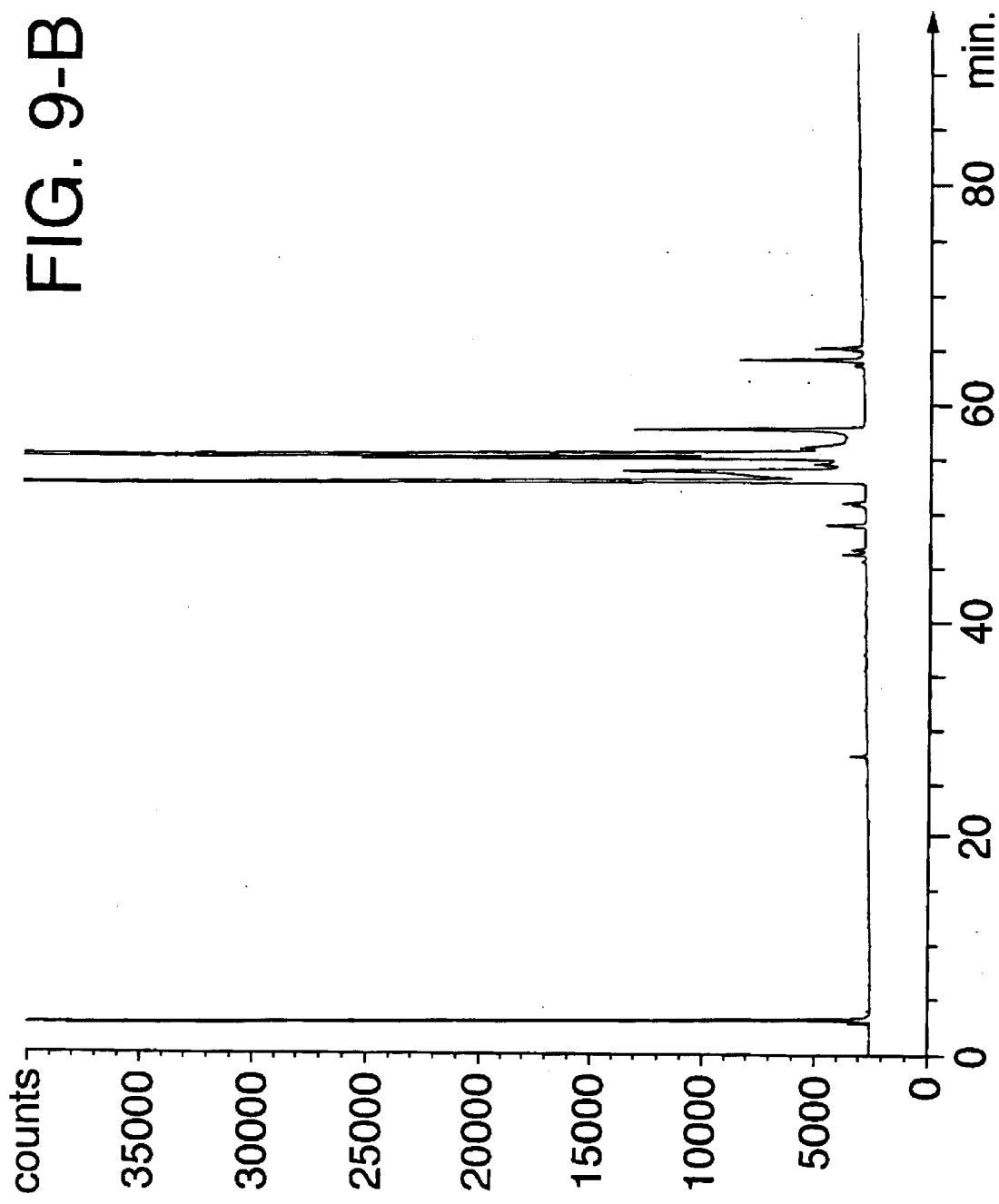

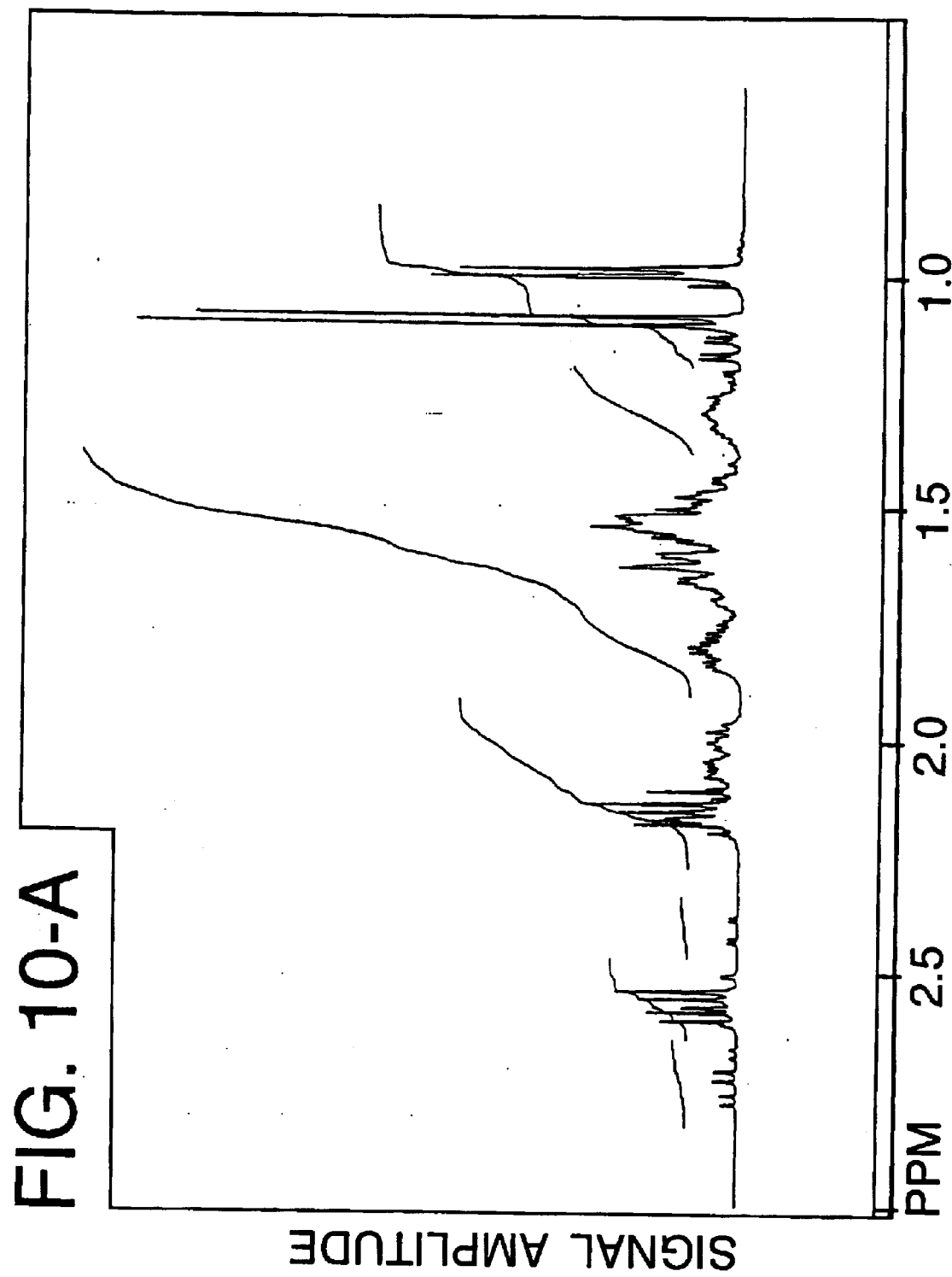
FIG. 10-A

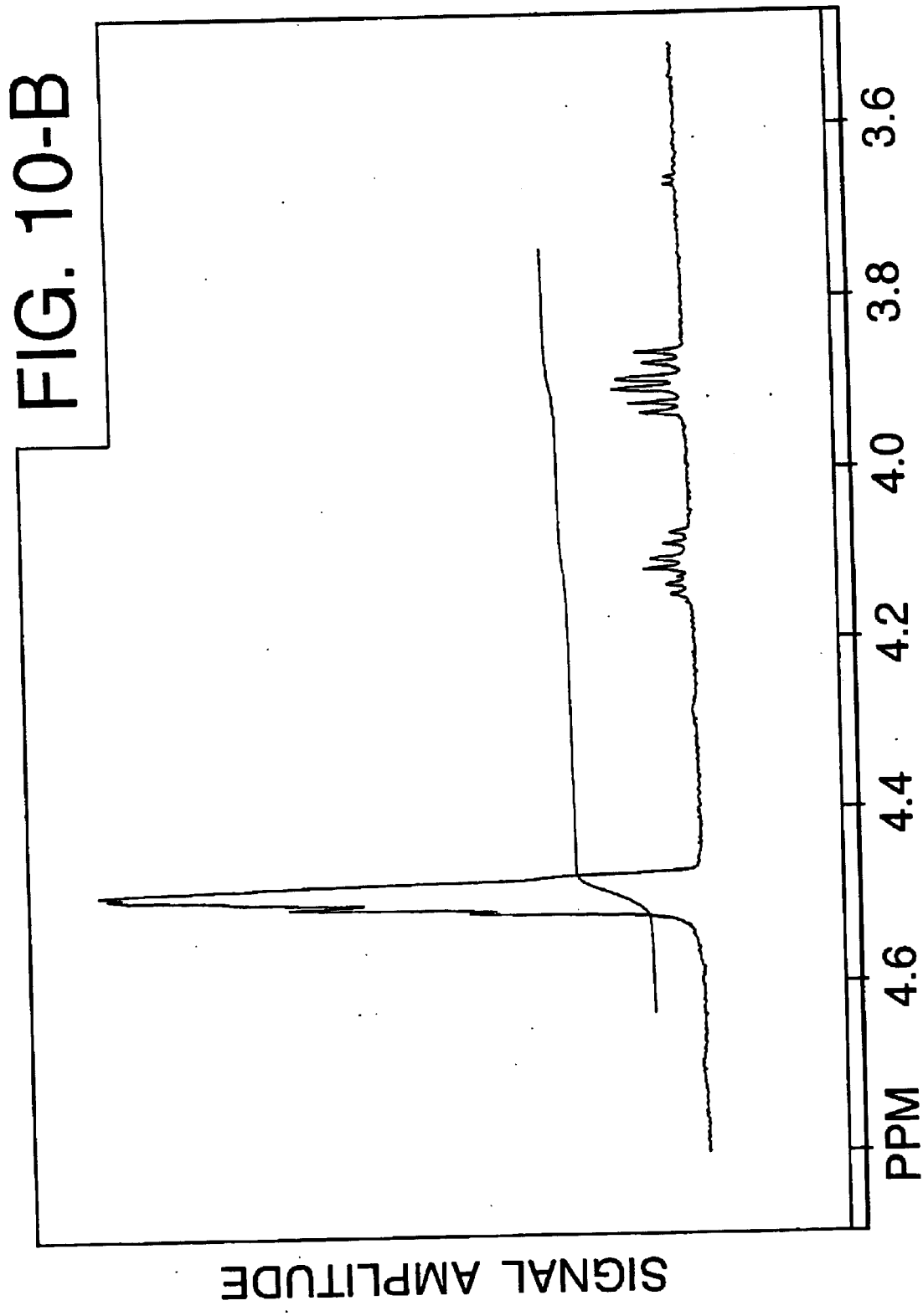
FIG. 10-B

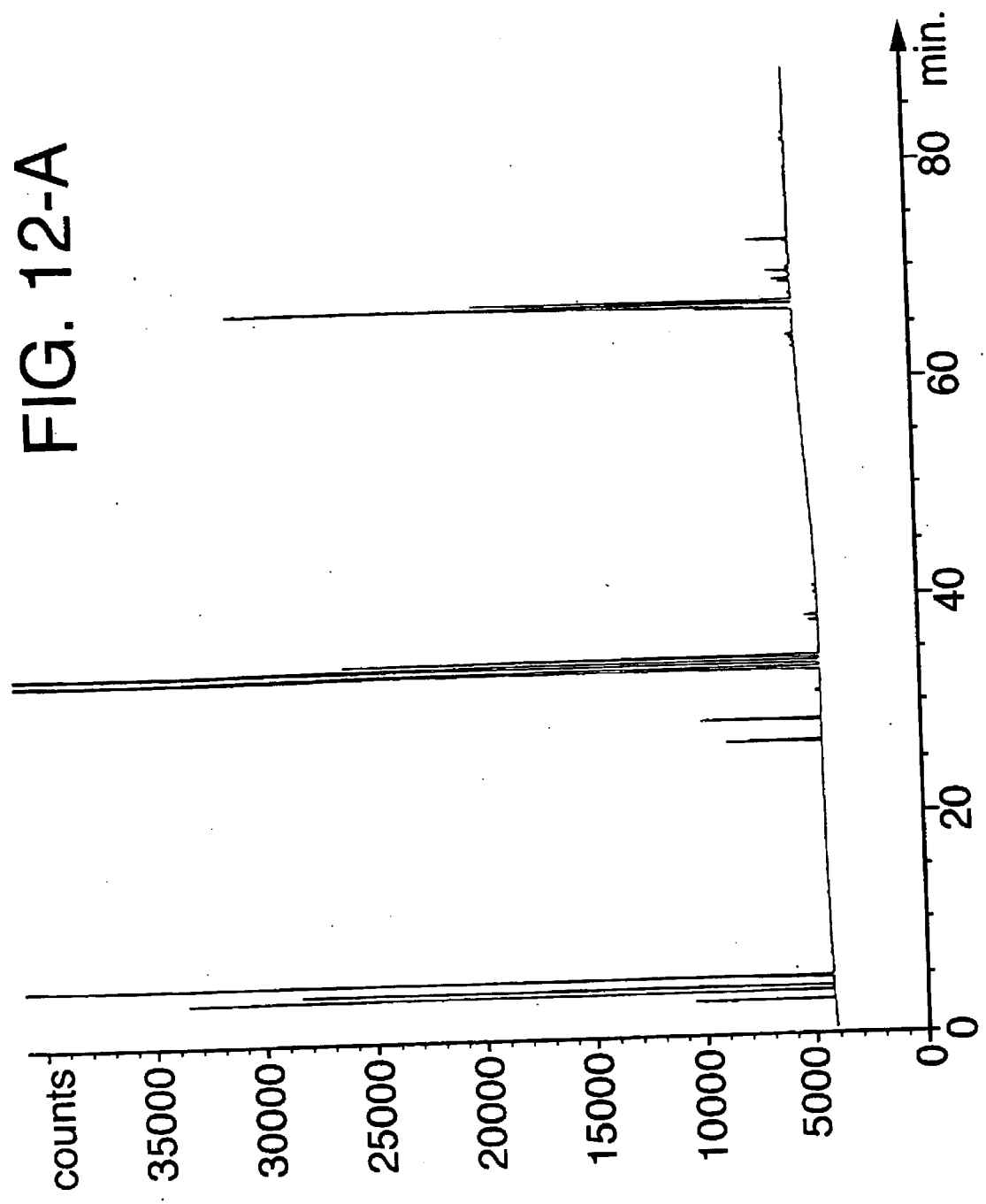

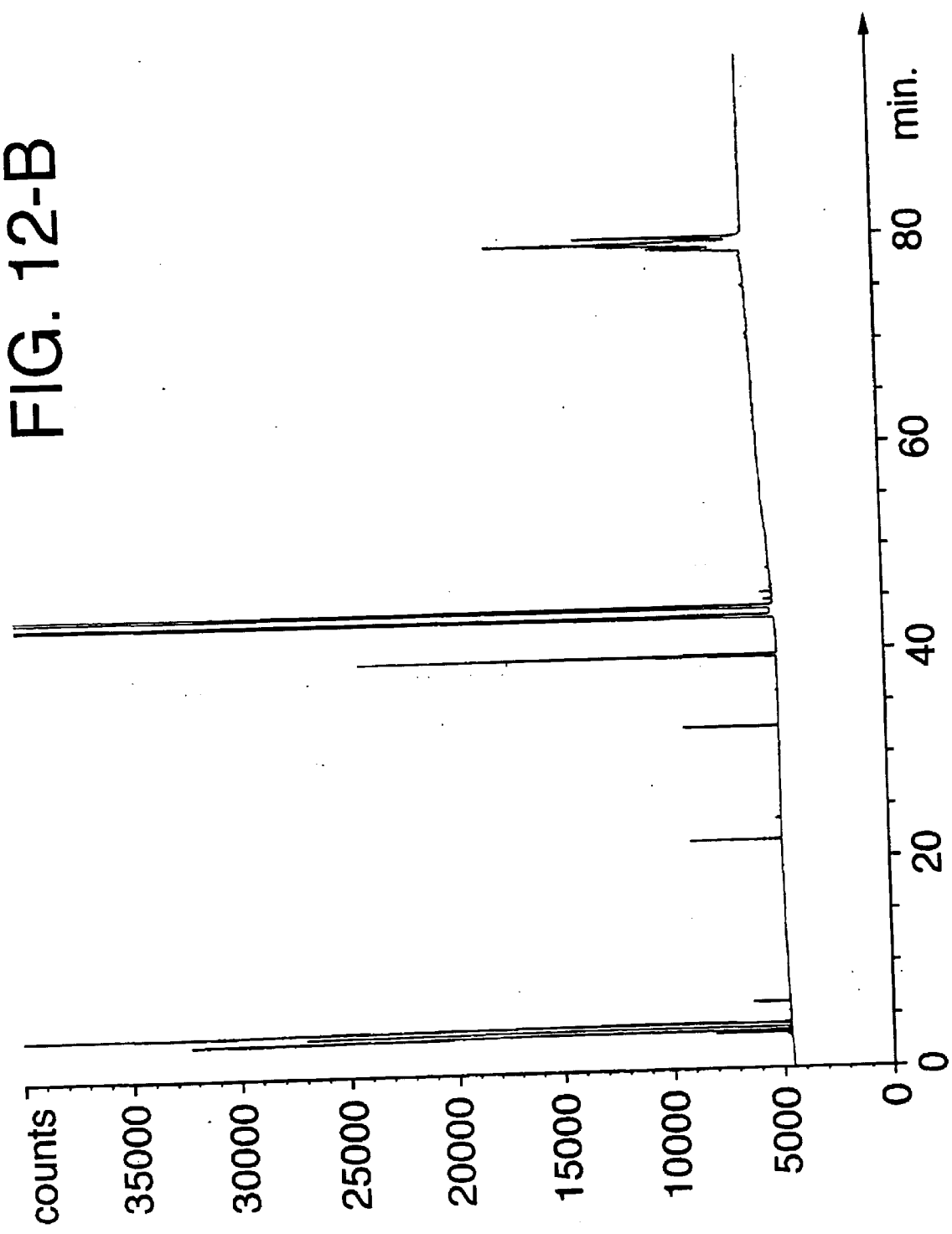

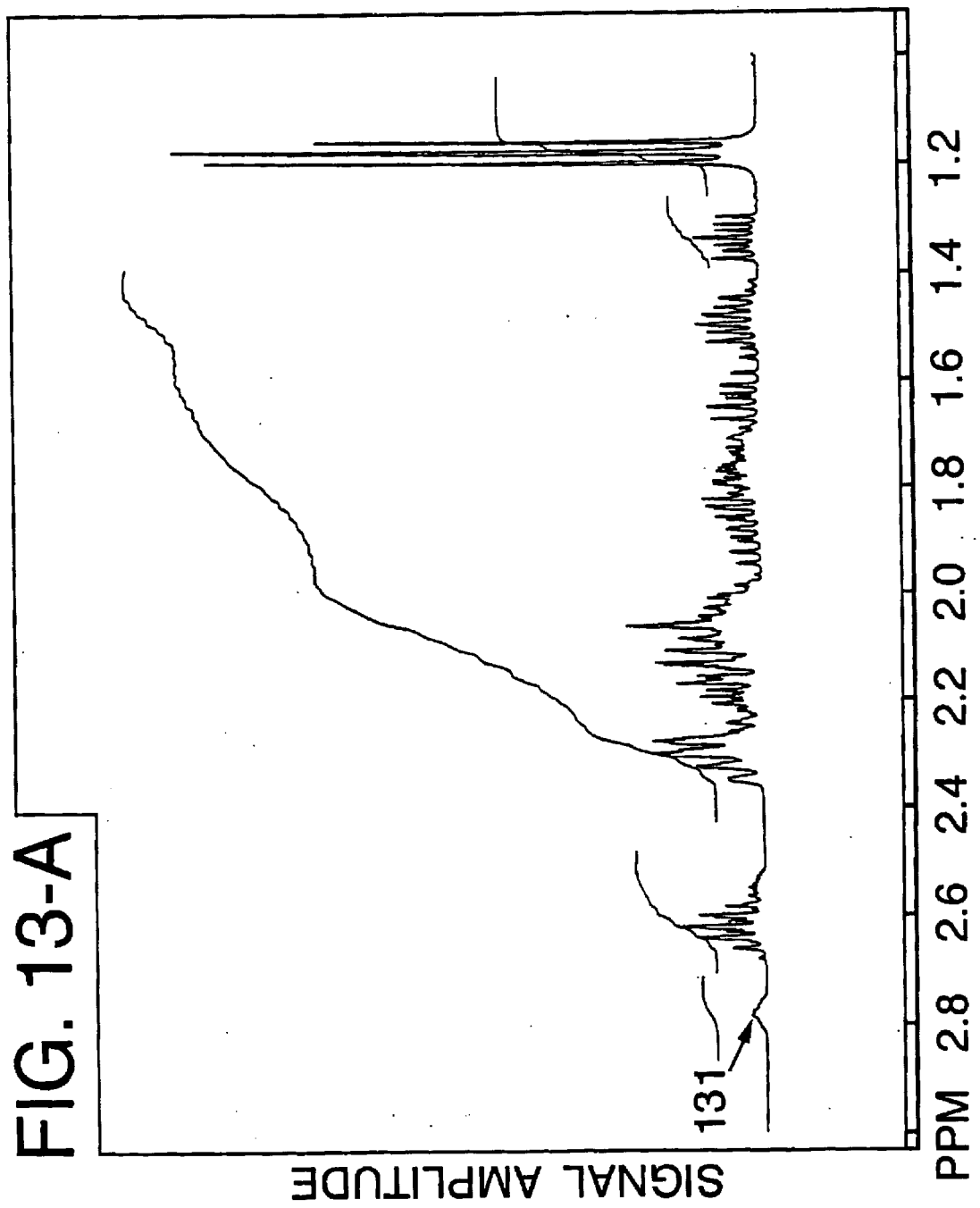

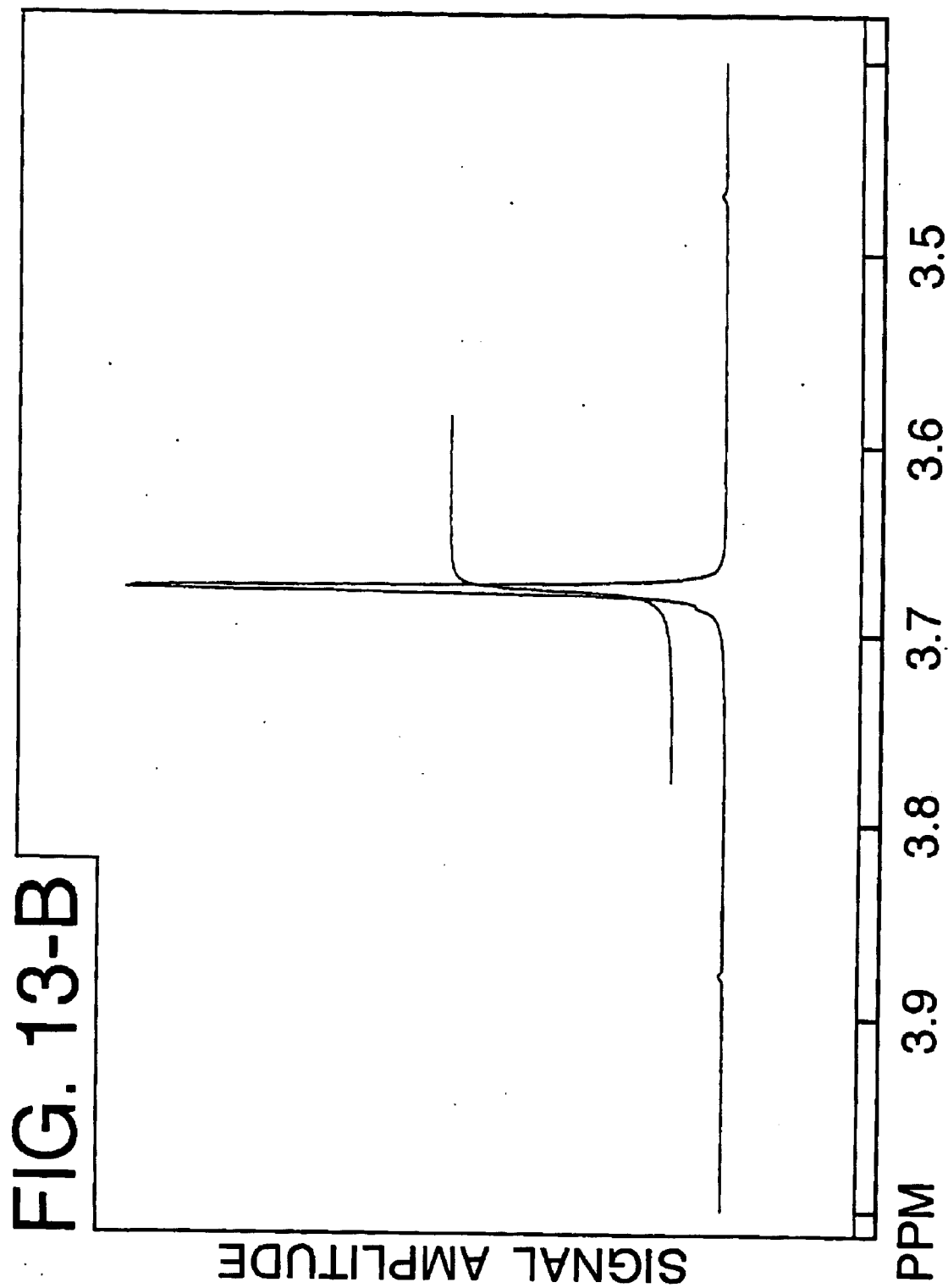
FIG. 13-B

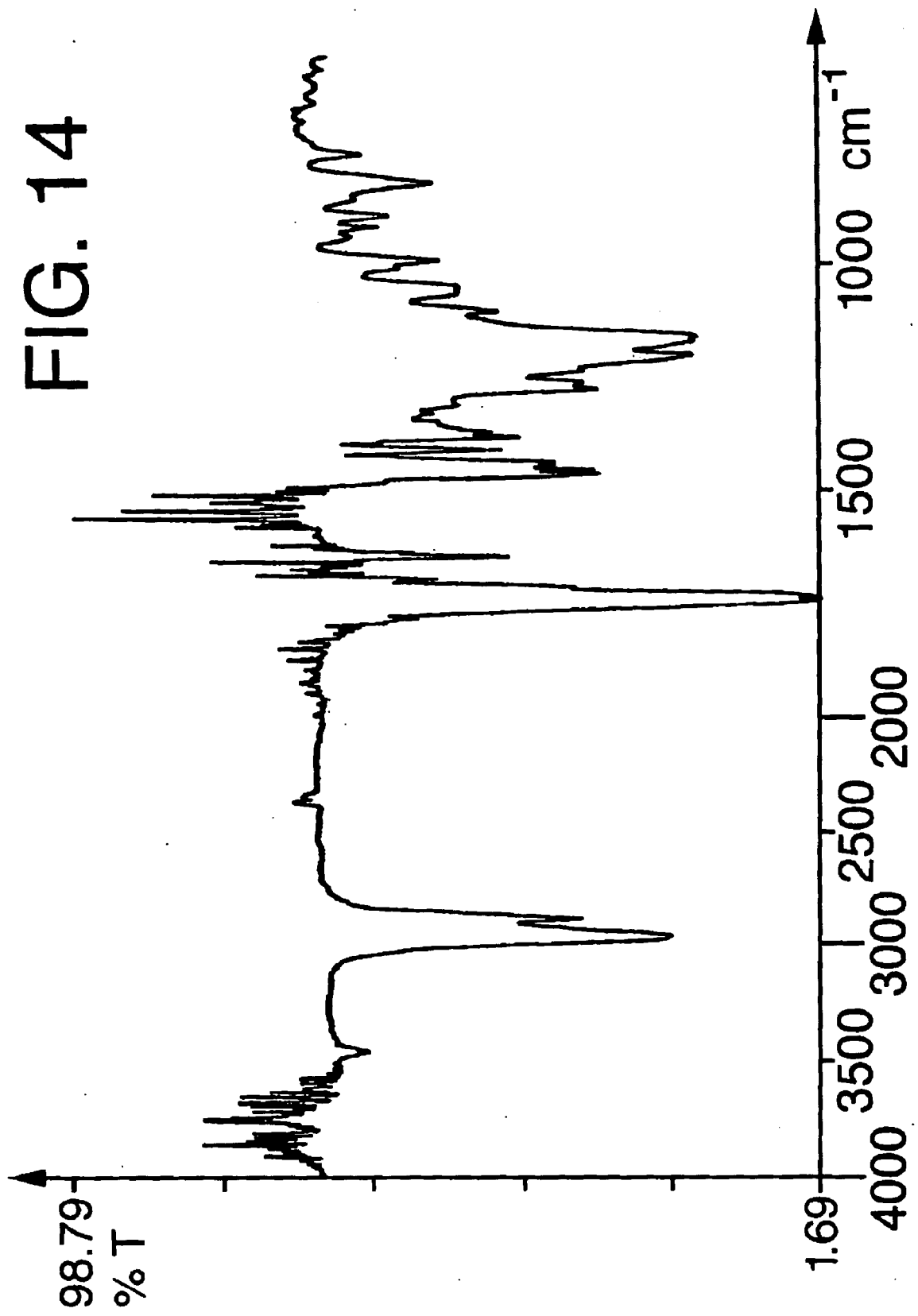

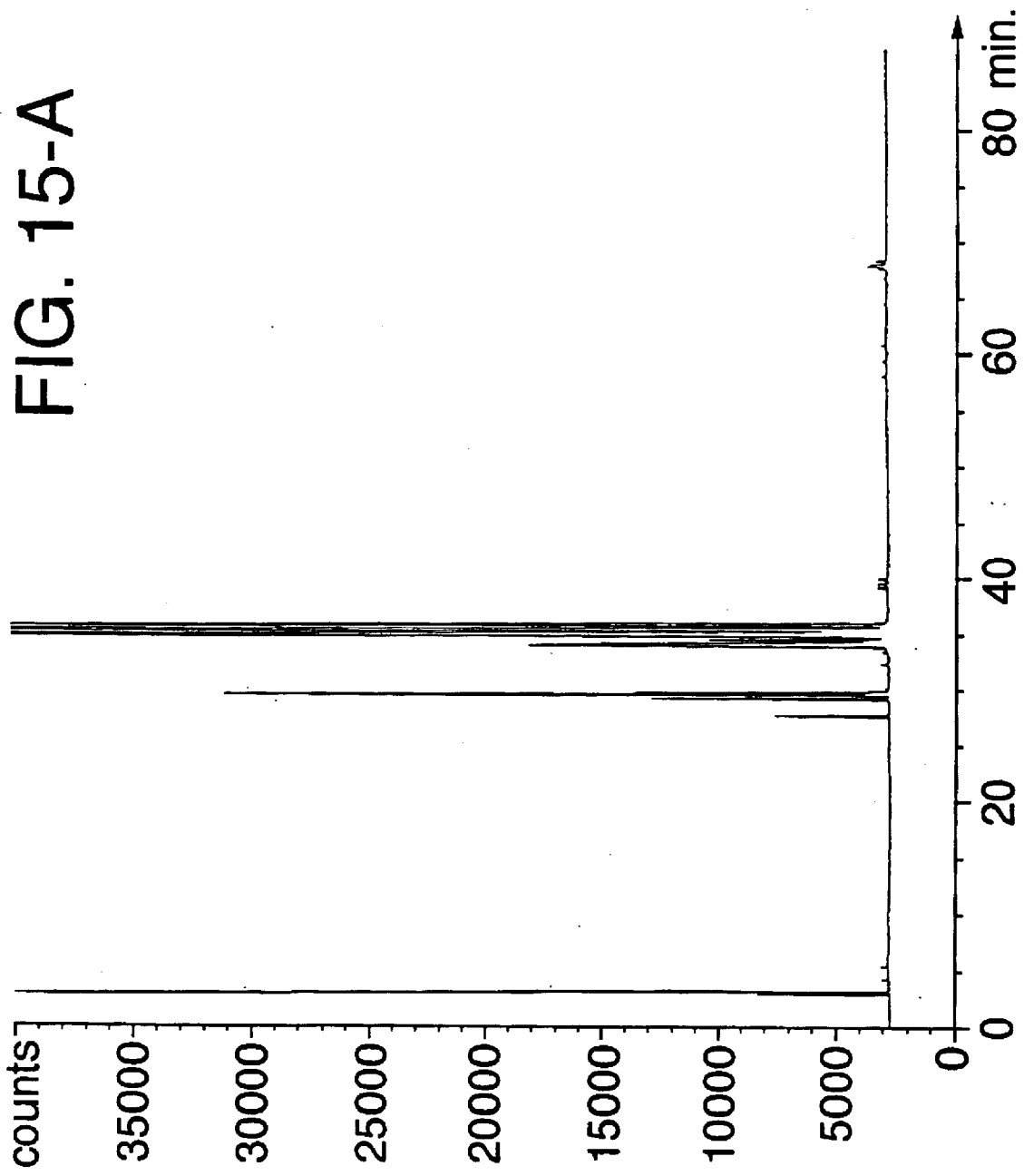

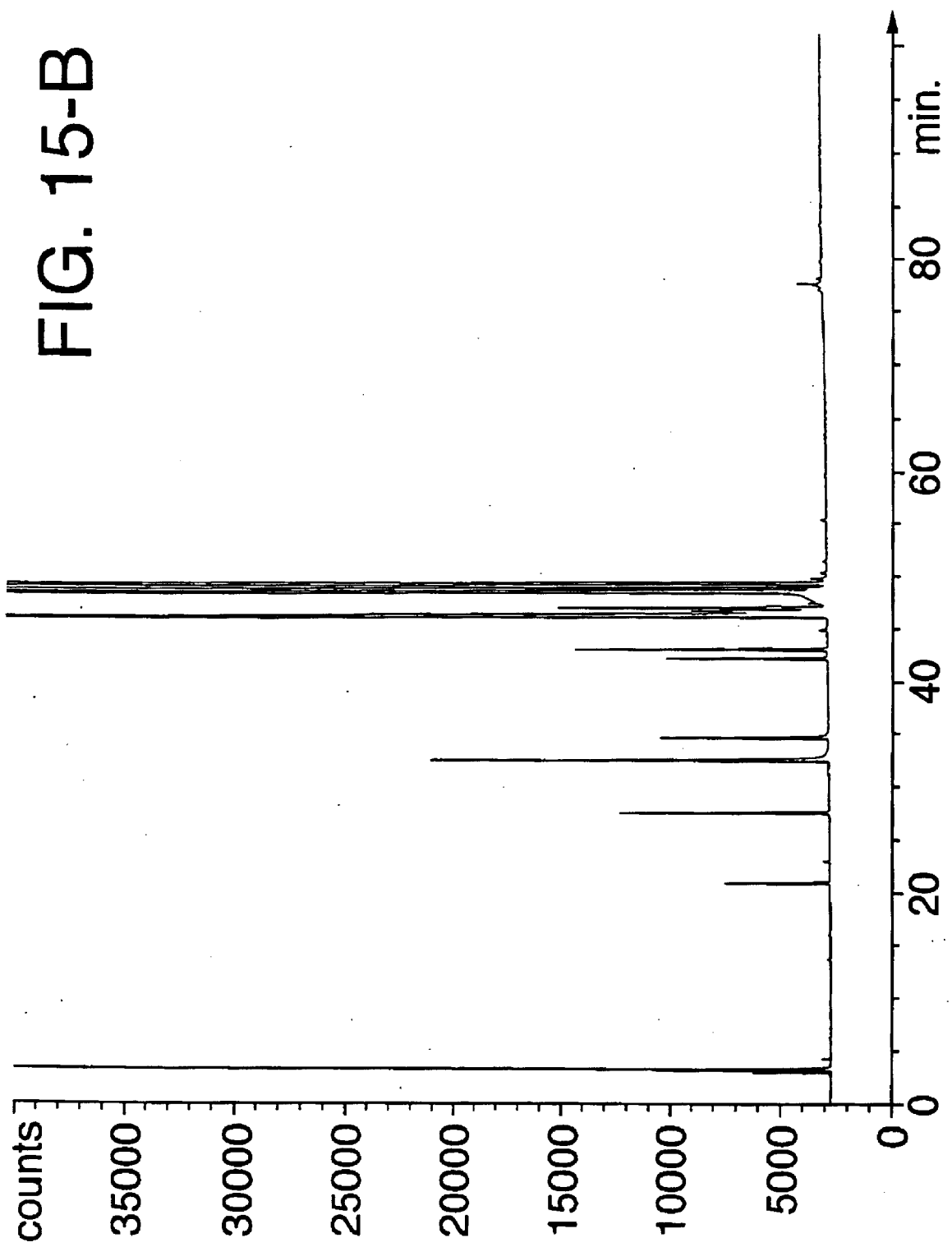

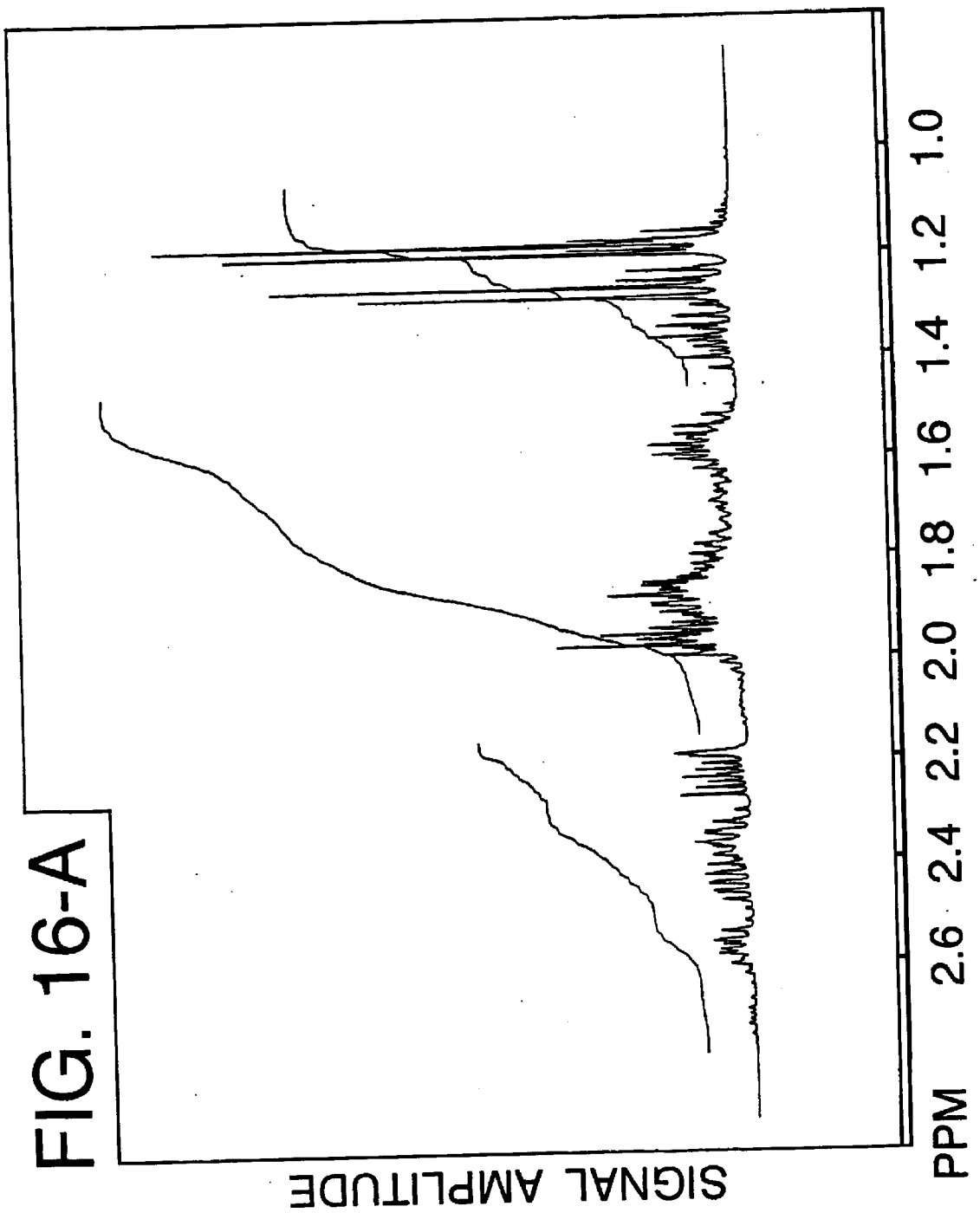
FIG. 16-A

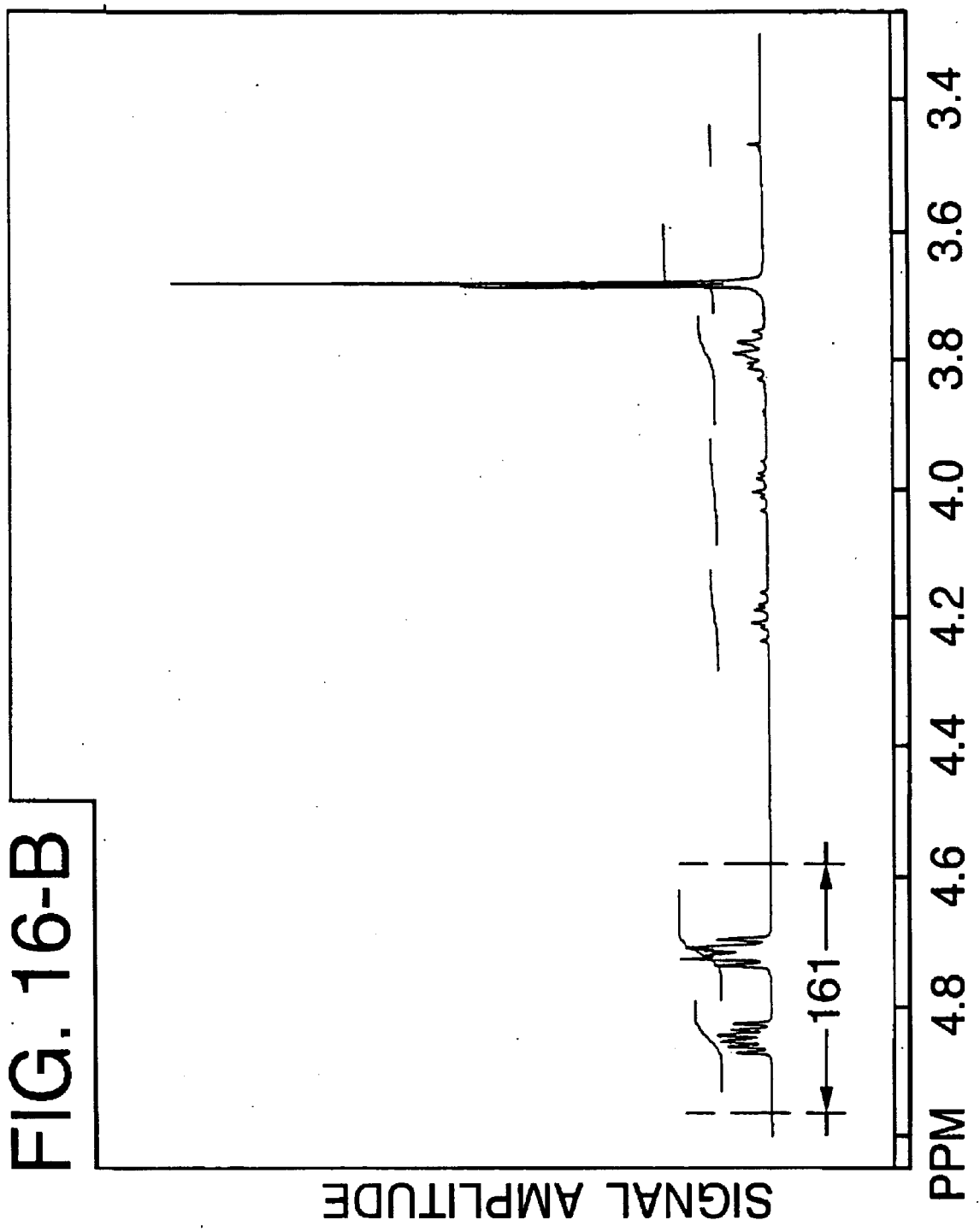
FIG. 16-B

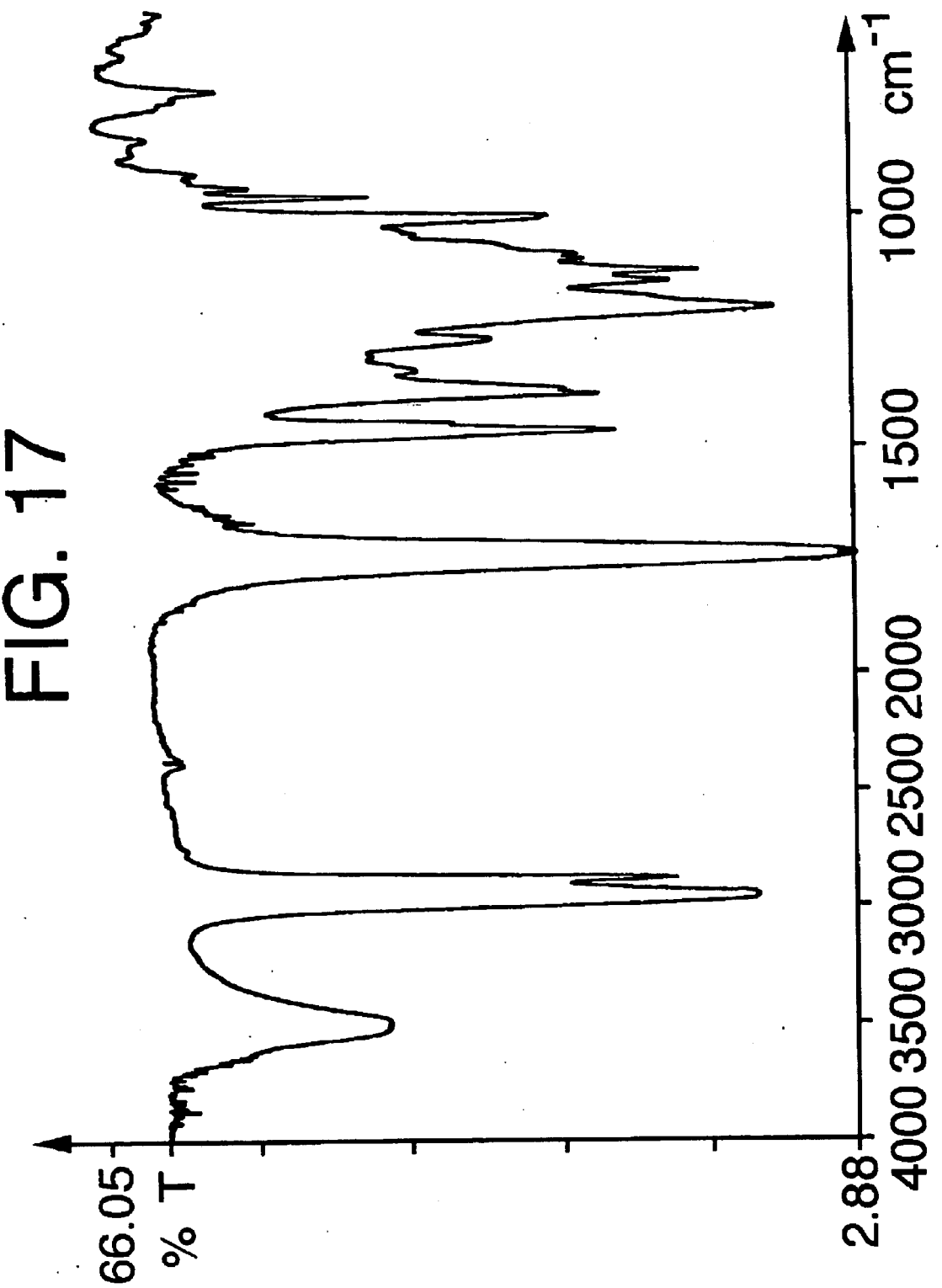

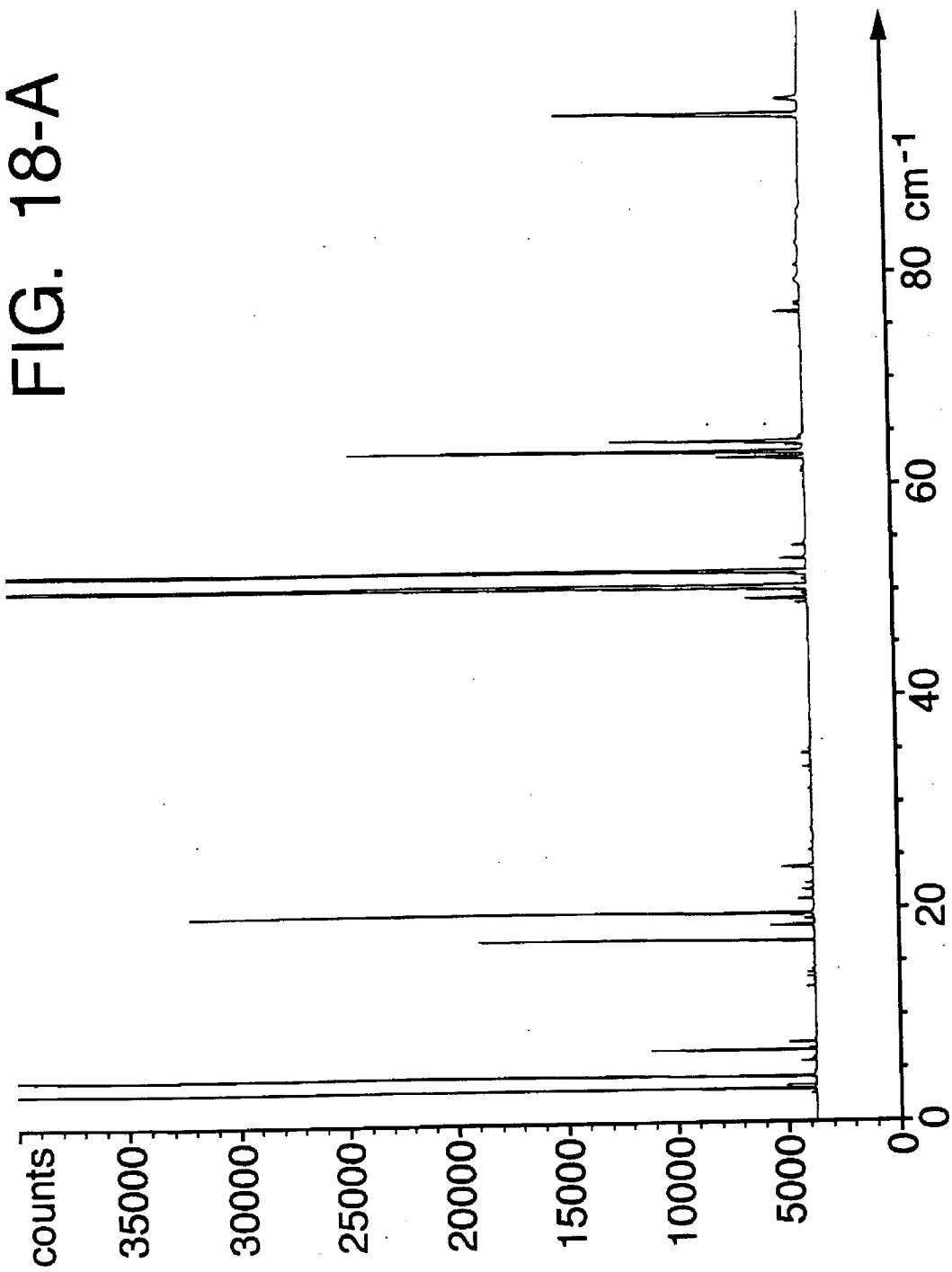
FIG. 18-A

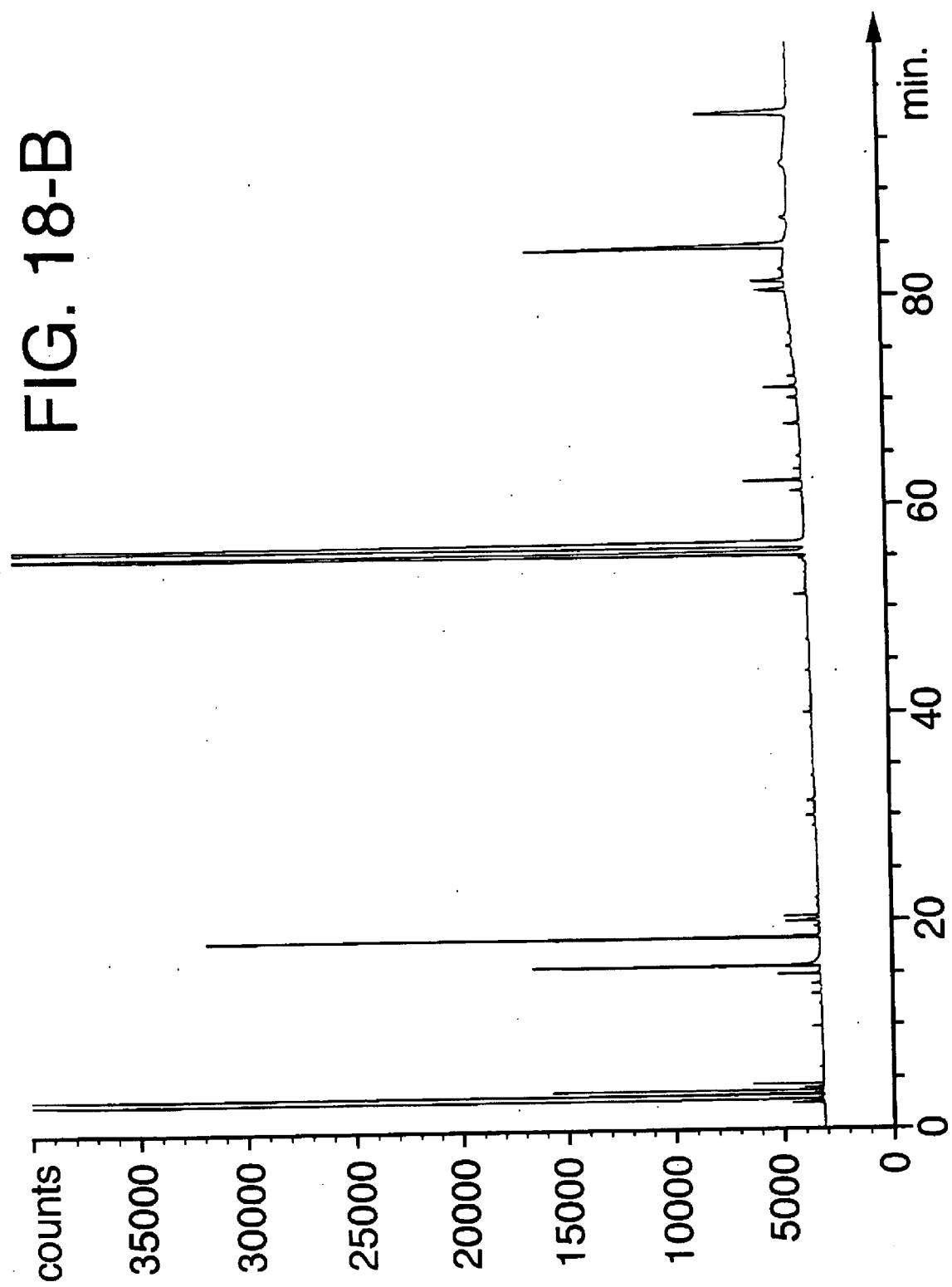

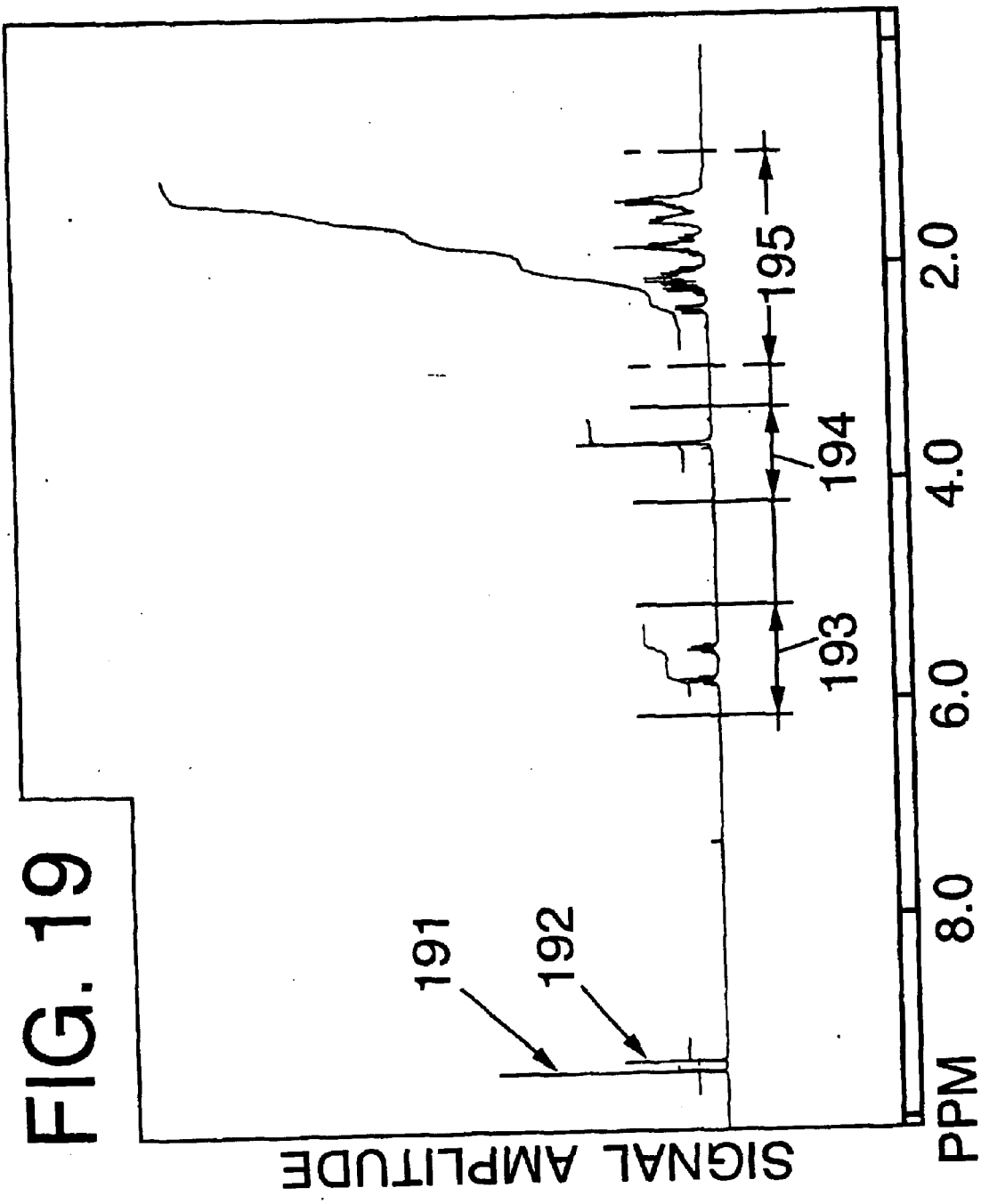

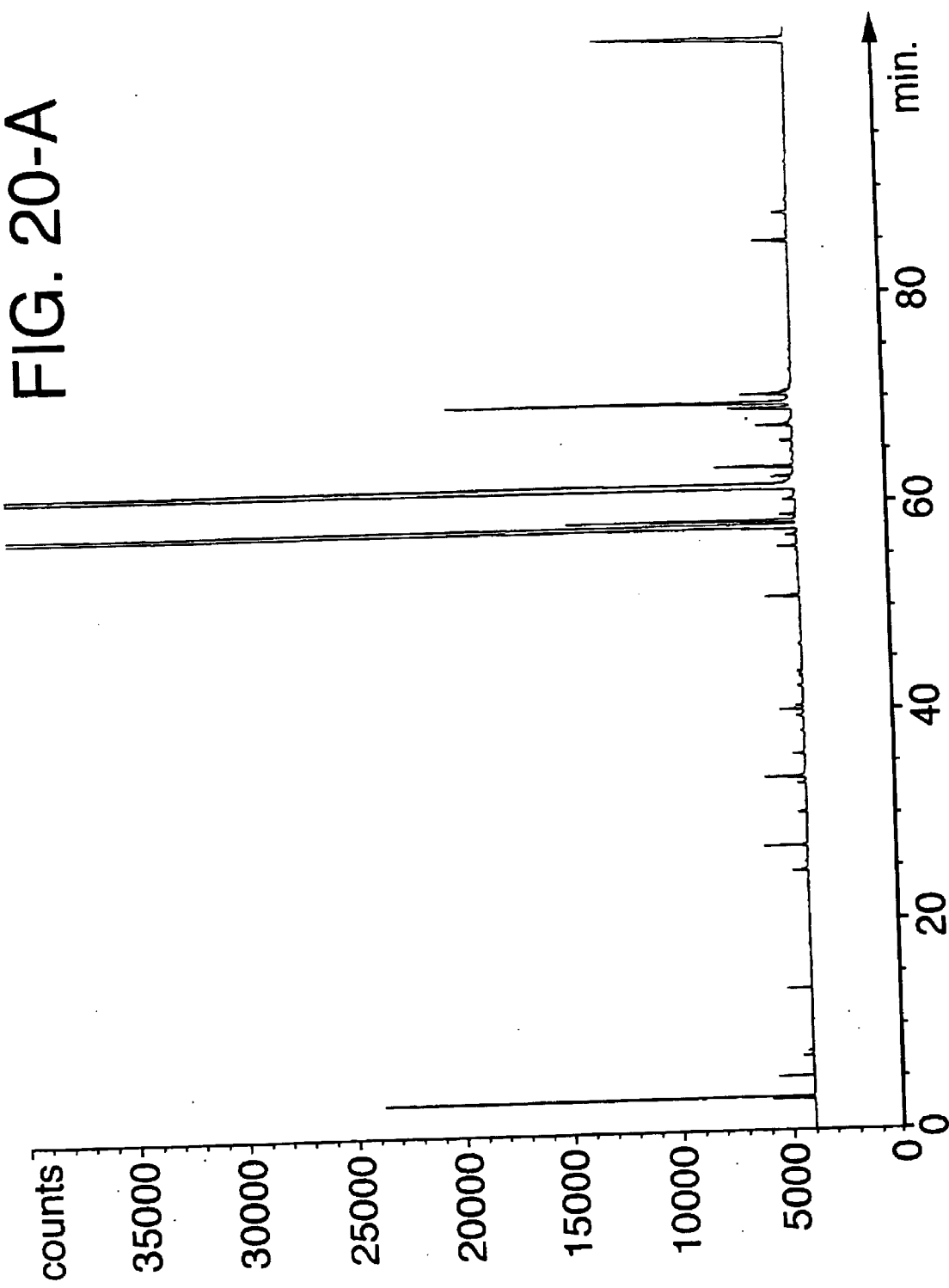

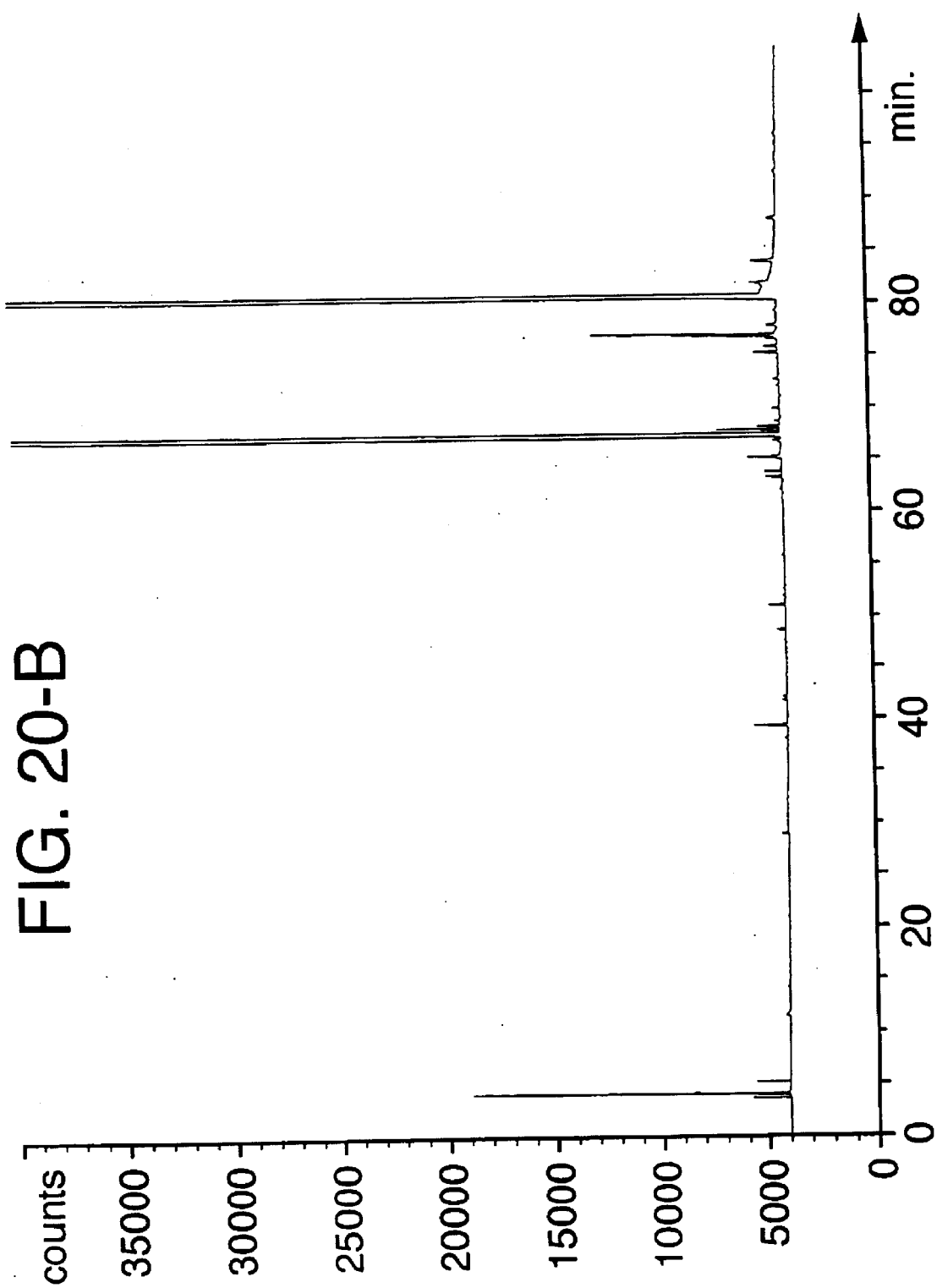
FIG. 20-B

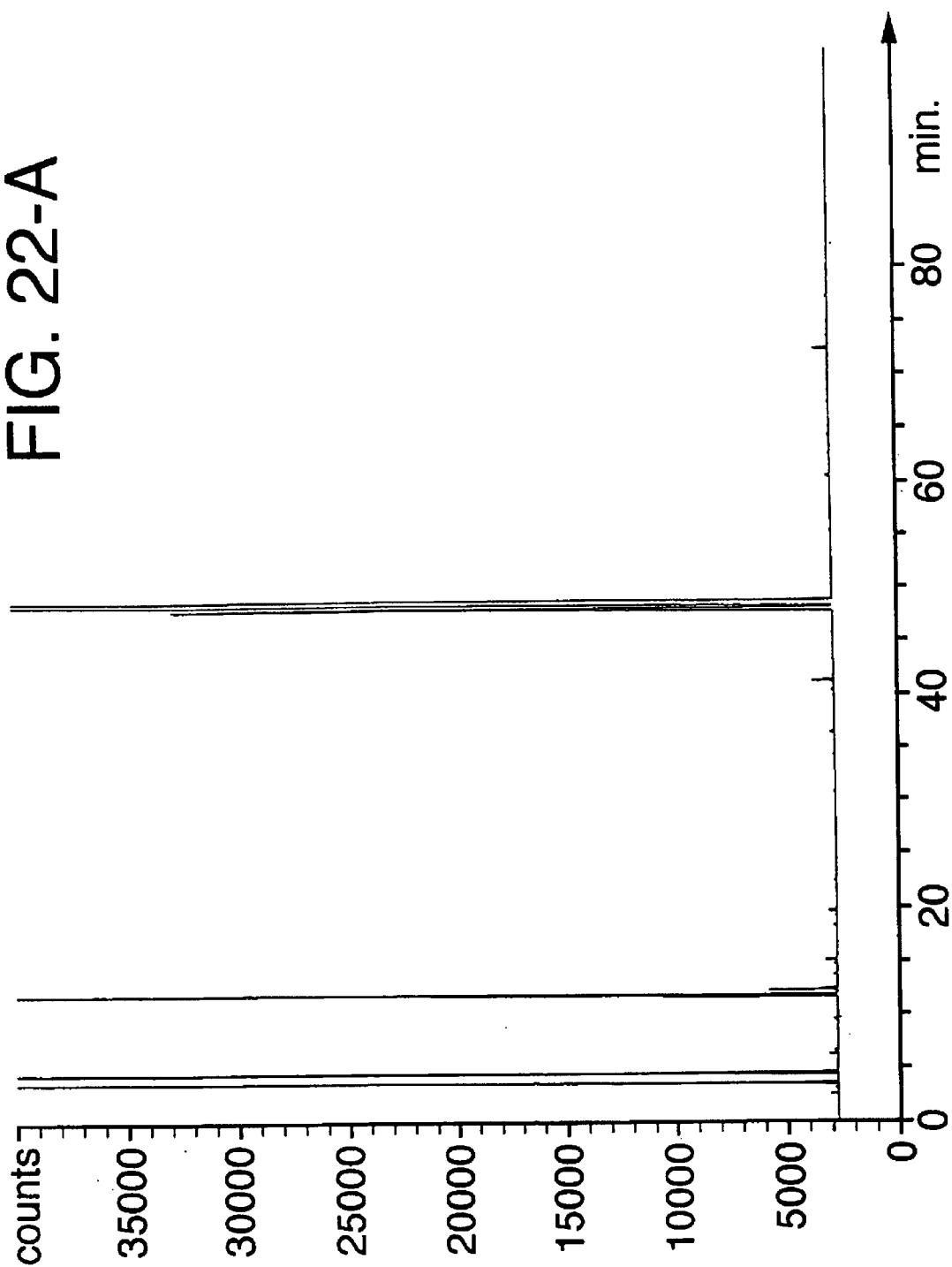

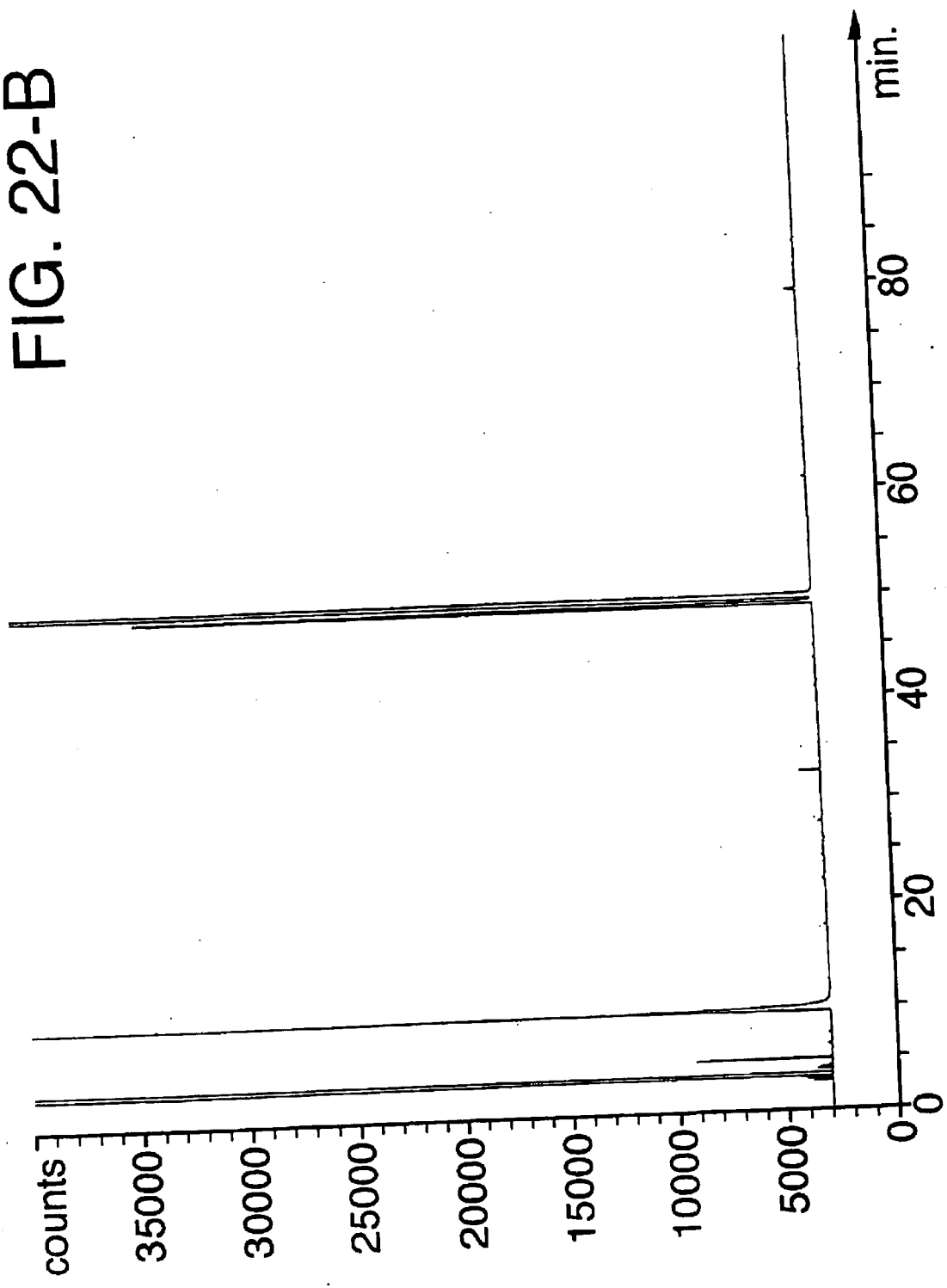
FIG. 22-B

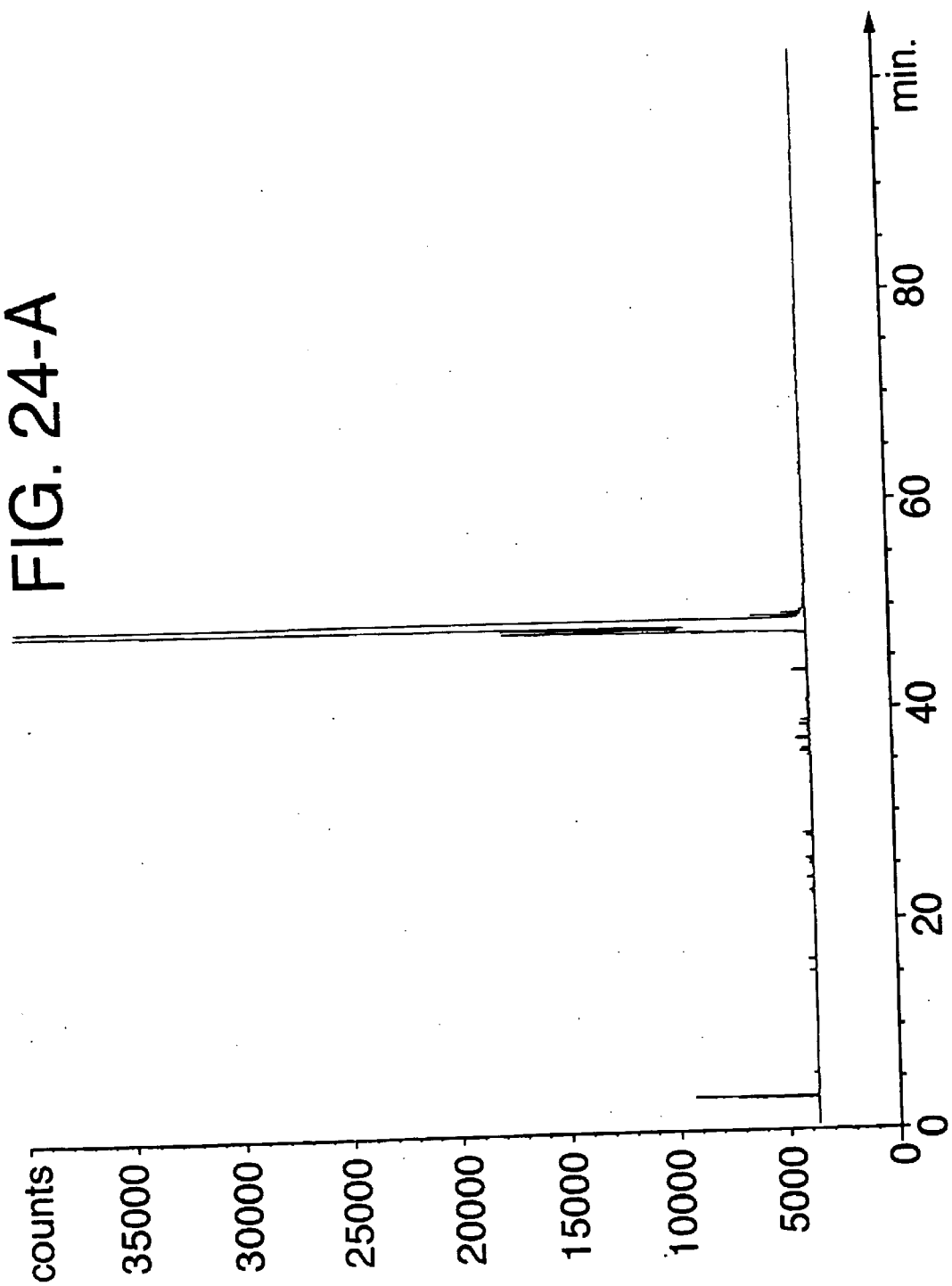
FIG. 24-A

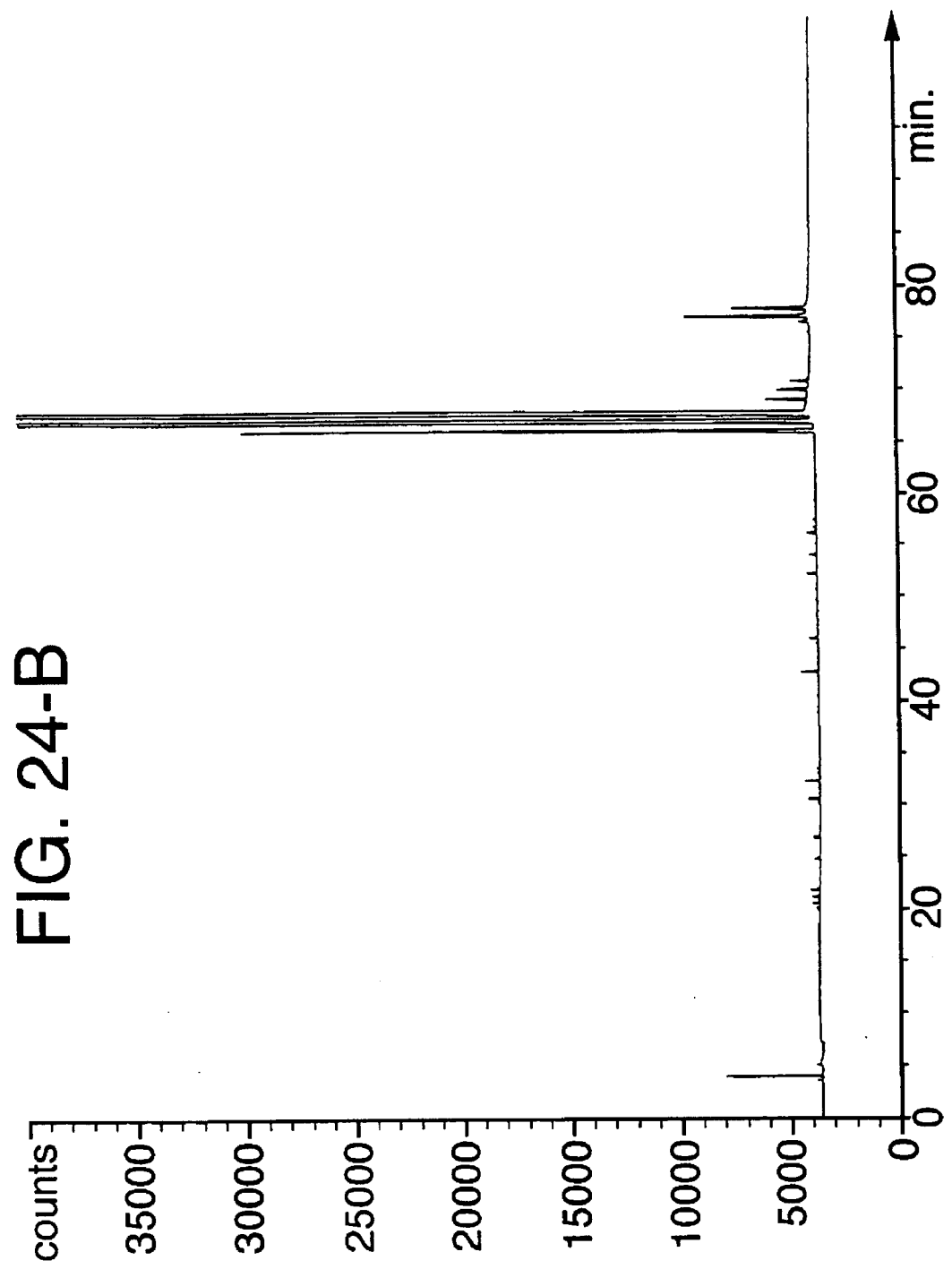
FIG. 24-B

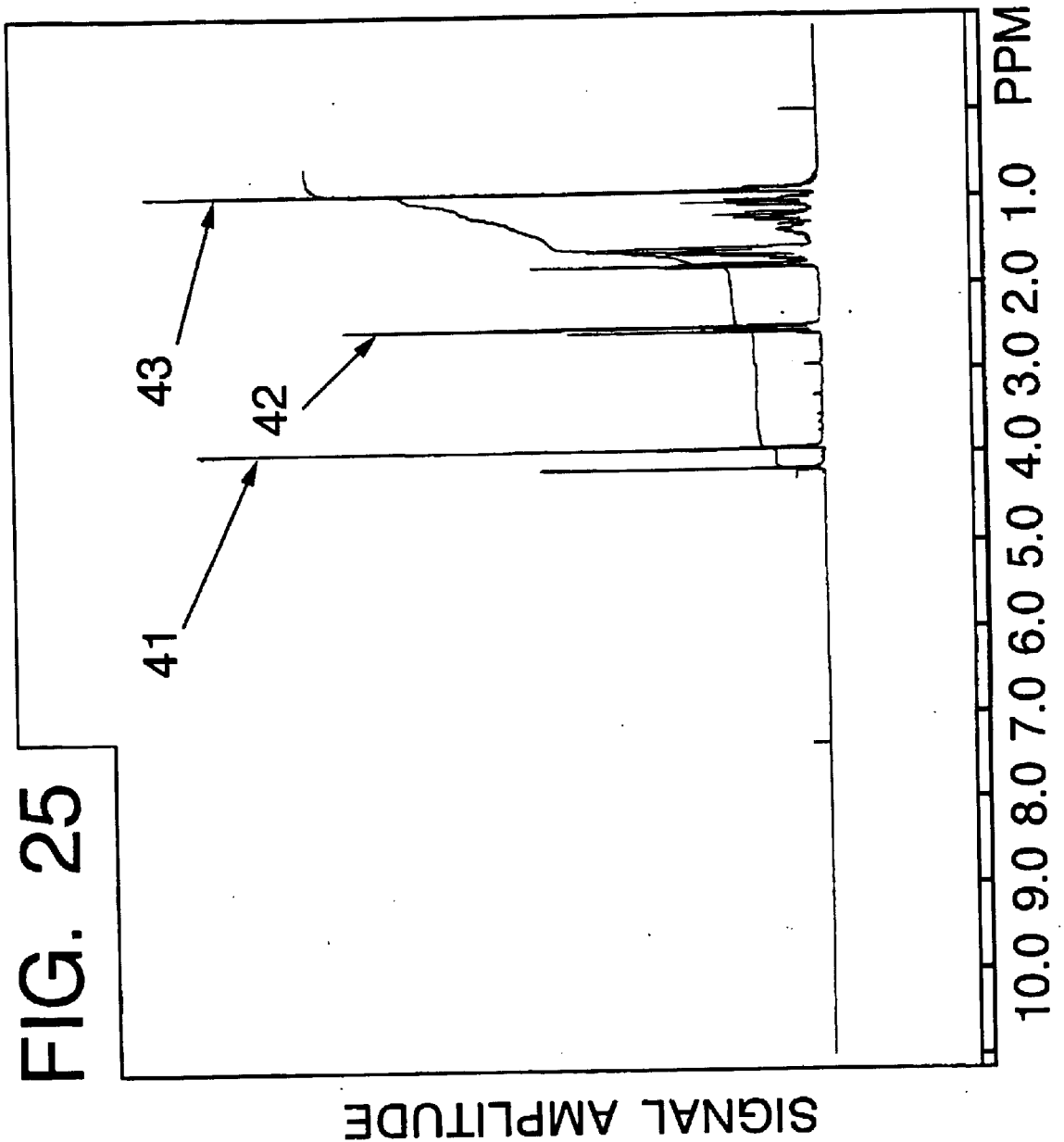

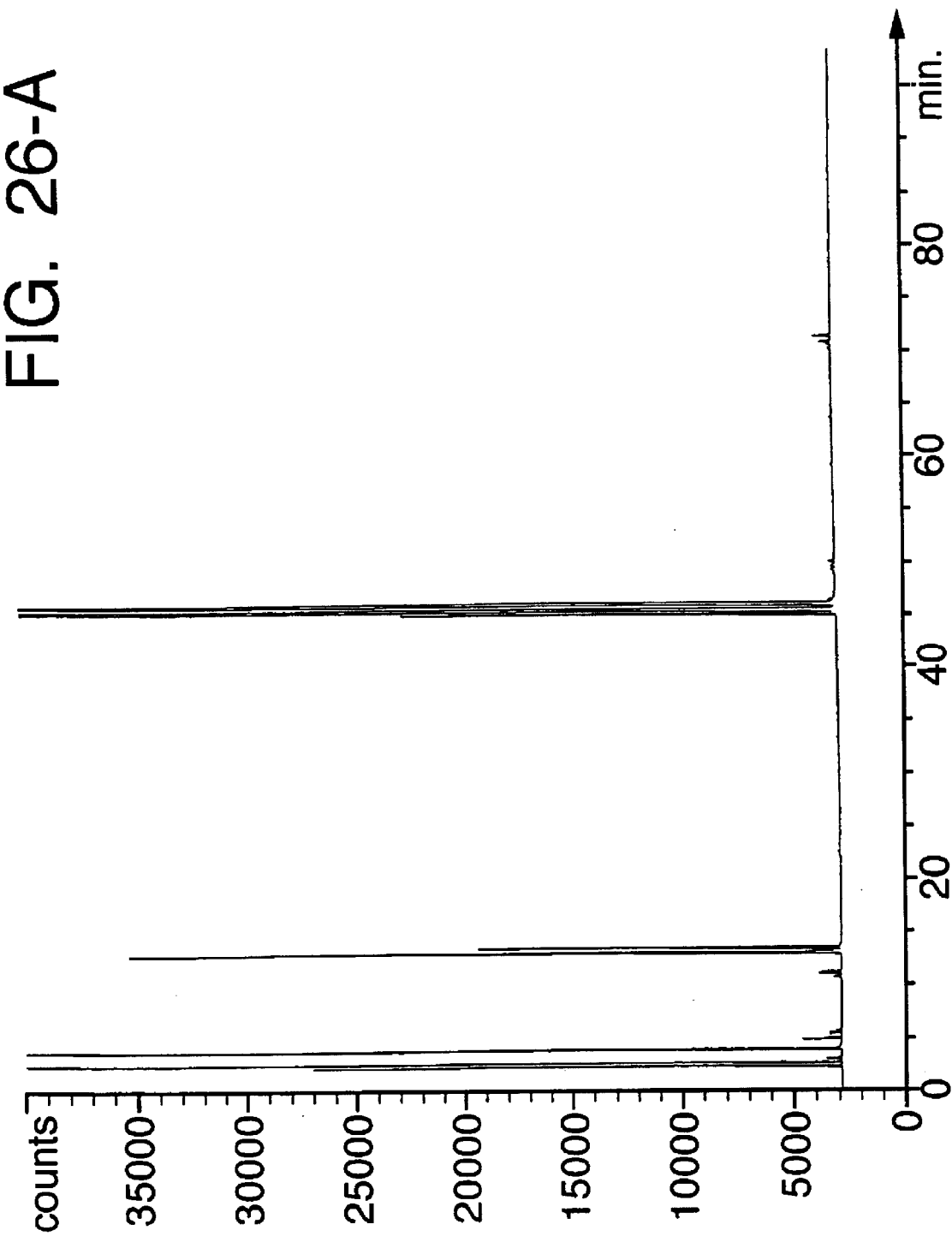
FIG. 26-A

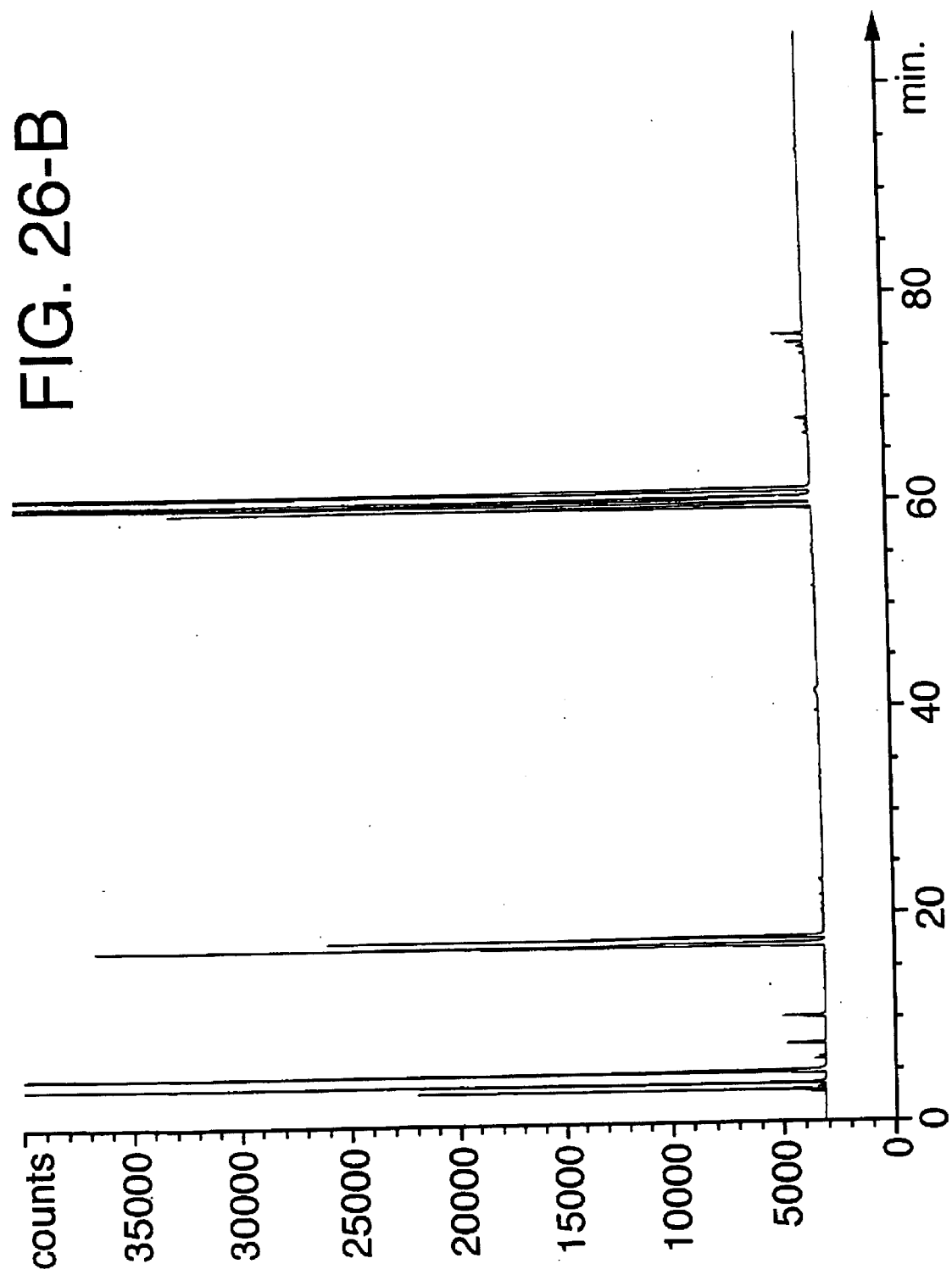

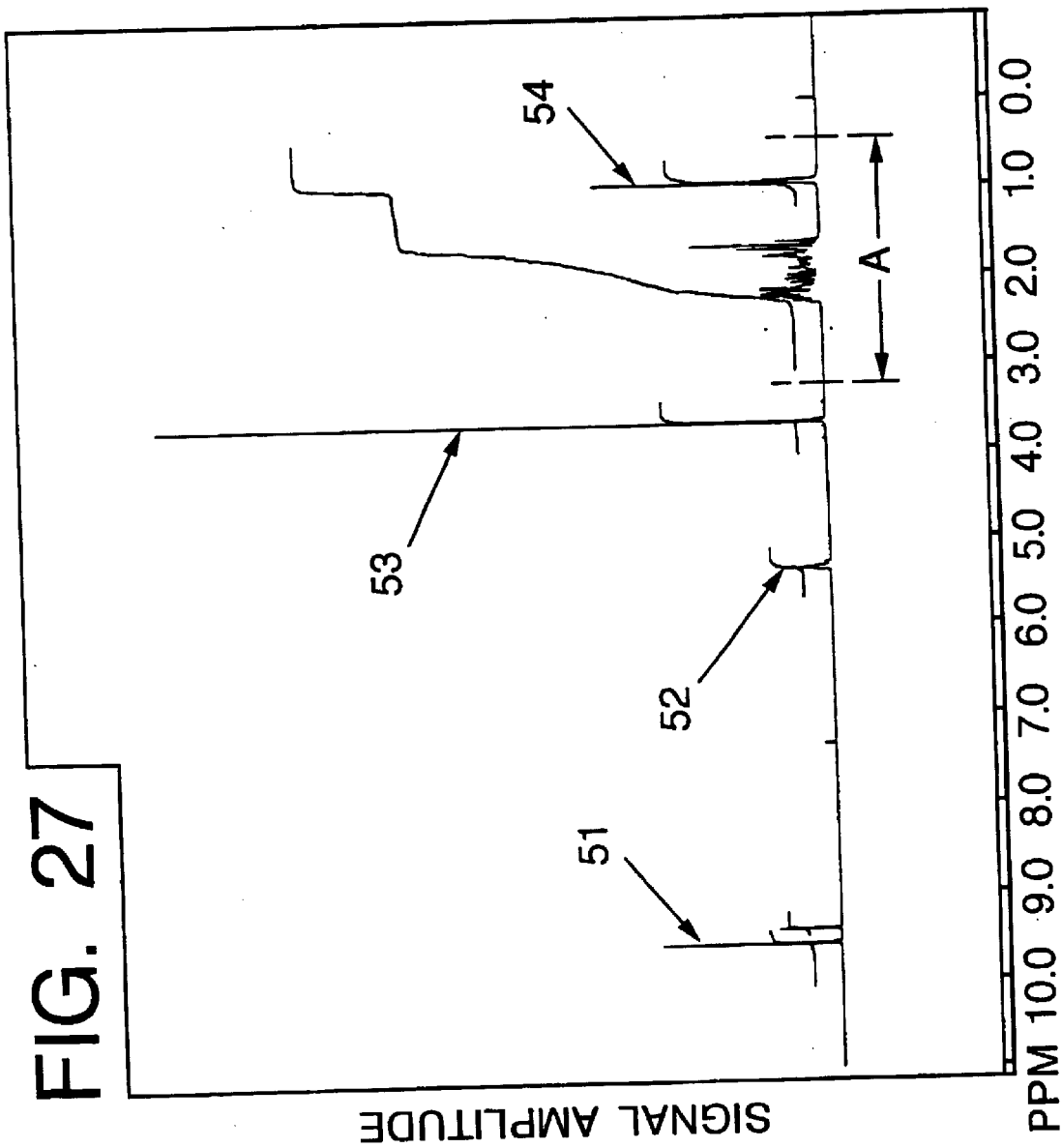

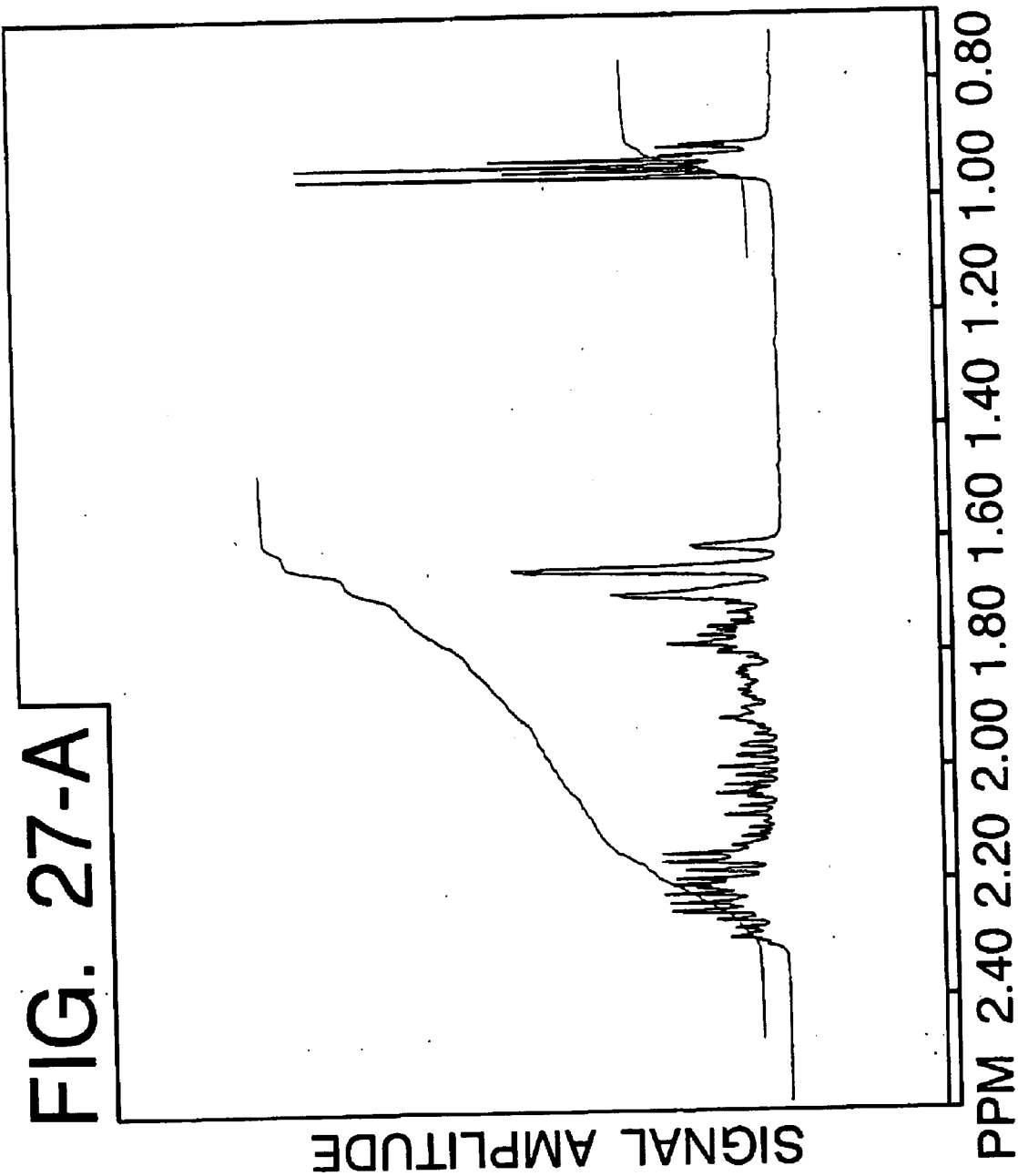
FIG. 27-A

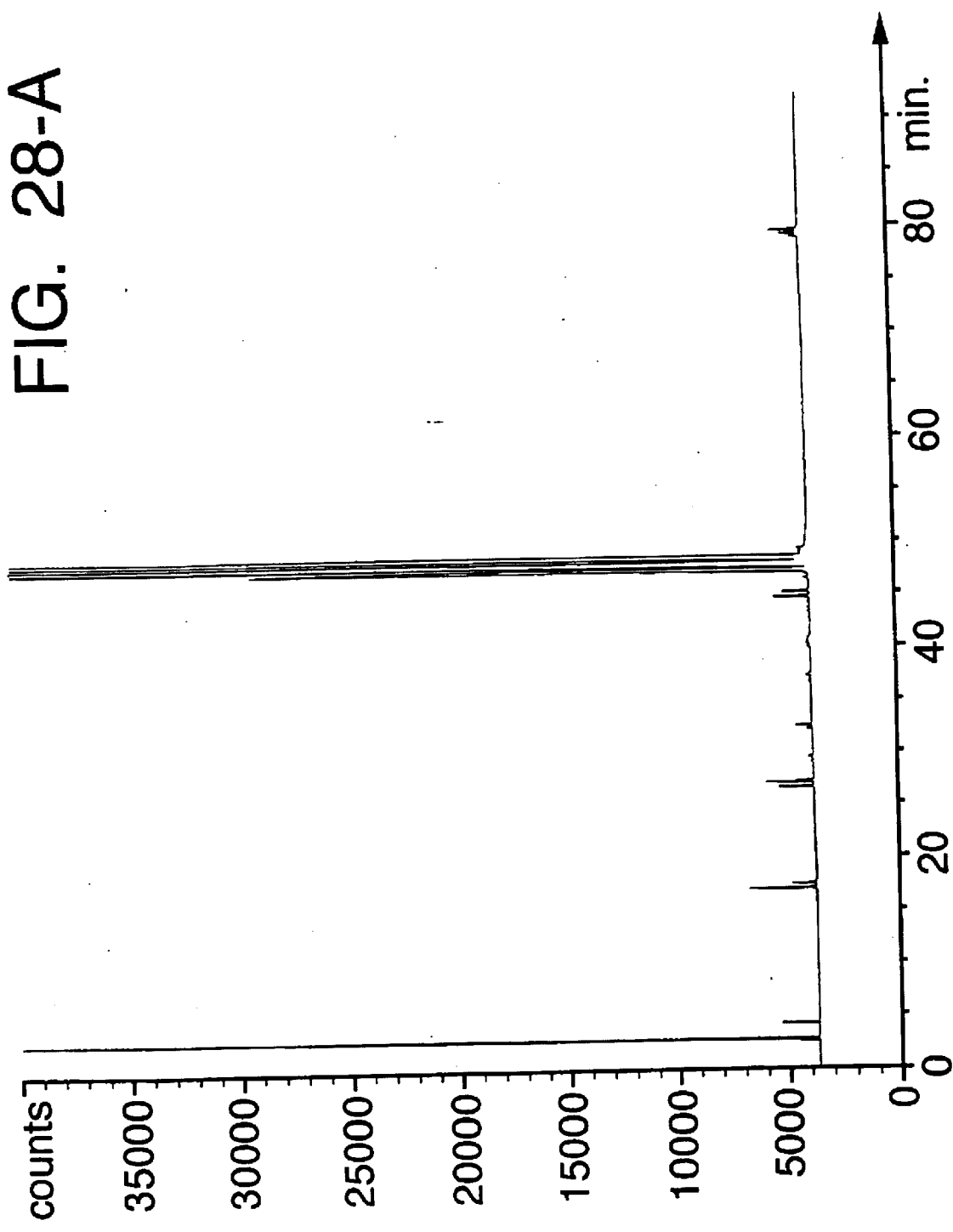
FIG. 28-A

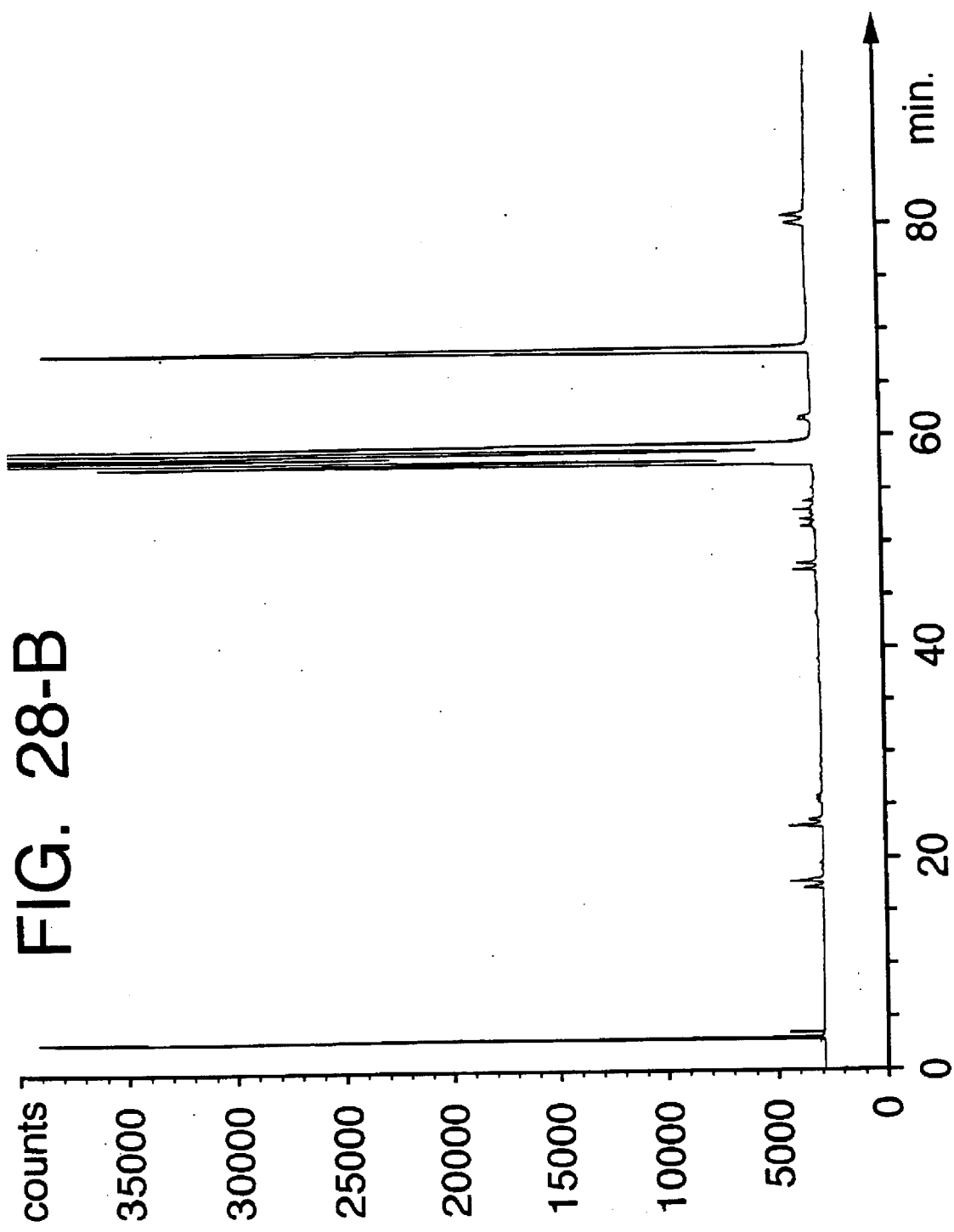
FIG. 28-B

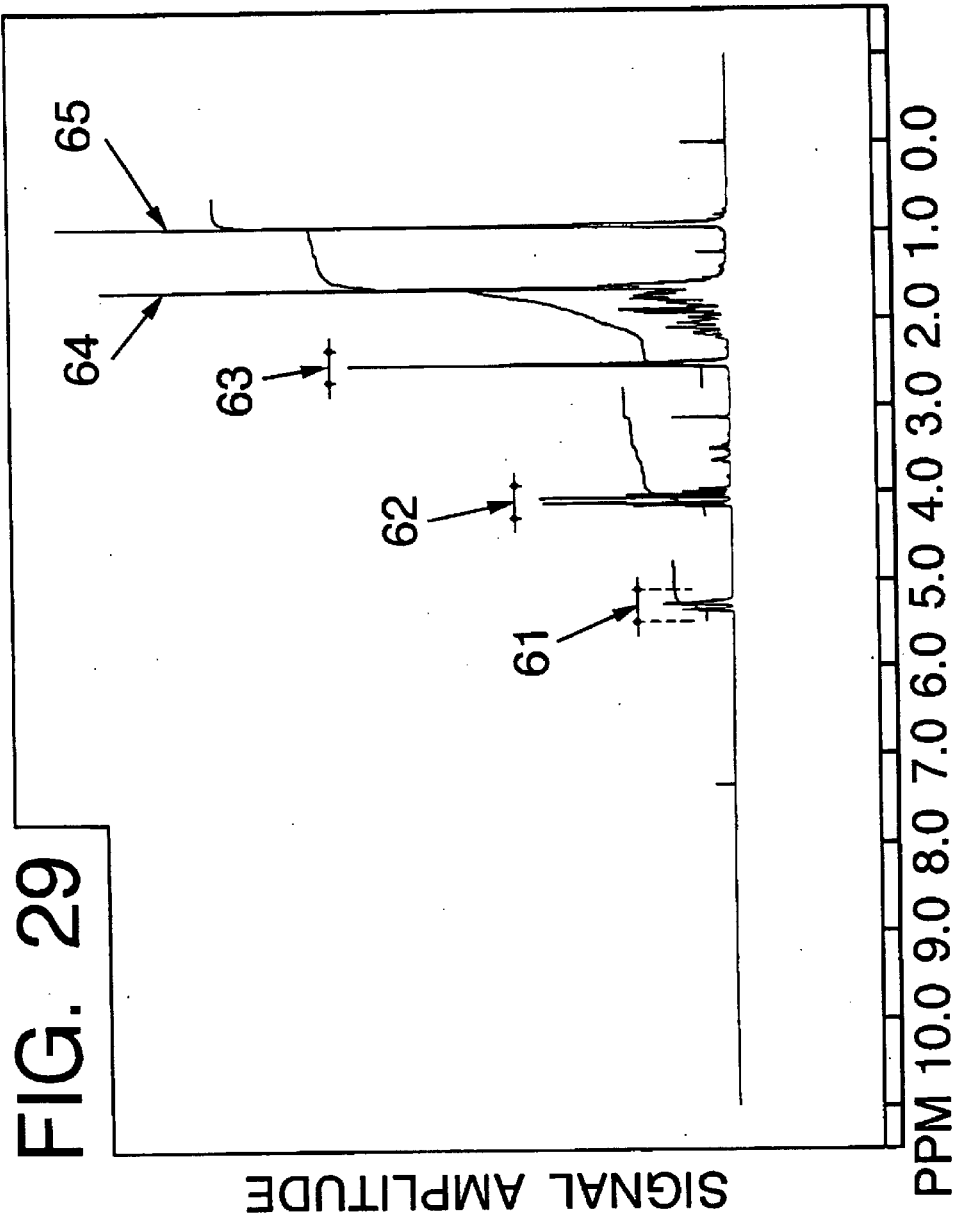

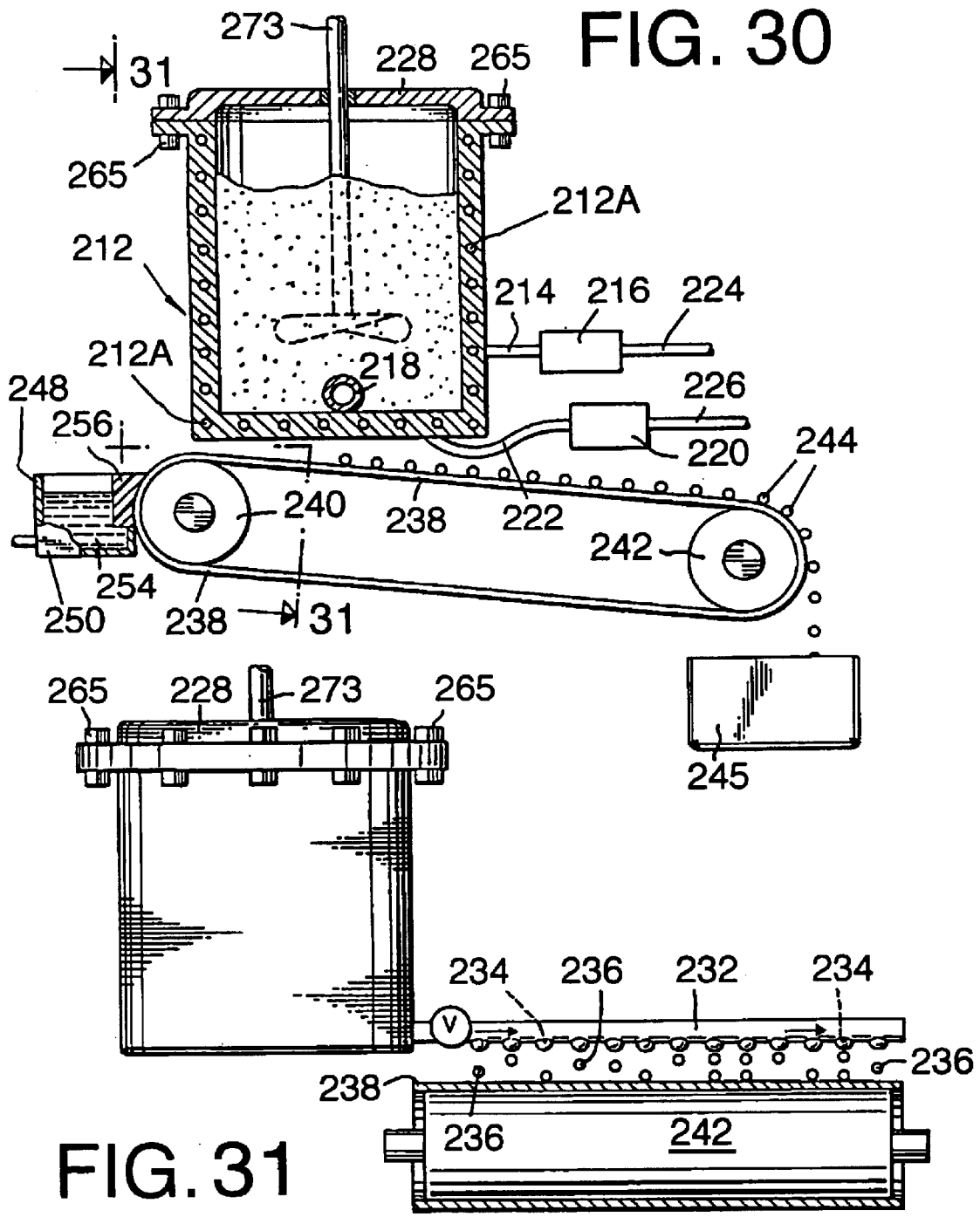

BICYCLE LACTONES, PERFUMERY USES THEREOF, PROCESSES FOR PREPARING SAME AND INTERMEDIATES THEREFOR

STATUS OF RELATED APPLICATIONS

This application is a divisional application of U.S. Ser. No. 10/210,386 filed on Aug. 1, 2002 now U.S. Pat. No. 6,608,010, which is a divisional of U.S. Ser. No. 09/709,109 filed on Nov. 10, 2000, which issued as U.S. Pat. No. 6,462,015 on Oct. 8, 2002, the contents hereby incorporated by reference as if set forth in its entirety.

BACKGROUND OF THE INVENTION

Our invention relates to bicyclic lactones, which are fused ring lactones and spiro lactones, perfumery uses thereof, syntheses for preparing same and intermediates employed in carrying out these syntheses.

Perfume compositions, perfumed articles, colognes and perfumed polymers, which have sweet, fruity, nutty, hay-like, coumarinic, tonka, tobacco, lactonic, green, tagette, woody, earthy, ambery, orris, coconut, spicy and cinnamon aromas with "cooling" nuances and with nutty, hay-like, orris, woody and coumarinic topnotes and woody, jasmine, floral, nutty, lactonic, spicy and cinnamon undertones, are highly desirable in the art of perfumery. Presently, natural and synthetic substances, which emit such aromas, nuances, topnotes and undertones, are high in cost, complex in nature (requiring multiple components in order to yield such aromas, nuances, topnotes and undertones) and, in general, difficult to obtain.

Coumarin having the structure:

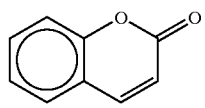

and hexahydrocoumarin having the structure:

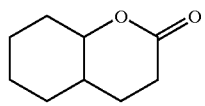

are well known in the art of perfumery. Although the chemical structures of coumarin and hexahydrocoumarin resemble a number of the bicyclic lactones of our invention, each of the bicyclic lactones of our invention has unexpected, unobvious and advantageous organoleptic properties and biological properties related thereto when compared to the hexahydrocoumarin and coumarin of the prior art.

BRIEF DESCRIPTION OF THE DRAWINGS

FIG. 1A is a GC capillary survey of the reaction product of Example I(A) containing the compounds having the structures:

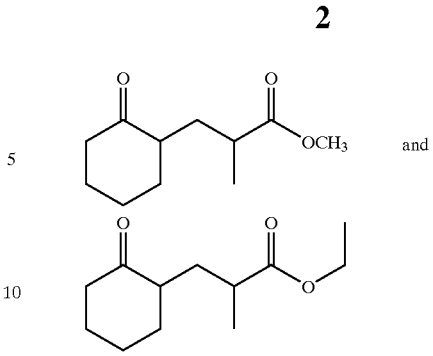

(conditions: 50 meter×0.32 mm methyl silicone column programmed from 75° C. up to 250° C. at 2° C. per minute).

FIG. 1B is a GC capillary survey of the reaction product of Example I(A) containing the compounds having the structures:

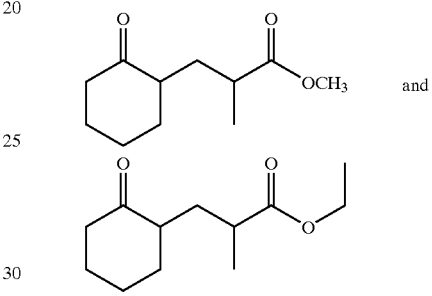

(conditions: 50 meter×0.32 mm CARBOWAX® 20M column programmed from 75° C. up to 250° C. at 2° C. per minute).

Figure 2:
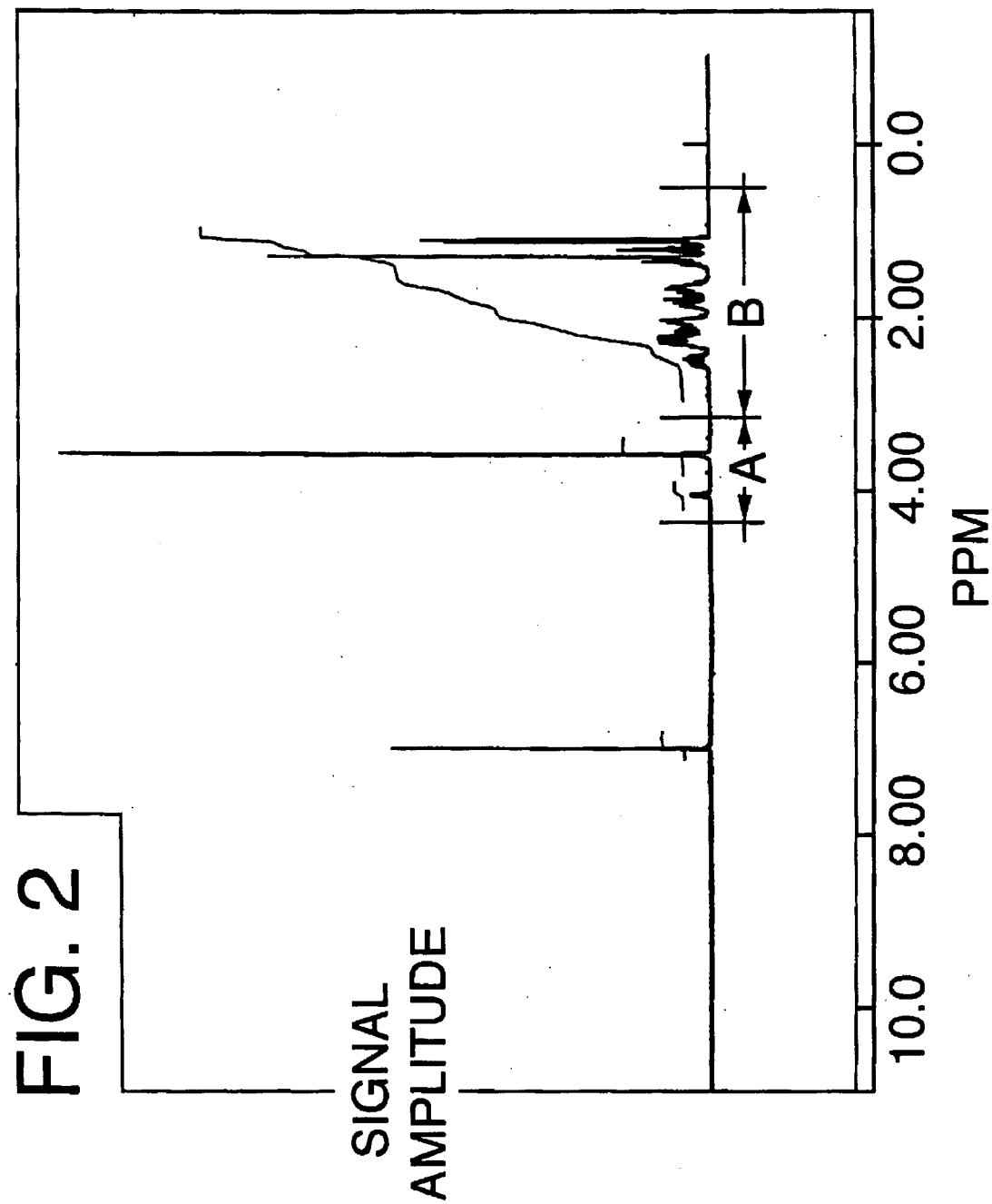

FIG. 2 is the NMR spectrum for the reaction product of Example I(A) containing the compounds having the structures:

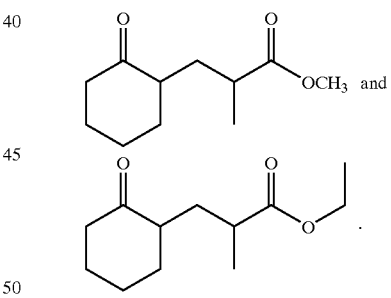

FIG. 2A is an enlargement of section "A" of the NMR spectrum of FIG. 2.

FIG. 2B is an enlargement of the section "B" of the NMR spectrum of FIG. 2.

FIGS. 3A-3B is a GC capillary survey for the compound having the structure:

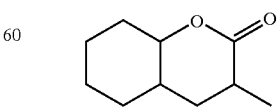

prepared according to Example I(B), which indicates a mixture of trans and cis isomers in a ratio of 44:56 with the trans isomer being shown by the structure:

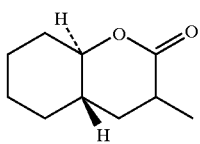

and the cis isomer being shown by the structure:

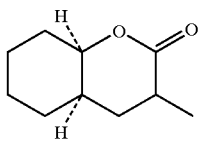

Figure 4:
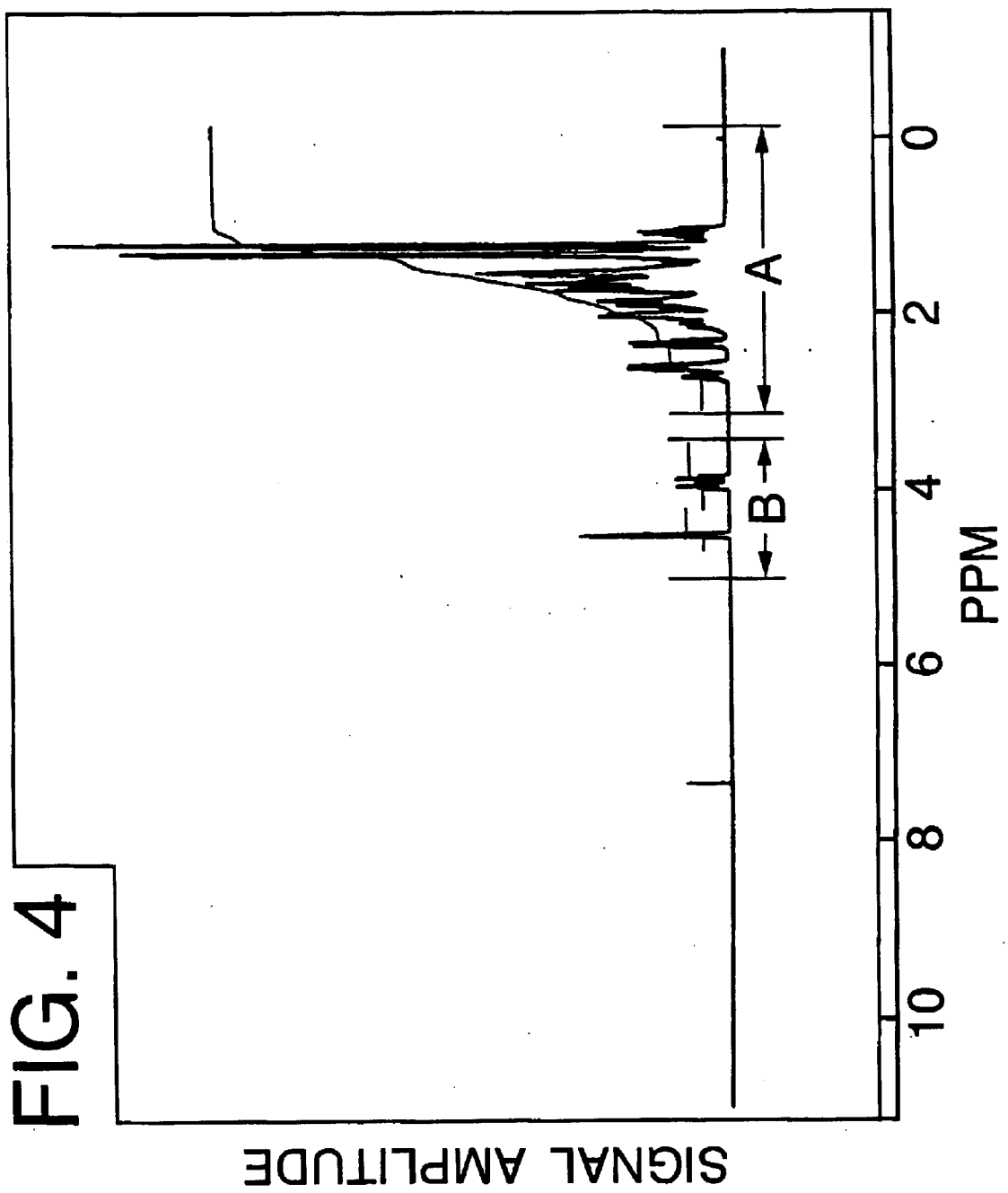

FIG. 4 is the NMR spectrum for the mixture of trans and cis isomers having the structures:

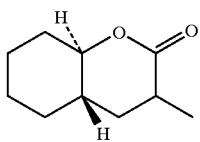 and 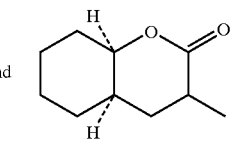

prepared according to Example I(B).

FIG. 4A is an enlargement of the section "A" of the NMR spectrum of FIG. 4.

FIG. 4B is an enlargement of the sections "B(1)" and "B(2)" of the NMR spectrum of FIG. 4, wherein the section "B(1)" is for the trans isomer having the structure:

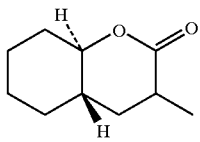

and the section "B(2)" is for the cis isomer having the structure:

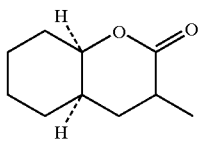

FIG. 5 is the infrared spectrum for the reaction product of Example I(B) containing a 44:56 weight ratio mixture of the trans isomer having the structure:

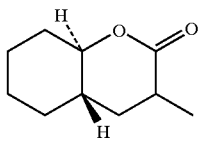

and the cis isomer having the structure:

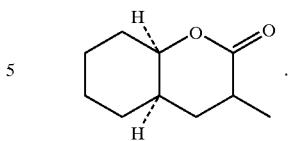

FIG. 6A is a GC capillary survey for the mixture of compounds having the structures:

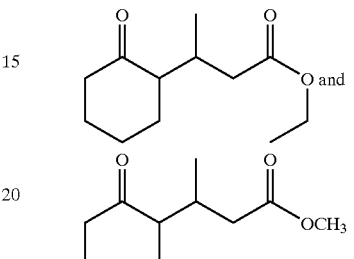

wherein the mole ratio of the compound having the structure:

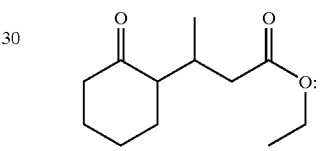

the compound having the structure:

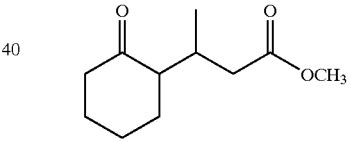

is 23:77 (conditions: 50 meter×0.32 mm methyl silicone column programmed from 75° C. up to 250° C. at 2° C. per minute).

FIG. 6B is a GC capillary survey the mixture of compounds having the structures:

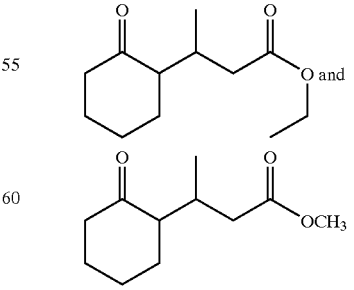

prepared according to Example II(A) containing a mixture of compounds having the structures:

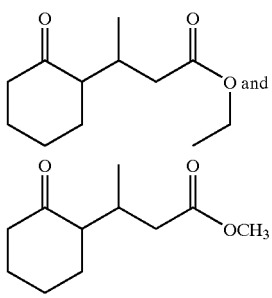

in a 23:77 weight ratio.

Figure 7:
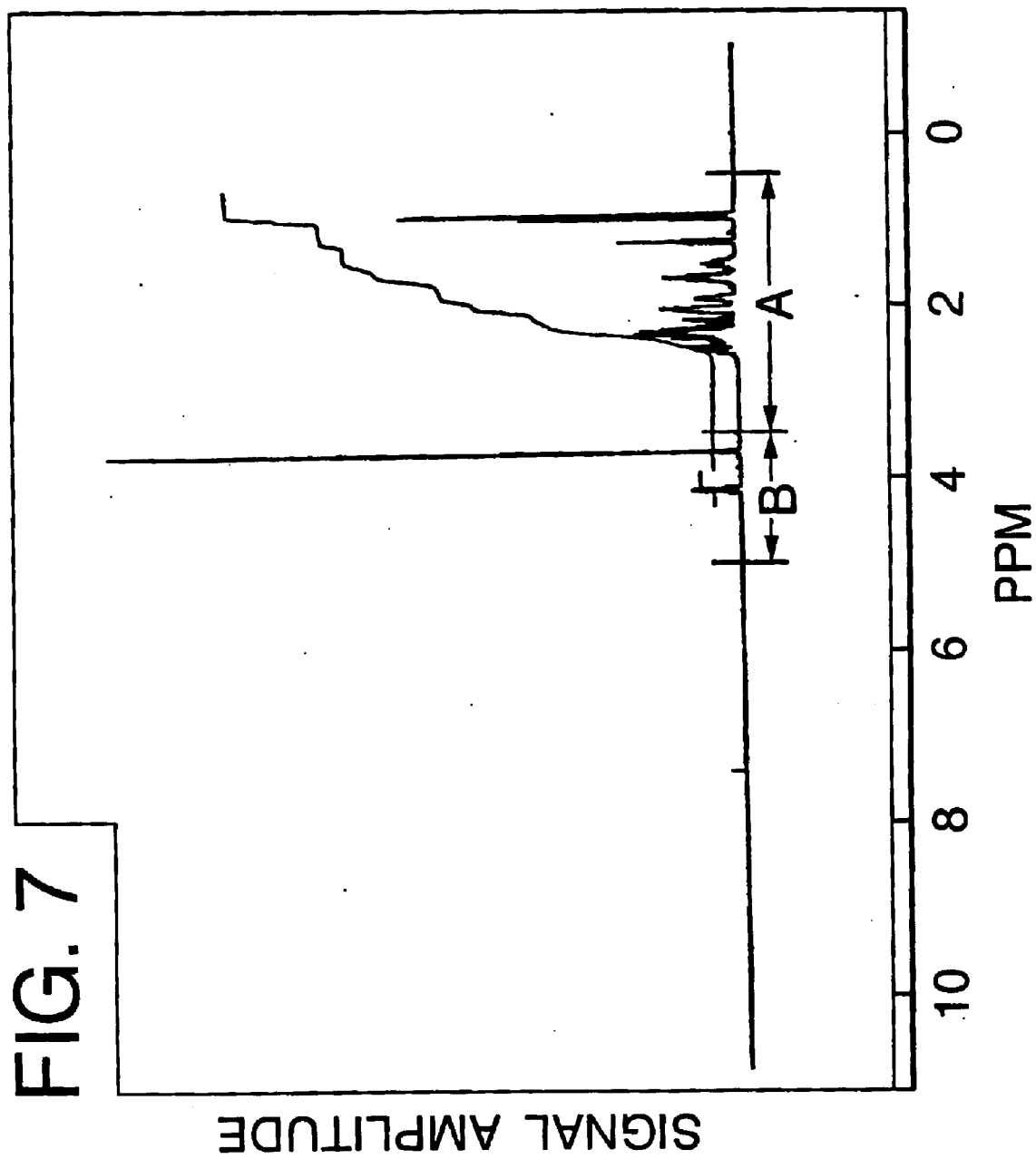

FIG. 7 is the NMR spectrum for the mixture of compounds having the structures:

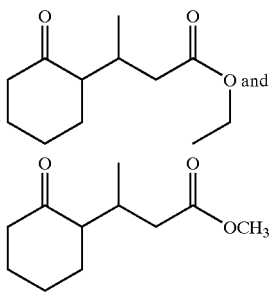

prepared according to Example II(A).

FIG. 7A is an enlargement of section "A" of the NMR spectrum of FIG. 7.

FIG. 7B is an enlargement of section "B(1)" and "B(2)" of the NMR spectrum of FIG. 7. Section "B(1)" is for the methyl ester having the structure:

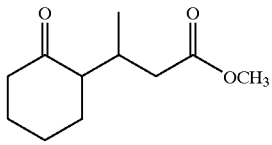

and section "B(2)" is for the ethyl ester having the structure:

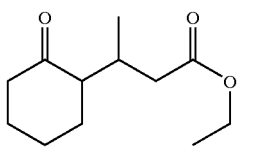

prepared according to Example II(A).

FIG. 8 is the infrared spectrum for the mixture of compounds having the structures:

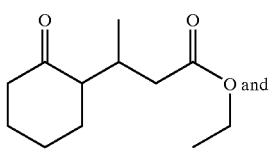

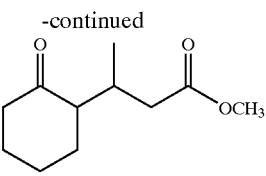

prepared according to Example II(A).

FIG. 9A is a GC capillary survey for the compound having the structure:

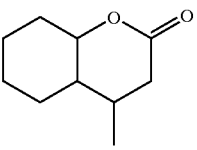

prepared according to Example II(B) (conditions: 50 meter× 0.32 mm methyl silicone column programmed from 75° C. up to 250° C. at 2° C. per minute).

FIG. 9B is GC capillary survey for the reaction product of Example II(B) containing the compound having the structure:

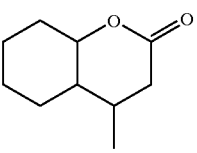

(conditions: 50 meter×0.32 mm CARBOWAX® 20M column programmed from 75° C. up to 250° C. at 2° C. per minute).

Figure 10:
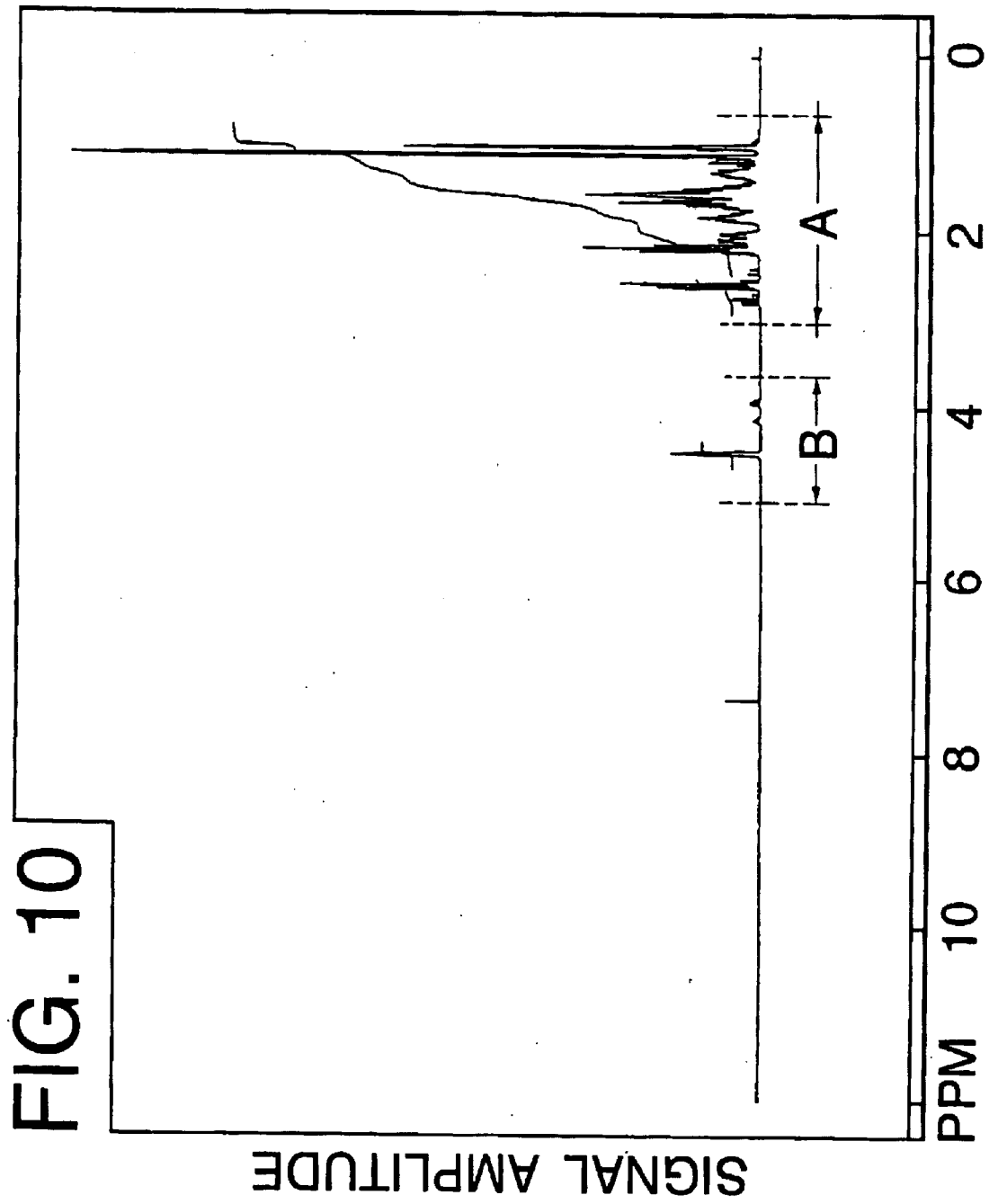

FIG. 10 is the NMR spectrum for the compound having the structure:

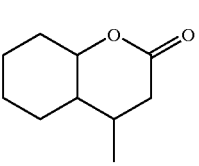

prepared according to Example II(B).

FIG. 10A is an enlargement of the section "A" of the NMR spectrum of FIG. 10.

FIG. 10B is an enlargement of the section "B" of the NMR spectrum of FIG. 10.

Figure 11:
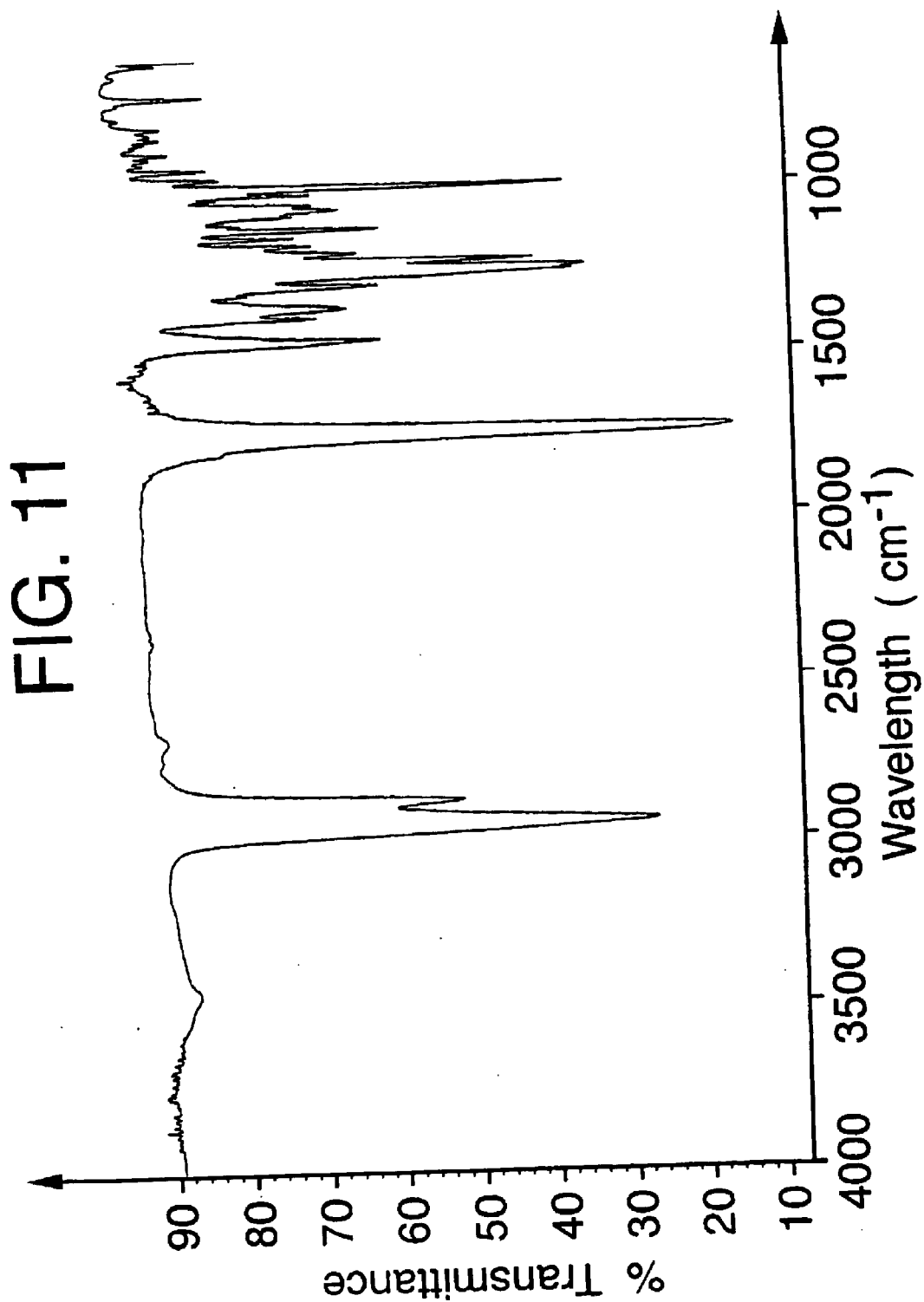

FIG. 11 is the infrared spectrum for the reaction product of Example II(B) containing the compound having the structure:

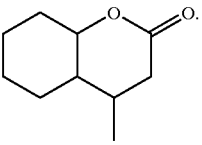

FIG. 12A is a GC profile for the reaction product of Example III(A) containing the compounds having the structures:

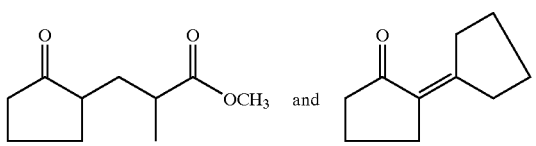

(conditions: 50 meter×0.32 mm methyl silicone column programmed from 75° C. up to 250° C. at 2° C. per minute).

FIG. 12B is a GC profile for the reaction product of Example III(A) containing the compounds having the structures:

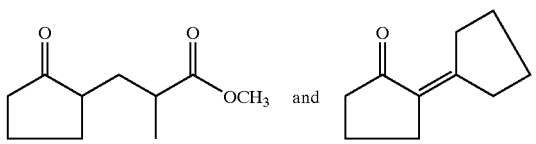

(conditions: 50 meter×0.32 mm CARBOWAX® 20M column programmed from 75° C. up to 250° C. at 2° C. per minute).

Figure 13:
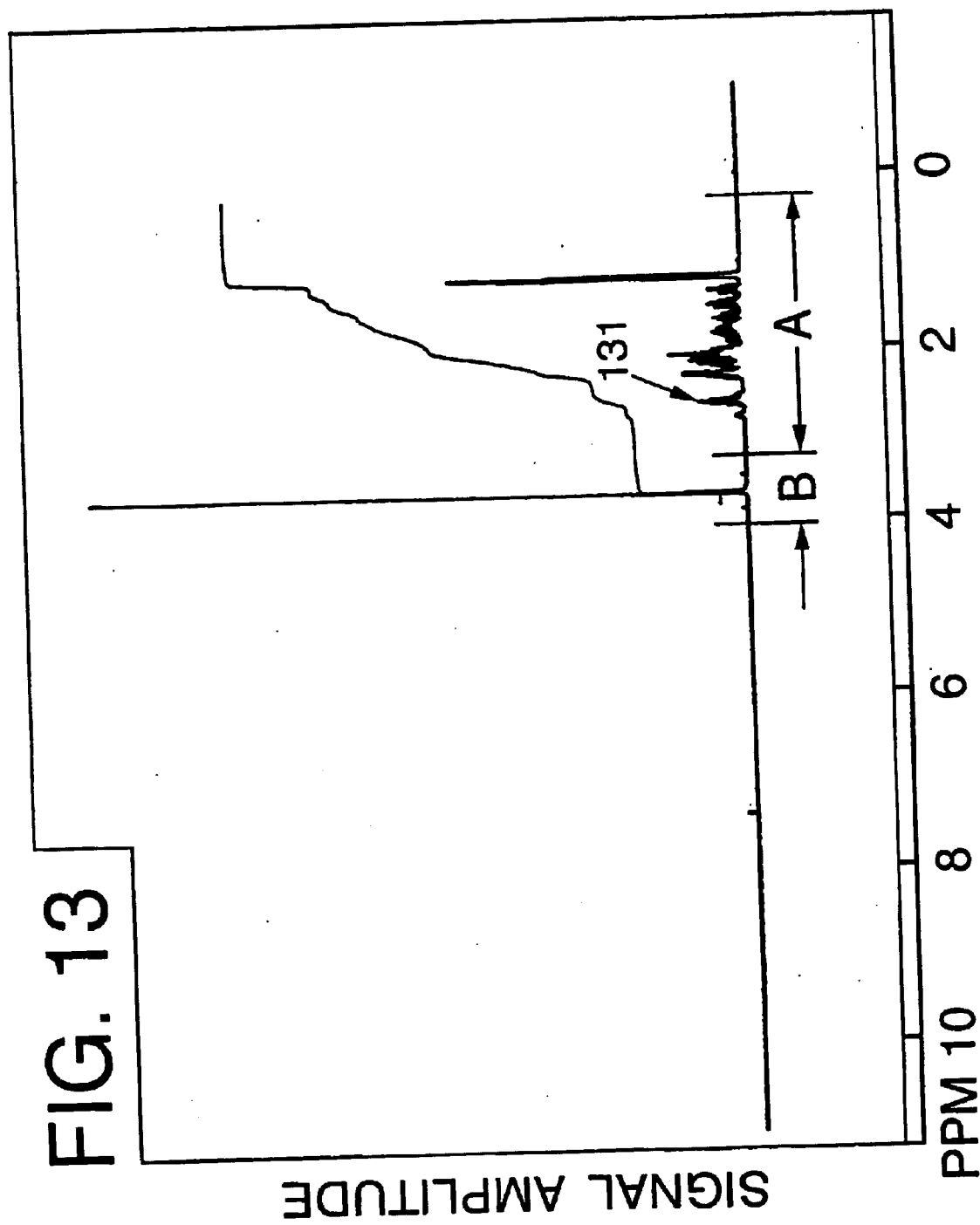

FIG. 13 is an NMR spectrum for the mixture of compounds having the structures:

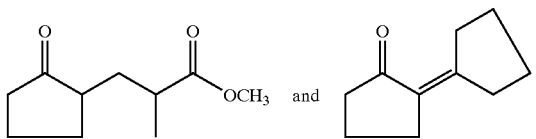

prepared according to Example III(A).

FIG. 13A is an enlargement of section "A" of the NMR spectrum of FIG. 13.

FIG. 13B is an enlargement of section "B" of the NMR spectrum of FIG. 13.

FIG. 14 is the infrared spectrum for the mixture of compounds having the structures:

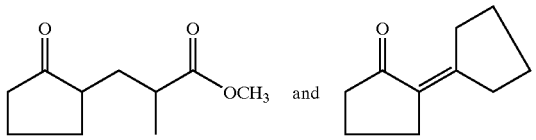

prepared according to Example III(A).

FIG. 15A is a GC profile for the reaction product of Example III(B) containing the compounds having the structures:

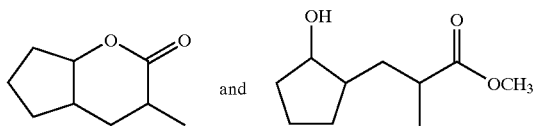

(conditions: 50 meter×0.32 mm methyl silicone column programmed from 75° C. up to 250° C. at 2° C. per minute).

FIG. 15B is a is a GC profile for the reaction product of Example III(B) containing the compounds having the structures:

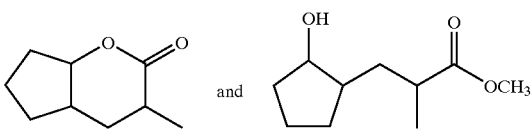

(conditions: 50 meter×0.32 mm CARBOWAX® 20M column programmed from 75° C. up to 250° C. at 2° C. per minute).

Figure 16:
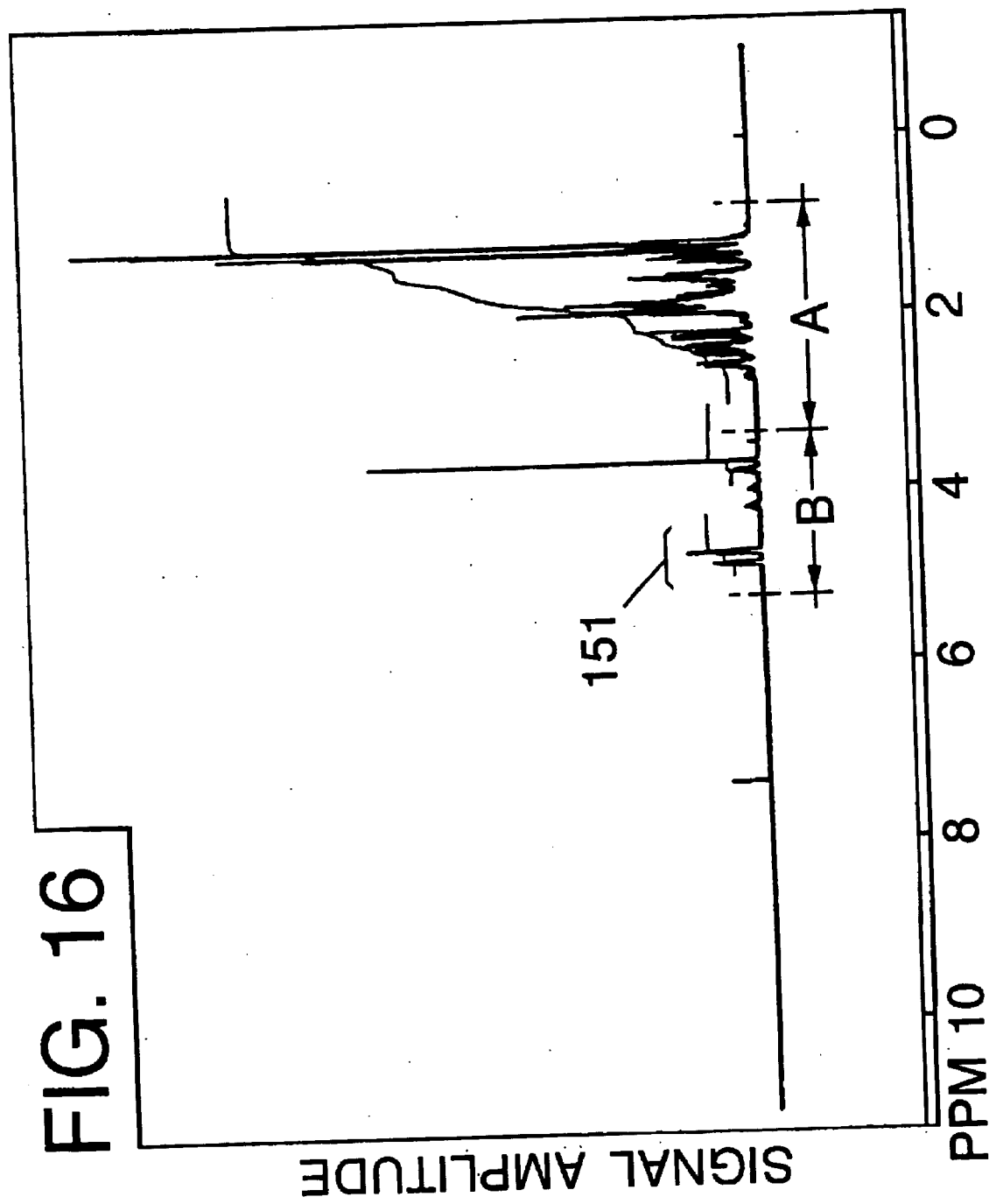

FIG. 16 is the NMR spectrum for the reaction product of Example III(B) containing the compounds having the structures:

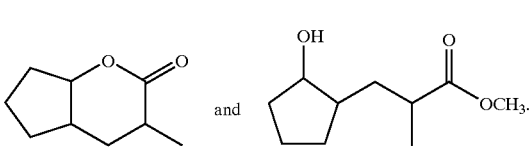

FIG. 16A is an enlargement of section "A" of the NMR spectrum of FIG. 16.

FIG. 16B is an enlargement of section "B" of the NMR spectrum of FIG. 16.

FIG. 17 is the infrared spectrum for the mixture of compounds having the structures:

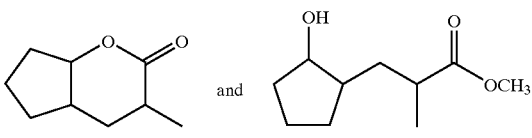

prepared according to Example III(B).

FIGS. 18A-18B is the GC profile for the reaction product of Example IV(A) containing the compounds having the structures:

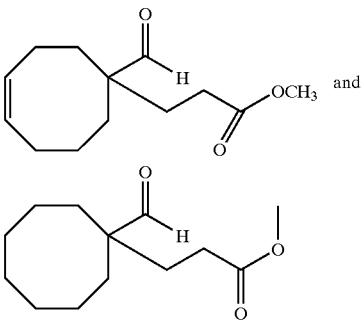

(conditions: 50 meter×0.32 mm methyl silicone column programmed from 75° C. up to 250° C. at 2° C. per minute).

FIG. 19 is the NMR spectrum for the mixture of compounds having the structures:

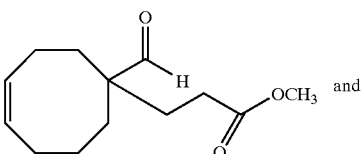

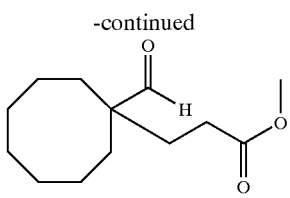

prepared according to Example IV(A).

FIG. 20A is a GC profile for the reaction product of Example IV(B) containing the compound having the structure:

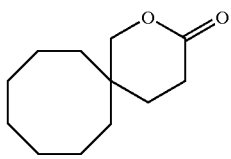

(conditions: 50 meter×0.32 mm methyl silicone column programmed from 75° C. up to 250° C. at 2° C. per minute).

FIG. 20B is a GC profile for the reaction product of Example IV(B) containing the compound having the structure:

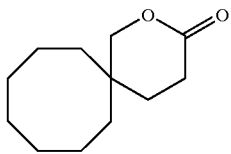

(conditions: 50 meter×0.32 mm CARBOWAX® 20M column programmed from 75° C. up to 250° C. at 2° C. per minute).

Figure 21:
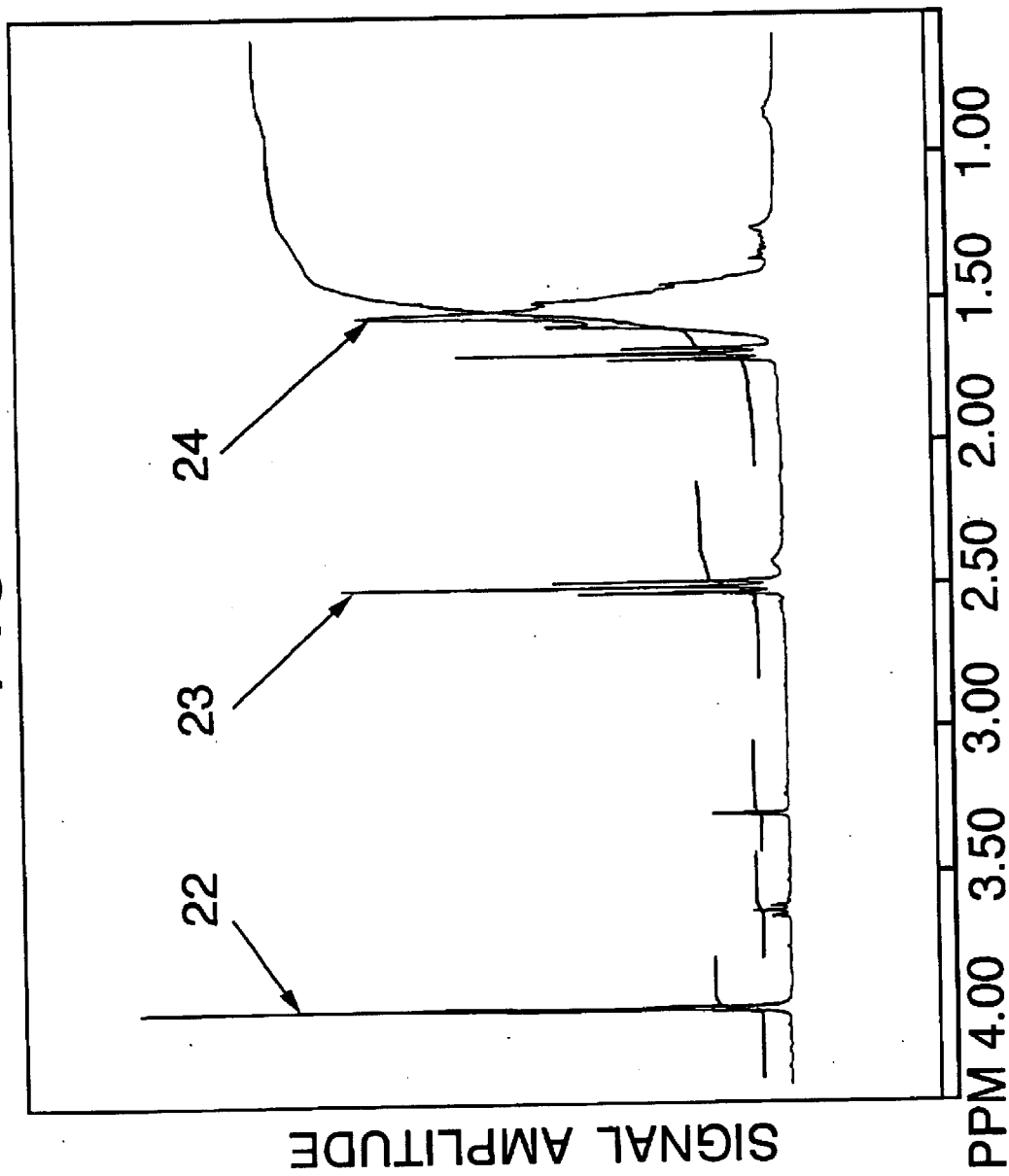

FIG. 21 is the NMR spectrum for the reaction product of Example IV(B) containing the compound having the structure:

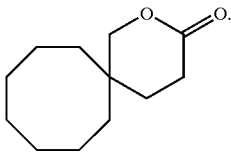

FIG. 22A is a GC profile for the reaction product of Example V(A) containing the compound having the structure:

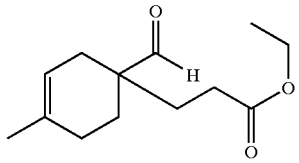

(conditions: 50 meter×0.32 mm methyl silicone column programmed from 75° C. up to 250° C. at 2° C. per minute).

FIG. 22B is a GC profile for the reaction product of Example V(A) containing the compound having the structure:

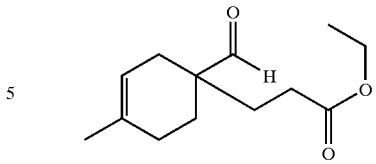

(conditions: 50 meter×0.32 mm CARBOWAX® 20M column programmed from 75° C. up to 250° C. at 2° C. per minute).

Figure 23:
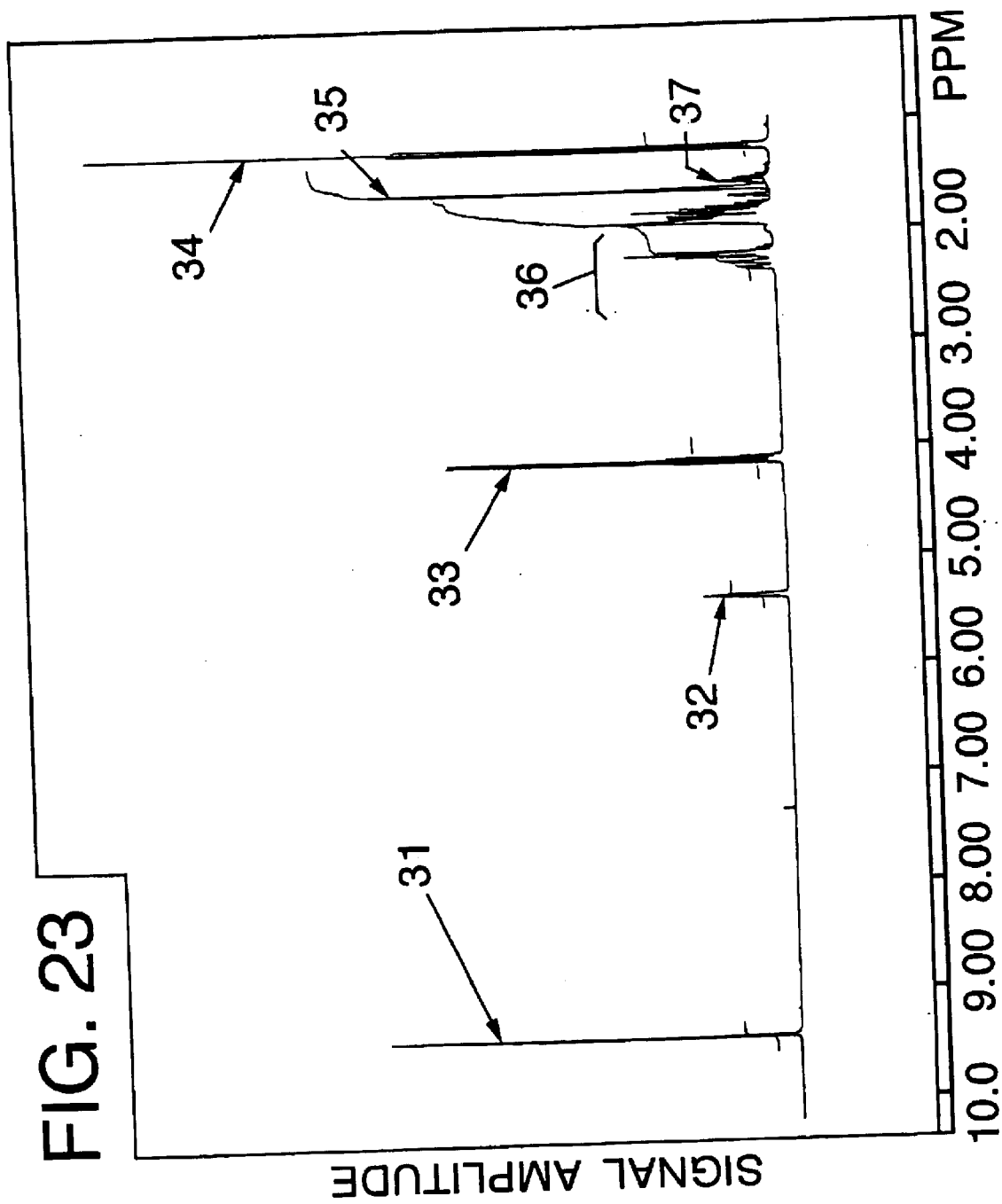

FIG. 23 is the NMR spectrum for the reaction product of Example V(A) containing the compound having the structure:

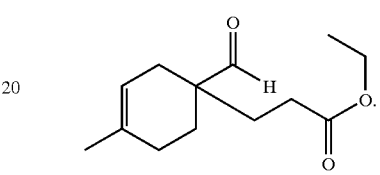

FIG. 24A is a GC profile for the reaction product of Example V(B) containing the compound having the structure:

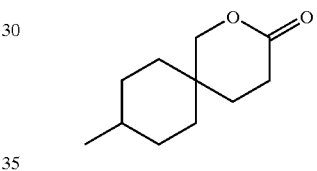

(conditions: 50 meter×0.32 mm methyl silicone column programmed from 75° C. up to 250° C. at 2° C. per minute).

FIG. 24B is a GC profile for the reaction product of Example V(B) containing the compound having the structure:

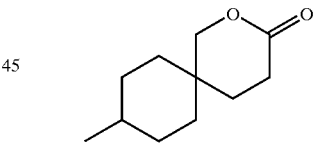

(conditions: 50 meter×0.32 mm CARBOWAX® 20M column programmed from 75° C. up to 250° C. at 2° C. per minute).

FIG. 25 is the NMR spectrum for the reaction product of Example V(B) containing the compound having the structure:

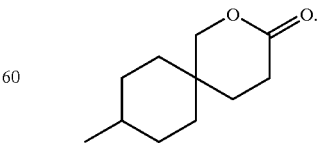

FIG. 26A is a GC profile for the reaction product of Example VI(A) containing the compound having the structure:

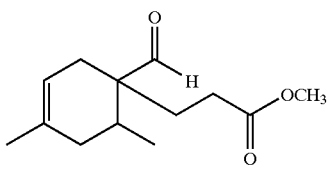

which is a 25:75 mixture of isomers having the structures:

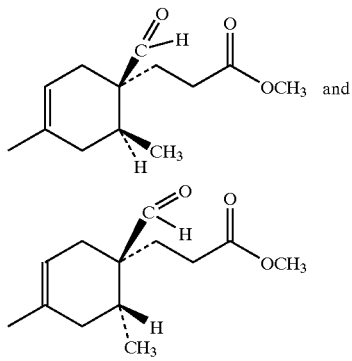

(conditions: 50 meter×0.32 mm methyl silicone column programmed from 75° C. up to 250° C. at 2° C. per minute).

FIG. 26B is a GC profile for the reaction product of Example VI(A) containing a 25:75 mixture of isomers having the structures:

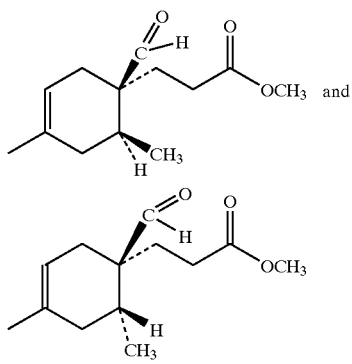

(conditions: 50 meter×0.32 mm CARBOWAX® 20M column programmed from 75° C. up to 250° C. at 2° C. per minute).

FIG. 27 is the NMR spectrum for the mixture of isomers having the structures:

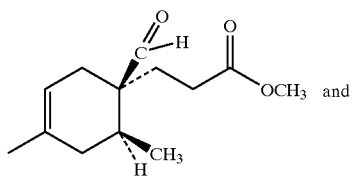

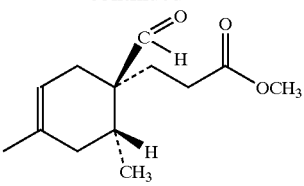

prepared according to Example VI(A).

FIG. 27A is an enlargement of section "A" of the NMR spectrum of FIG. 27.

FIG. 28A is a GC profile for the reaction product of Example VI(B) containing the compound having the structure:

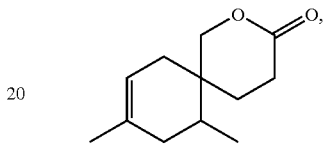

a mixture of epimers having the structures:

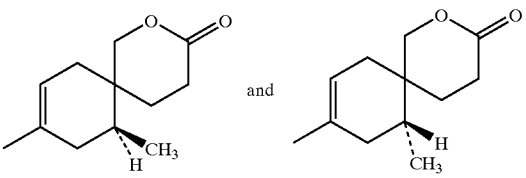

(conditions: 50 meter×0.32 mm methyl silicone column programmed from 75° C. up to 250° C. at 2° C. per minute).

FIG. 28B is a GC profile for the reaction product of Example VI(B), a mixture of epimers having the structures:

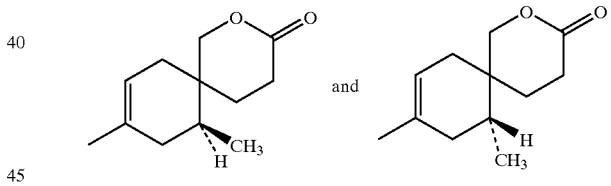

(conditions: 50 meter×0.32 mm CARBOWAX® 20M column programmed from 75° C. up to 250° C. at 2° C. per minute).

FIG. 29 is the NMR spectrum for the mixture of epimers having the structures:

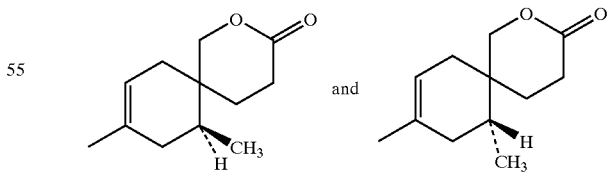

prepared according to Example VI(B).

FIG. 30 represents a cutaway side elevation view of apparatus used in forming perfumed polymers, which contain embedded in the interstices thereof one or more bicyclic lactones of our invention.

FIG. 31 is a front view of the apparatus of FIG. 30, looking in the direction of the arrows.

DETAILED DESCRIPTION OF THE DRAWINGS

Referring to FIG. 2A, the enlargement of section "A" of the NMR spectrum of FIG. 2, the peaks indicated by reference numeral 10 are for the moiety having the structure:

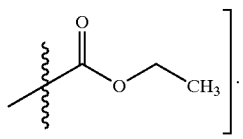

The peaks indicated by reference numeral 11 are for the moiety having the structure:

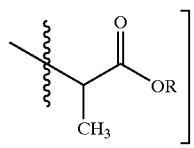

wherein one of R represents ethyl or methyl.

Referring to FIG. 2B, the enlargement of section "B" of the NMR spectrum of FIG. 2, the peaks indicated by reference numeral 12 are for the moiety having the structure:

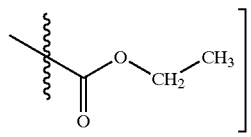

and the peaks indicated by reference numeral 13 are for the moiety having the structure:

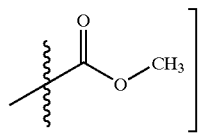

Referring to FIG. 4, the NMR spectrum for the reaction product of Example I(B), the peaks indicated by "B(1)" (also shown in FIG. 4B) are for the "trans" isomer having the structure:

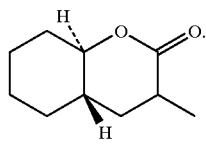

The peaks indicated by "B(2)" are for the "cis" isomer having the structure:

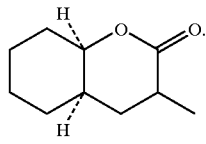

Referring to FIG. 7, the NMR spectrum for the reaction product of Example II(A), the peaks indicated by "B(1)" (also set forth on FIG. 7B, the enlargement of section "B" of FIG. 7) are for the compound having the structure:

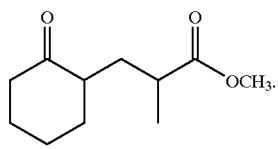

The peaks indicated by "B(2)" are for the compound having the structure

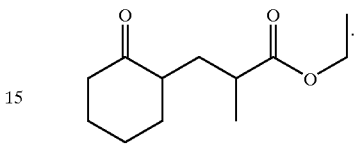

The peaks indicated by "B(2)" are also shown on FIG. 7, the enlargement of section "B" of the NMR spectrum of FIG. 7.

Referring to FIG. 13, the NMR spectrum for the reaction product of Example III(A), the peaks indicated by reference numeral 131 (also shown on FIG. 13A, the enlargement of section "A" of the NMR spectrum of FIG. 13) are for the compound having the structure:

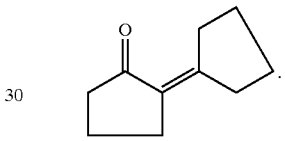

Referring to FIG. 16, the NMR spectrum for the reaction product of Example III(B), the peaks indicated by reference numeral 151 (also shown on FIG. 16B, the enlargement of section "B" of the NMR spectrum of FIG. 16) are for the compound having the structure:

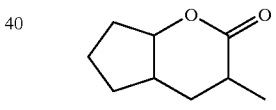

which has several isomers, including but not limited to those having the structures:

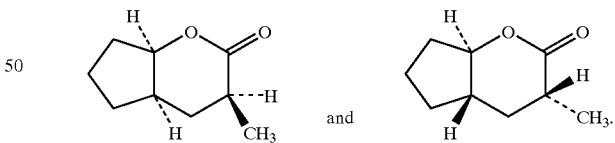

Referring to FIG. 19, the NMR spectrum for the reaction product of Example IV(A), the peak indicated by reference numeral 191 is for the moiety having the structure:

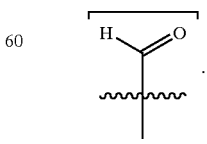

The peak indicated by reference numeral 192 is for the "saturated ring" structure, to wit:

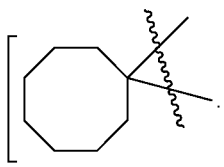

The peak indicated by reference numeral 193 is for the moiety having the structure:

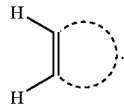

The peak indicated by reference numeral 194 is for the methoxy moiety having the structure:

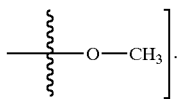

The peaks indicated by reference numeral 195 are for methylene moieties of the moiety having the structure:

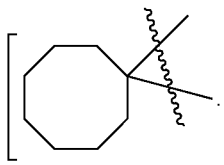

Referring to FIG. 21, the NMR spectrum for the reaction product of Example IV(B), the peak indicated by reference numeral 22 is for the moiety having the structure:

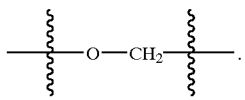

The peak indicated by reference numeral 23 is for the moiety having the structure:

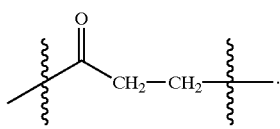

The peak indicated by reference numeral 24 is for the moiety having the structure:

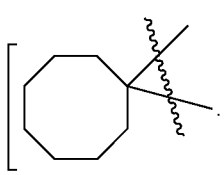

Referring to FIG. 23, the NMR spectrum for the reaction product of Example V(A), the peak indicated by reference numeral 31 is for the moiety having the structure:

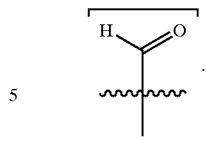

The peak indicated by reference numeral 32 is for the moiety having the structure:

The peak indicated by reference numeral 33 is for the moiety having the structure:

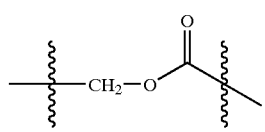

The peaks indicated by reference numeral 36 are for the moiety, having the structure:

The peaks indicated by reference numeral 35 are for the moiety having the structure:

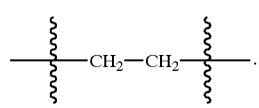

The peaks indicated by reference numeral 37 are for the moiety having the structure:

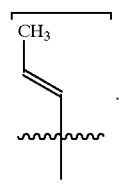

The peak indicated by reference numeral 34 is for the methyl moiety having the structure:

—CH$_3$

Referring to FIG. 25, the NMR spectrum for the reaction product of Example V(B), the peak indicated by reference numeral 41 is for the moiety having the structure:

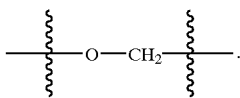

The peak indicated by reference numeral 42 is for the moiety having the structure:

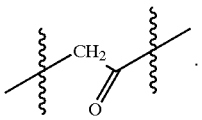

The peaks indicated by reference are for the methyl moiety having the structure:

—CH₃

Referring to FIG. 27, the NMR spectrum for the reaction product of Example VI(A), the peak indicated by reference numeral 51 is for the moiety having the structure:

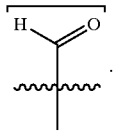

The peak indicated by reference numeral 52 is for the moiety having the structure:

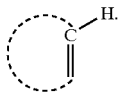

The peak indicated by reference numeral 53 is for the moiety having the structure:

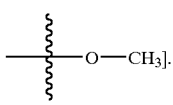

The peaks indicated by reference numeral 54 are for the moiety having the structure:

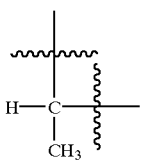

Referring to FIG. 29, the NMR spectrum of Example VI(B), the peaks indicated by reference numeral 61 are for the moiety having the structure:

The peaks indicated by reference numeral 62 are for the moiety having the structure:

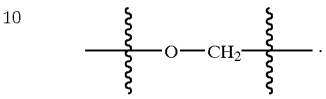

The peaks indicated by reference numeral 63 are for the moiety having the structure:

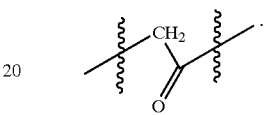

The peaks indicated by reference numeral 64 are for the moiety having the structure:

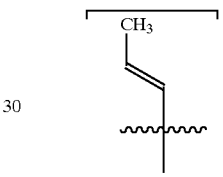

The peaks indicated by reference numeral 65 are for the moiety having the structure:

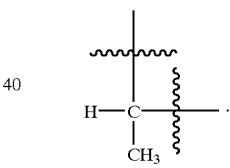

Referring to FIGS. 30 and 31, there is provided a process for forming scented polymer pellets (wherein the polymer may be a thermoplastic polymer such as low density polyethylene or polypropylene or copolymers of ethylene and vinyl acetate or mixtures of polymers and copolymers such as copolymers of ethylene and vinyl acetate and, in addition, polyethylene) such as pellets useful in the formation of plastic particles, useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature, and the material in the container is taken off at such location for delivery through the conduit. Thus, referring to FIGS. 30 and 31 in particular, the apparatus used in producing such elements comprises a device for forming the polymer containing perfume, e.g., polyethylene or polyethylene/polyvinyl acetate or mixtures of same or polypropylene or thermoplastic polyurethanes, which comprises a vat or container 212 into which the polymer taken alone or in admixture with other copolymers and the perfuming substance, which is at least one of the bicyclic lactones of our invention and other compatible perfumes, is placed. The container is closed by means of an airtight lid 228 and clamped to the container by bolts 265. A stirrer 273 traverses the lid or cover 228 in an airtight manner and is rotatable in a suitable manner. A surrounding cylinder having heating coils 212A, which are supplied with electric current through cable 214 from a rheostat or control 216, is operated to maintain the temperature inside the container 212 such that the polymer in the container will be maintained in the molten or liquid state. It has been found advantageous to employ polymers at such a temperature that the viscosity will be in the range of 90–100 Saybolt seconds. The heater 212A is operated to maintain the upper portion of the container 212 within a temperature range of, for example, 220–270° C., in the case of low density polyethylene. The bottom portion of the container 212 is heated by means of heating coils 212A regulated through the control 220 connected thereto through a connecting wire 222 to maintain the lower portion of the container 212 within a temperature range of 220–270° C.

Thus, the polymer or mixture of polymers added to the container 212 is heated from 10–12 hours, whereafter the perfume composition or perfume material which contains at least one of the bicyclic lactones of our invention is quickly added to the melt. Generally, about 10–45% by weight of the resulting mixture of the perfumery substance is added to the polymer.

After the perfume material is added to the container 212, the mixture is stirred for a few minutes, for example, 5–15 minutes, and maintained within the temperature ranges indicated, previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 (indicated in cross section by reference numeral 218) having a multiplicity of orifices 234 adjacent to the lower side thereof. The outer end of the conduit 232 is closed so that the liquid polymer in intimate admixture with at least one of the bicyclic lactones of our invention will continuously drop through the orifices of 234 downwardly from the conduit 232. During this time, the temperature of the polymer intimately admixed with the perfumery substance in the container 212 is accurately controlled so that a temperature in the range of from about 240–250° C., for example, (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance which is at least one of the bicyclic lactones of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

The belt 238 is cooled, for example, by means of sponge 256, which is exposed to a cooling water bath containing water 254 contained in container 250 having side walls 248. As the belt 238 moves, it is cooled by the water from sponge 256.

THE INVENTION

The present invention provides bicyclic lactones, both fused ring lactones defined according to the generic structure:

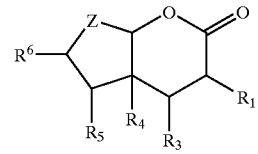

and spiro lactones defined according to the generic structure:

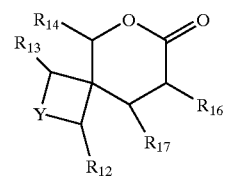

and uses thereof in augmenting, enhancing or imparting an aroma in or to a perfume compositions, colognes and perfumed articles (e.g., solid or liquid anionic, cationic, nonionic or zwitterionic detergents, fabric softener compositions, fabric softener articles, perfumed polymers and cosmetic powders).

With respect to the bicyclic lactones defined according to the structure:

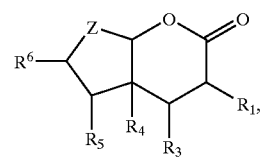

Z is one of the moieties:

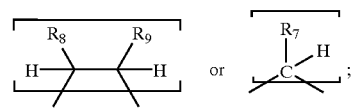

one of $R_1$ or $R_3$ is methyl and the other is hydrogen; and $R_4$, $R_5$, $R_6$, $R_7$, $R_8$ and $R_9$ are hydrogen or nonadjacent $C_1$–$C_3$ alkyl, as exemplified by one of the compounds having the structures:

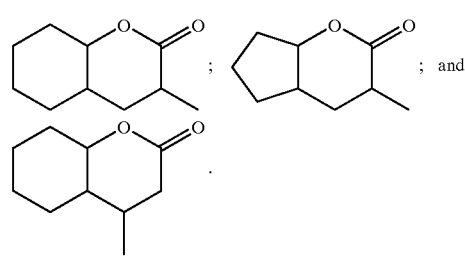

With respect to the bicyclic lactones defined according to the structure:

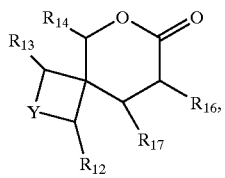

Y represents $C_2$–$C_{12}$ substituted or unsubstituted alkylidenyl, alkadienylidenyl or alkenylidenyl defined according to the structure:

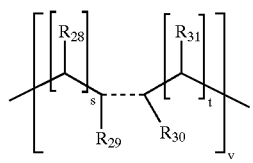

and completes a $C_5$–$C_{15}$ cycloalkyl, cycloalkadienyl or cycloalkenyl ring moiety; wherein $R_{12}$, $R_{13}$, $R_{14}$, $R_{16}$ and $R_{17}$ each represents hydrogen or $C_1$–$C_3$ nonadjacent alkyl; the dashed line represents a carbon carbon single bond or a carbon carbon double bond; $R_{28}$, $R_{29}$, $R_{30}$ and $R_{31}$ represents hydrogen or $C_1$–$C_3$ nonadjacent alkyl; s is an integer of from 0 up to 10; t is an integer of from 0 up to 10; with the proviso that the sum of s and t is between 0 and 10 according to the inequalities: $0 \leq s+t \leq 10$; $0 \leq s \leq 10$; and $0 \leq t \leq 10$; and v is an integer of 1 or 2, as exemplified by a compound having one of the structures:

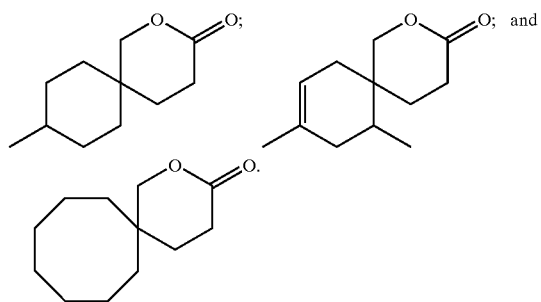

The bicyclic lactones of our invention impart, augment or enhance sweet, fruity, nutty, hay-like, coumarinic, tonka, tobacco, lactonic, green, tagette, woody, earthy, ambery, orris, coconut, spicy and cinnamon aromas with "cooling" nuances with nutty, hay-like, orris, woody and coumarinic topnotes and woody, jasmine, floral, nutty, lactonic, spicy and cinnamon undertones to perfume compositions, colognes and perfumed articles (e.g., solid or liquid anionic, cationic, nonionic or zwitterionic detergents, perfumed polymers, fabric softener compositions, fabric softener articles, cosmetic powders and the like).

The bicyclic lactones of our invention defined according to the structure:

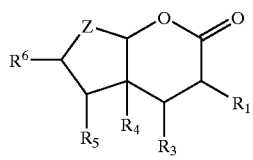

may be prepared by means of first reacting a cyclic ketone defined according to the structure:

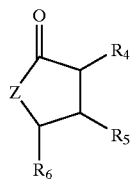

with a heterocyclic nitrogen-containing compound defined according to the structure:

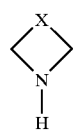

wherein X is one of the moieties:

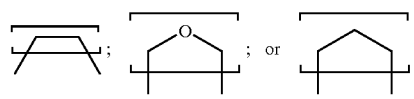

in order to form a compound defined according to the structure:

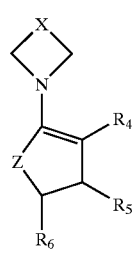

according to the reaction:

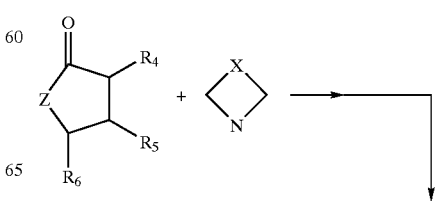

-continued

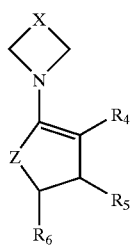

The resulting compound having the structure:

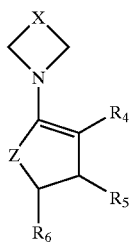

is then reacted with an acrylic acid ester defined according to the structure:

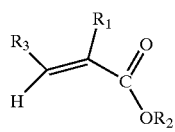

in order to form a compound having to the structure:

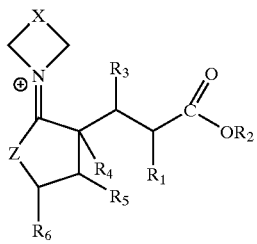

according to the reaction:

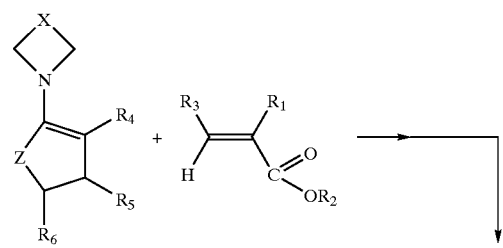

-continued

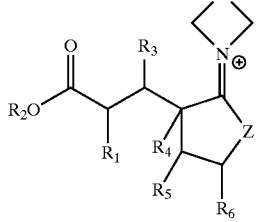

wherein $R_2$ is $C_1$–$C_4$ alkyl.

The resulting product having the structure:

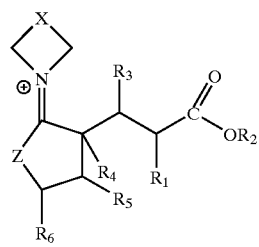

is then hydrolyzed using weak acid such as dilute hydrochloric acid or acetic acid in order to form the compound having the structure:

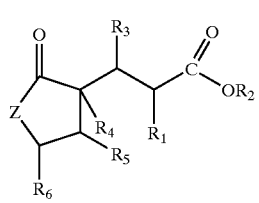

according to the reaction:

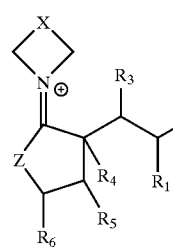

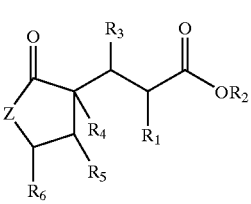

The resulting product is reduced with hydrogen to form the compound having the structure:

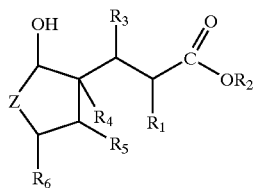

according to the reaction:

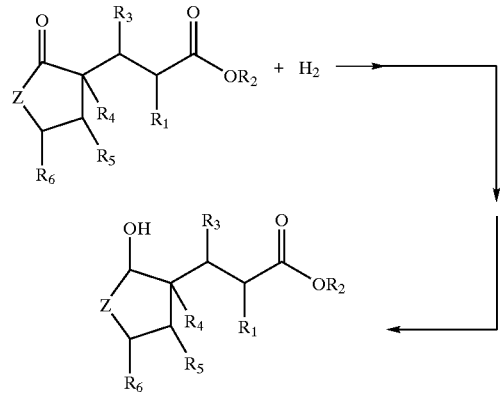

The hydrogenation reaction may be carried out in the presence of a Raney nickel catalyst at pressures in the range of from about 400 up to about 600 pounds per square inch absolute and at a temperature in the range of from about 120 up to about 150° C. in the presence of an inert solvent such as isopropyl alcohol.

The resulting product having the structure:

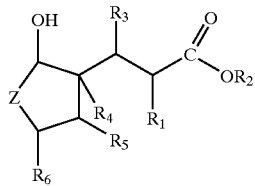

is not isolated, but on heating as by means of carrying out the fractional distillation thereof, is converted directly into the desired bicyclic lactone product having the structure:

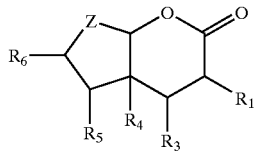

according to the reaction:

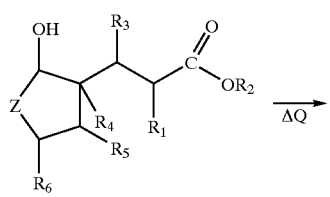

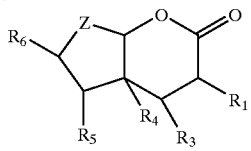

with the liberation of the alcohol, $R_2$—OH.

In formation of the bicyclic lactones defined according to the structure:

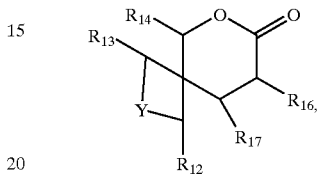

a cyclic substituted carboxaldehyde or substituted ketone having the structure:

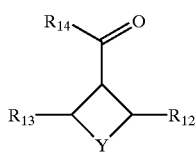

is reacted with a compound defined according to the structure:

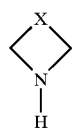

in order to form a compound having the structure:

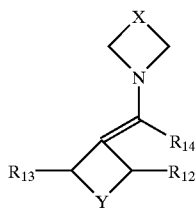

according to the reaction:

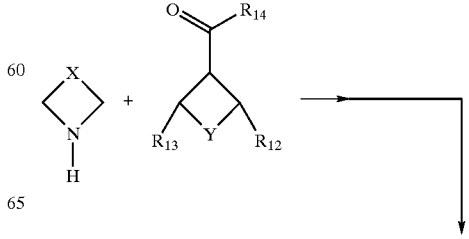

-continued

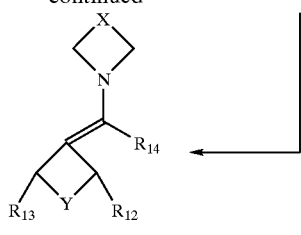

The resulting compound having the structure:

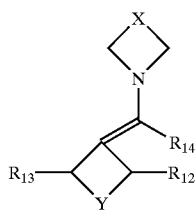

is then further reacted with an acrylic acid ester derivative defined according to the structure:

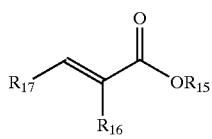

in order to form a compound having the structure:

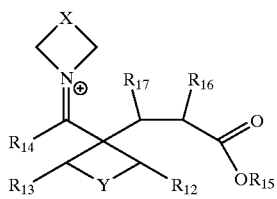

wherein $R_{15}$ is $C_1$–$C_4$ alkyl according to the reaction:

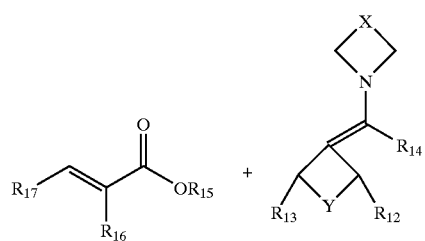

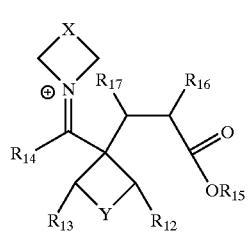

The resulting product having the structure:

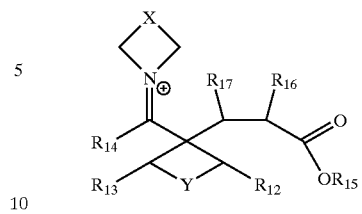

is then hydrolyzed in the presence of weak acid such as dilute hydrochloric acid or acetic acid in order to form the carboxaldehyde or ketone defined according to the structure:

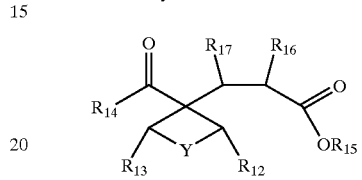

according to the reaction:

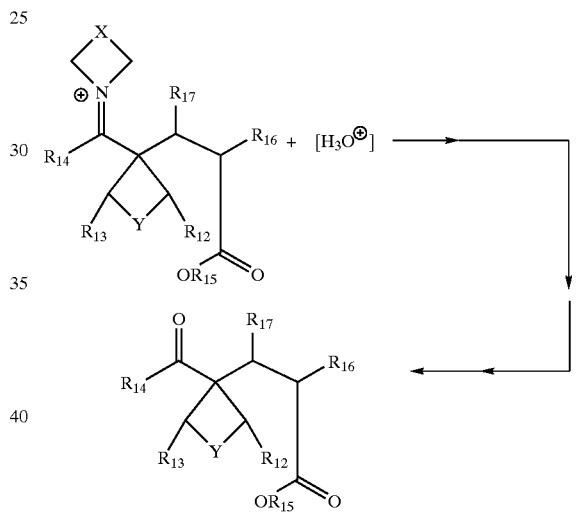

The resulting carboxaldehyde or ketone defined according to the structure:

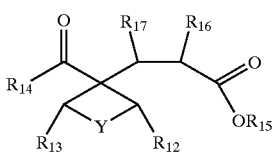

is then reduced using hydrogen in the presence of a Raney nickel catalyst or a copper chromite (CuCr) in order to form a compound having the structure:

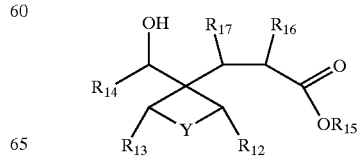

according to the reaction:

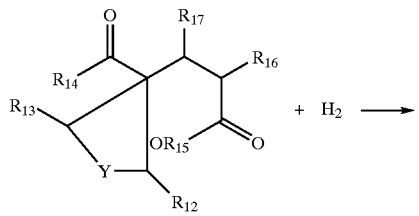

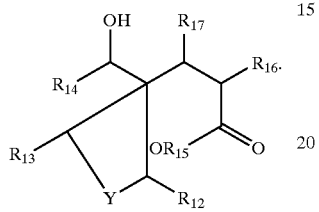

A feature of the latter reaction is that in the event that a Raney nickel catalyst is utilized, the Y moiety is totally reduced to form a cycloalkyl moiety, whereas if a copper chromite catalyst is used in the hydrogenation, the moiety Y is not reduced should a double bond be present in that moiety, thereby retaining the unsaturation feature in the ring moiety, but still reducing the ketone or carboxaldehyde moiety to an alkanol moiety.

The resulting compound having the structure:

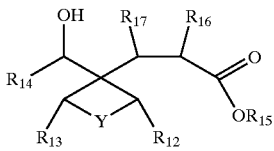

is not, however, isolated, but on distillation (for example, fractional distillation with heating), forms the desired bicyclic ketone according to the reaction:

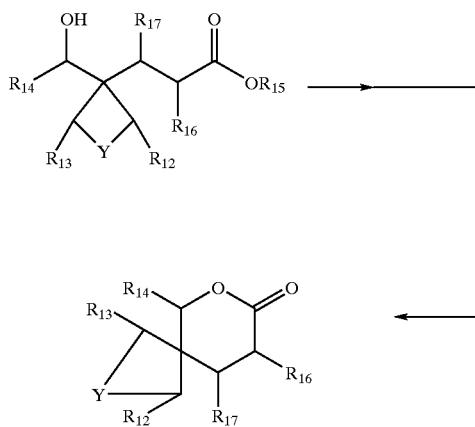

with the liberation of the alkanol having the structure: $R_{15}$—OH.

The following table sets forth the bicyclic ketones of our invention, exemplary structures of the bicyclic ketones of our invention and their fragrance properties:

TABLE I

| Structure of Compound | Perfume Property |
|---|---|
| The compound having the structure:<br>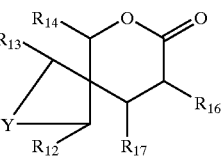<br>prepared according to Example I(B), bulked distillation fractions 7–9. | A fruity, nutty, hay-like, coumarinic aroma with "cooling" nuances and with jasmine and floral undertones. |
| The compound having the structure:<br><br>prepared according to Example II(B), bulked distillation fractions 4–9. | A sweet, coumarinic, tonka, tobacco, lactonic aroma with nutty and hay-like topnotes. |
| The compound having the structure:<br><br>prepared according to Example III(B), bulked distillation fractions 4–12. | A green, tagette, coumarinic aroma with "cooling" nuances and nutty and lactonic undertones. |

TABLE I-continued

| Structure of Compound | Perfume Property |
|---|---|
| The compound having the structure:<br>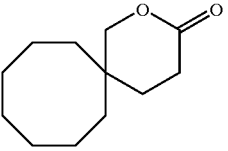<br>prepared according to Example IV(B), bulked distillation fractions 5–7. | A woody, earthy, ambery, green aroma with lactonic and woody undertones. |
| The compound having the structure:<br>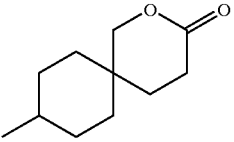<br>prepared according to Example V(B), bulked distillation fractions 4–10. | A woody, orris, coconut, coumarinic aroma with orris, woody and coumarinic topnotes. |
| The compound having the structure:<br>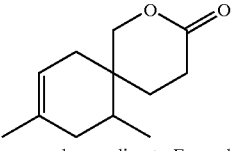<br>prepared according to Example VI(B), bulked distillation fractions 4–10. | A lactonic, spicy, cinnamon aroma with lactonic, spicy and cinnamon undertones. |

The bicyclic lactones prepared in accordance with the process of our invention having the generic structures:

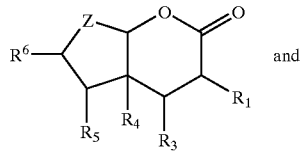 and 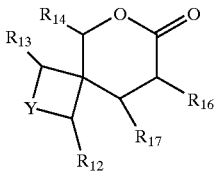

and one or more auxiliary perfume ingredients, including, for example, alcohols, aldehydes, terpenic hydrocarbons, ketones, esters, lactones other than the lactones of our invention, natural essential oils, synthetic essential oils, mercaptans and alkylmercapto derivatives, may be admixed so that the combined odors of the individual components produce a pleasant and desired fragrance, particularly and preferably in the floral-type fragrances (specifically, for example, the jasmine/galbanum fragrances). Such perfume compositions usually contain (a) the main note or the "bouquet" or foundation stone of the composition; (b) modifiers which round off and accompany the main note; (c) fixatives, which include odorous substances which lend a particular note to the perfume throughout all stages of evaporation and substances which retard evaporation; and (d) topnotes, which are usually low boiling, fresh-smelling materials.

In perfume compositions, it is the individual compositions which contribute to their particular olfactory characteristics. However, the overall sensory effect of the perfume composition will be at least the sum total of the effects of each of the ingredients. Thus, the bicyclic lactones of our invention can be used to alter, modify or enhance the aroma characteristics of a perfume composition, for example, by utilizing or moderating the olfactory reaction contributed by another ingredient in the composition.

The amount of the bicyclic lactones of our invention, which will be effective in perfume compositions as well as in perfumed articles (e.g., solid or liquid soaps, fabric softener compositions, dryer-added fabric softener articles, optical brightener compositions, perfumed polymers and textile sizing agents and colognes) depends on many factors, including other ingredients, their amounts and the effects which are desired. It has been found that perfume compositions containing as little as 0.01% of at least one of the bicyclic lactones of our invention or even less (e.g., 0.005%) can be used to impart, augment or enhance intense and substantive, sweet, fruity, nutty, hay-like, coumarinic, tonka, tobacco, lactonic, green, tagette, woody, earthy, ambery, orris, coconut, spicy and cinnamon aromas with "cooling" nuances with nutty, hay-like, orris, woody and coumarinic topnotes and with woody, jasmine, floral, nutty, lactonic, spicy and cinnamon undertones to soaps, cosmetics, anionic, cationic, nonionic or zwitterionic detergents, fabric softener compositions, fabric softener articles, optical brightener compositions, textile sizing compositions, perfumed polymers or other products. The amount employed can range up to 70% or even 100% of the fragrance components and will depend on considerations of cost, nature of the end product, the effect desired on the finished product and the particular fragrance sought.

The bicyclic lactones of our invention are useful (taken alone or together with other ingredients and perfume compositions) as (an) olfactory component(s) in detergents and soaps, space odorants and deodorants, perfumes, colognes, toilet water, bath preparations, such as creams, deodorants, hand lotions and sun screens; powders such as talcs, dusting powders, face powders and perfumed polymers and articles of manufacture produced from said perfumed polymers. When used as (an) olfactory component(s) of a perfumed article, as little as 0.2% of at least one of the bicyclic lactones of our invention will suffice to impart highly intense, sweet, fruity, nutty, hay-like, coumarinic, tonka, tobacco, lactonic, green, earthy, ambery, orris, coconut and cinnamon aromas with "cooling" nuances with nutty, hay-like, nutty, orris, woody, coumarinic topnotes and woody, jasmine, floral, nutty, lactonic, spicy and cinnamon undertones to floral perfume formulations. Generally, no more than 6% of at least one of the bicyclic lactones of our invention, based on the ultimate end-product,is required in the perfumed article composition. Accordingly, the range of the bicyclic lactones of our invention in the perfumed articles is from about 0.2% by weight of at least one of the bicyclic lactones of our invention up to about 6% by weight of at least one of the bicyclic lactones of our invention in the perfumed article.

In addition, the perfume composition or fragrance composition of our invention can contain a vehicle or carrier for at least one of the bicyclic lactones of our invention. The vehicle can be a liquid such as a nontoxic alcohol, e.g., ethyl alcohol; a nontoxic glycol, e.g., propylene glycol or the like. The carrier can also be an absorbent solid such as a gum (e.g., gum arabic, guar gum or xanthan gum) or components for encapsulating the composition (such as gelatin) as by coacervation; or components for forming a polymer wall around a liquid perfume center such as a urea formaldehyde prepolymer.

Our invention also relates to the utilization of controlled release technology for the controlled release of perfumes into gaseous environments from polymers such as mixtures of epsilon polycaprolactone polymers and polyethylene, which polyepsilon caprolactone polymers are defined in U.S. Pat. No. 5,300,489 issued on Apr. 5, 1994, incorporated herein by reference.

The polyepsilon caprolactone polymers useful in practicing our invention are more specifically described in the brochure of the Union Carbide Corporation, 270 Park Avenue, New York, N.Y. 10017, entitled "NEW POLYCAPROLACTONE THERMOPLASTIC POLYMERS PL-300 AND PCL-700." These polyepsilon caprolactone polymers are composed of a repeating sequence of nonpolar methylene groups and relatively polar ester groups. The average number of repeating monomeric units varies between 150 and 700, depending on the particular "PCL" number. Thus, regarding PCL-300, the average number of repeating monomeric units is about 300. Regarding PCL-700, the average number of repeating monomeric units is 700.

The polyepsilon caprolactone homopolymers, which are ultimately taken in admixture with such materials as polyethylene useful in the practice of our invention, may be also stabilized using stabilizers as defined in U.S. Pat. No. 4,360,682 issued on Nov. 23, 1982, the specification for which is incorporated by reference herein. The stabilizing materials which stabilized the polyepsilon caprolactone (useful in conjunction with our invention) against discoloration are dihydroxybenzenes as set forth at column 13, line 20 of U.S. Pat. No. 5,300,489. A method for incorporating the bicyclic lactones of our invention into such polyepsilon caprolactone homopolymers is set forth in U.S. Pat. No. 3,505,432 incorporated herein by reference.

The following Examples I–VI illustrative of processes for preparing the bicyclic lactones of our invention. The examples following Example VI, e.g., Examples VII, et seq., are illustrative of the organoleptic utilities of the bicyclic lactones of our invention.

All parts and percentages given herein are by weight unless otherwise specified.

EXAMPLE I

Preparation of 3-Methyl-octahydro-2H-1-benzopyran-2-one

EXAMPLE 1(A)

Reactions:

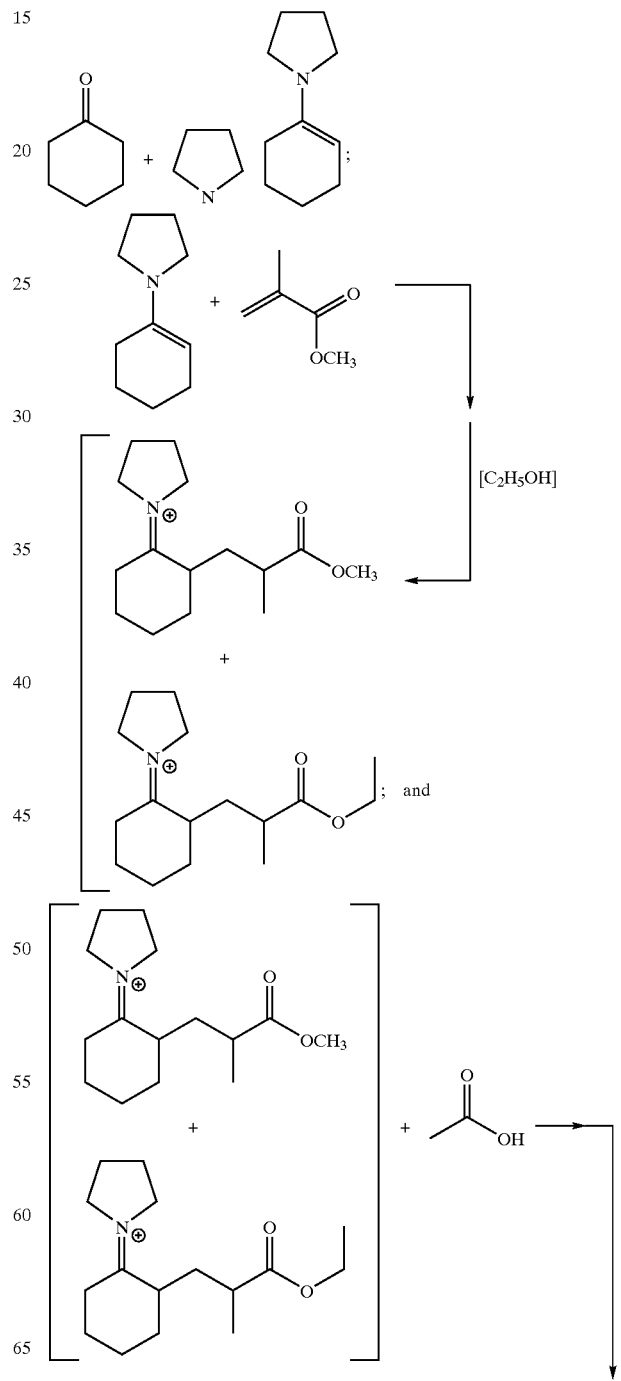

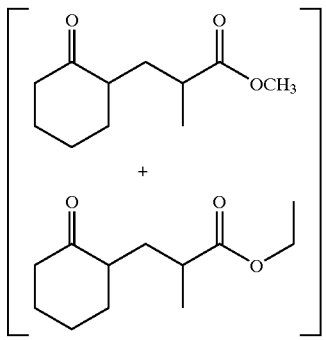

Into a 2 liter reaction vessel are placed 370 grams of the enamine having the structure:

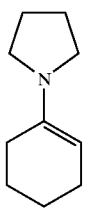

(2.4 moles) and 500 ml ethyl alcohol. The resulting mixture is heated to reflux at 82° C. Over a 2-hour period, 300 grams of methyl methacrilate having the structure:

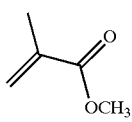

is added to the reaction mass. The resulting mixture is heated for a period of 1 hour at reflux.

The resulting product then admixed with an equal volume of 20% acetic acid and heated at 85–90° C. for a period of 4 hours, and the resulting product is then distilled yielding a mixture of compounds having the structures:

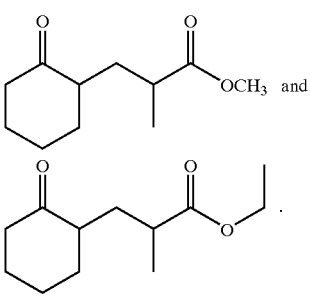

The resulting product is fractionally distilled yielding the following distillation fractions:

| Fraction No. | Vapor Temperature | Liquid Temperature | Vacuum mm/Hg | Reflux Ratio |
|---|---|---|---|---|
| 1 | 23/38 | 23/170 | 100/25 | 100% |
| 2 | 112 | 132 | 200 | 4:1 |
| 3 | 112 | 132/18 | 1 | 1:4 |
| 4 | 145 | 210 | 4 | 1:4 |

EXAMPLE I(B)

Reactions:

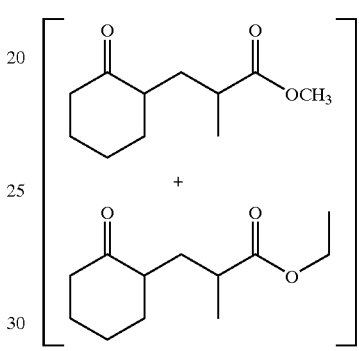 + H$_2$ →

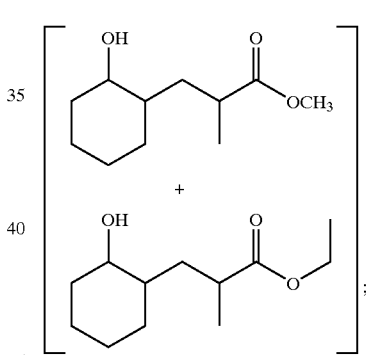 ; and

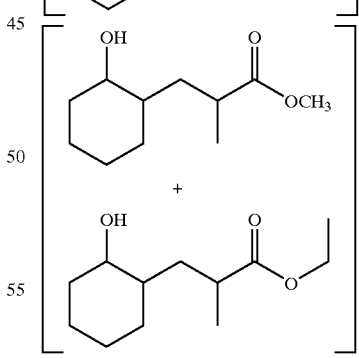 $\xrightarrow{+\Delta Q}$

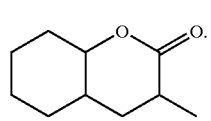

Into a 1 liter autoclave are placed 4.4 grams of Raney nickel, 40 cc of anhydrous isopropyl alcohol and 410 grams of the mixture of compounds having the structures:

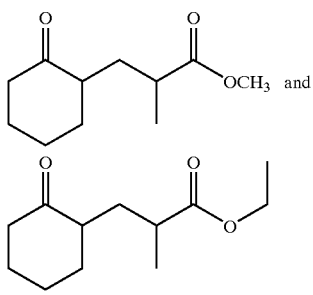

prepared according to Example I(A).

The autoclave is sealed and pressurized with hydrogen at 550 psia at a temperature of from 130 up to 135° C. The autoclave is maintained at 550 psia for a period of 4 hours at a temperature of 130–135° C. At the end of the reaction, the autoclave is opened, and the reaction mass is filtered and fractionally distilled, yielding the following fractions:

| Fraction No. | Vapor Temperature | Liquid Temperature | Vacuum mm/Hg | Reflux Ratio |
| --- | --- | --- | --- | --- |
| 1 | 23 | 23 | 1 | 100% |
| 2 | 125 | 131 | 1 | 4:1 |
| 3 | 124 | 132 | 1 | 4:1 |
| 4 | 122 | 133 | 1 | 2.5:1 |
| 5 | 122 | 133 | 1 | 2.5:1 |
| 6 | 125 | 134 | 1 | 2.5:1 |
| 7 | 119 | 131 | 4 | 2.5:1 |
| 8 | 116 | 132 | 4 | 2.5:1 |
| 9 | 116 | 131 | 4 | 2.5:1 |
| 10 | 111 | 124 | 3.5 | 2.5:1 |
| 11 | 105 | 147 | 0.9 | 4:1 |
| 12 | 99 | 200 | 0.9 | 4:1 |

NMR, IR and mass spectral analyses yield the information that the resulting product has the structure:

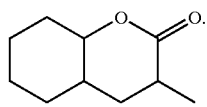

EXAMPLE II

Preparation of 4-Methyl-octahydro-2H-1-benzopyran-2-one

EXAMPLE II(A)

Reactions:

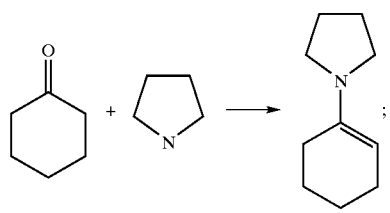

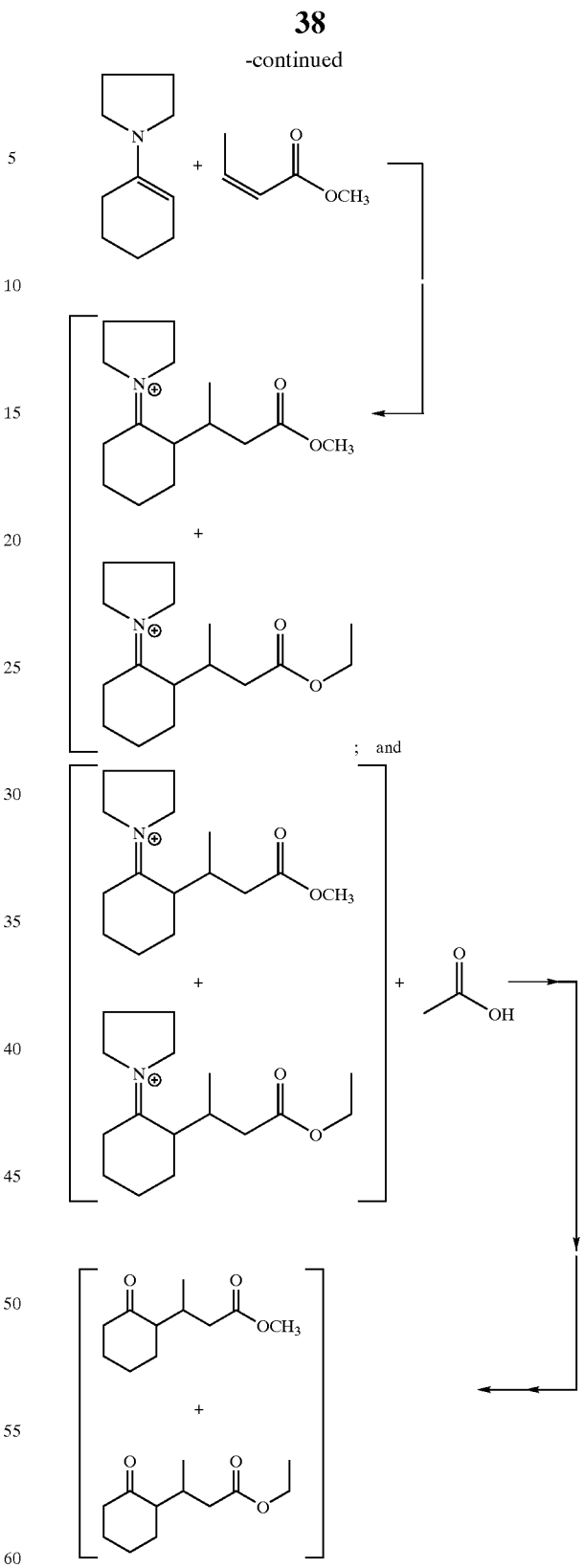

Into a 2 liter reaction vessel equipped with thermometer, reflux condenser, heating mantle and Bidwell water recovery apparatus are placed 343 grams (3.5 moles) of cyclohexanone, 270 grams (3.8 moles) of pyrollidine, 300 ml benzene and 6 grams of paratoluene sulfonic acid.

The reaction mass with stirring is heated to 108° C. and maintained at 108° C. with stirring for a period of 1 hour. At the end of the 1 hour period, the reaction mass is cooled to 35° C., and 7 grams of sodium acetate is added thereto. The reaction mass is filtered and stripped of solvent. The resulting product is then admixed with 350 grams (3.5 moles) of methyl crotonate and 400 ml ethyl alcohol. The resulting mixture is then heated to 84° C. and refluxed at 84° C. for a period of 2 hours. At the end of the 2 hour period, the reaction mass is cooled to 35° C. and admixed with 1 liter of 10% acetic acid.

The resulting mixture is then heated to 90° C. and refluxed at 90° C. for a period of 4 hours. At the end of the 4 hour period, the resulting product containing compounds having the structures:

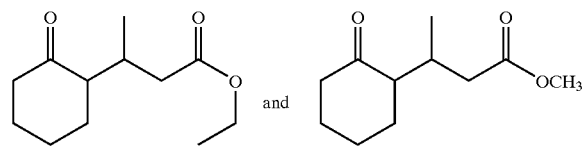

is fractionally distilled, yielding the following fractions:

| Fraction No. | Vapor Temperature | Liquid Temperature | Vacuum mm/Hg | Reflux Ratio |
|---|---|---|---|---|
| 1 | 23/38 | 23/110 | 200/30 | 100% |
| 2 | 80 | 118 | 5 | 100% |
| 3 | 111 | 142 | 1 | 100% |
| 4 | 130 | 185 | 1 | 100% |
| 5 | 40 | 210 | 4 | 100% |

NMR, IR and mass spectral analyses yield the information that the ratio of the compounds having the structures:

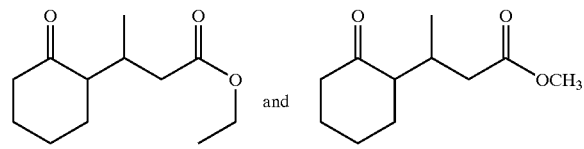

is 23:77 (23 parts by weight of the compound having the structure:

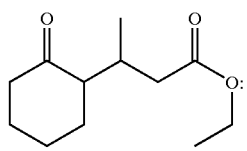

77 parts by weight of the compound having the structure:

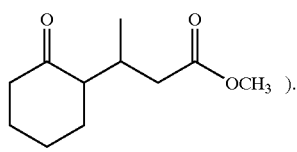

EXAMPLE II(B)

Reactions:

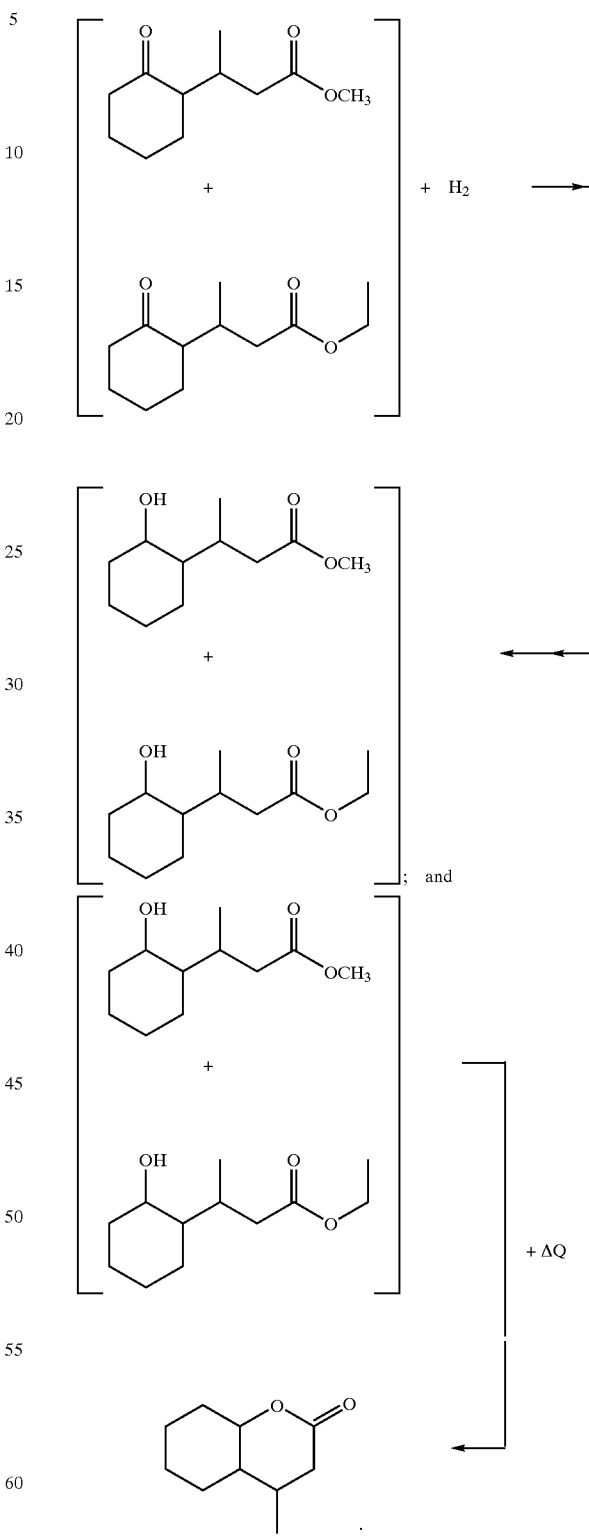

Into a 1 liter autoclave equipped with hydrogen feed line are placed 5.5 grams of Raney nickel; 454 grams of the mixture of compounds having the structures:

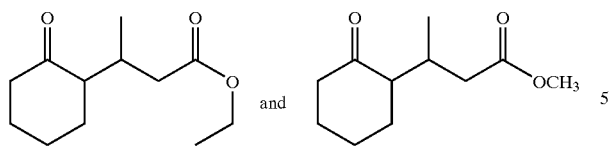

prepared according to Example I(A); and 40 ml of anhydrous isopropyl alcohol.

The autoclave is sealed and pressurized to 500 psia with hydrogen while maintaining the temperature of the reaction mass at 130–135° C. The hydrogen is fed into the autoclave while maintaining the pressure at 500 psia for a period of 7 hours. At the end of the 7 hour hydrogenation period, the autoclave is cooled and opened, and the reaction product is filtered. The solvent is distilled off and then the reaction mass is fractionally distilled, yielding the following fractions:

| Fraction No. | Vapor Temperature | Liquid Temperature | Vacuum mm/Hg | Reflux Ratio |
|---|---|---|---|---|
| 1 | 23/31 | 23/231 | 760/2 | 100% |
| 2 | 118 | 132 | 1.8 | 9:1 |
| 3 | 116 | 132 | 0.8 | 9:1 |
| 4 | 117 | 133 | 4 | 9:1 |
| 5 | 117 | 133 | 4 | 9:1 |
| 6 | 116 | 132 | 4 | 9:1 |
| 7 | 112 | 132 | 4 | 9:1 |
| 8 | 117 | 138 | 4 | 9:1 |
| 9 | 117 | 138 | 4 | 9:1 |
| 10 | 115 | 136 | 0.8 | 9:1 |
| 11 | 114 | 136 | 0.8 | 9:1 |
| 12 | 114 | 136 | 0.8 | 9:1 |
| 13 | 116 | 142 | 0.8 | 9:1 |
| 14 | 114 | 152 | 0.8 | 9:1 |
| 15 | 105 | 200 | 0.7 | 9:1 |

NMR, GLC, IR and mass spectral analyses yield the information that the resulting compound of bulked distillation fractions 4–9 has the structure:

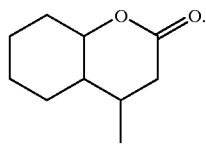

EXAMPLE III

Preparation of 3-Methyl Hexahydrocyclopenta[B]pyran-2[3H]-one

EXAMPLE III(A)

Reactions:

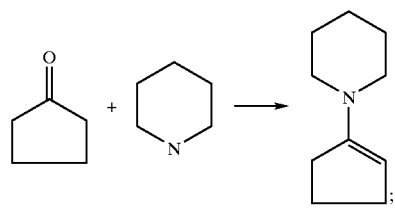

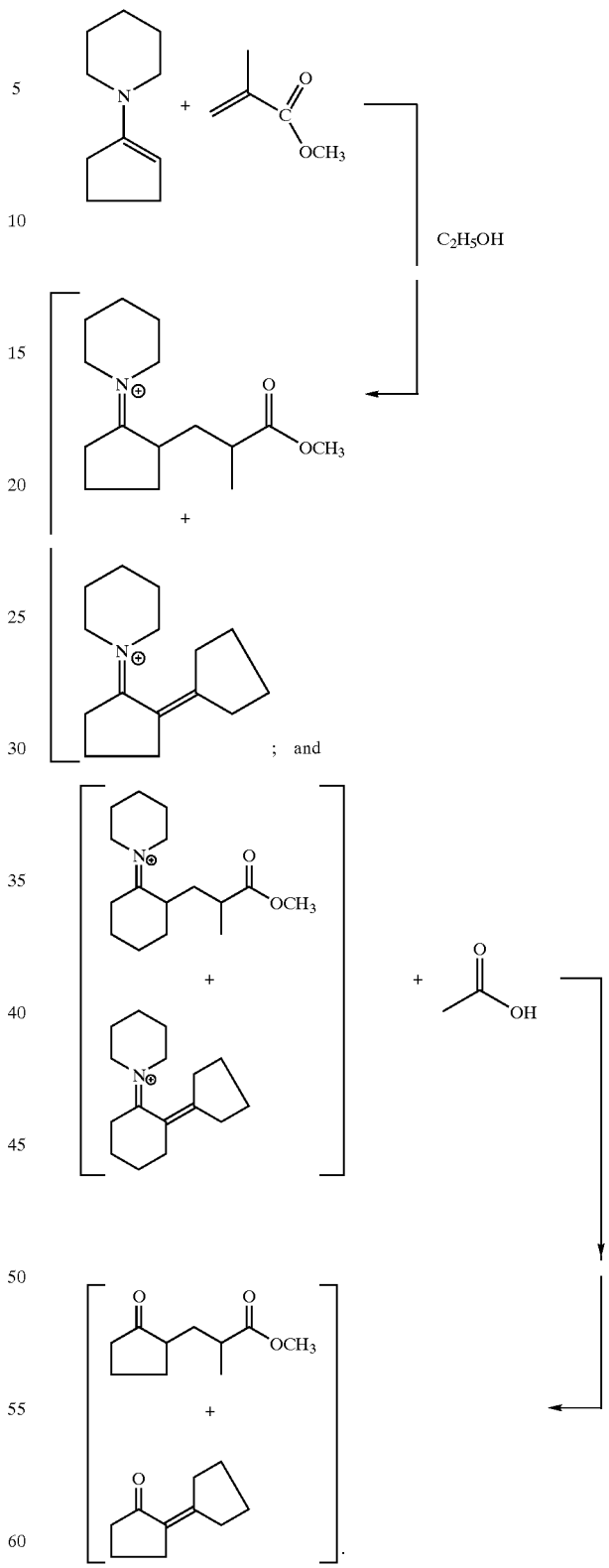

Into a 2 liter reaction vessel equipped with stirrer, themometer, reflux condenser and heating mantle are placed 550 grams of enamine having the structure:

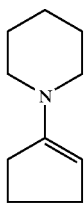

and 300 grams of ethyl alcohol. The resulting mixture is heated to reflux (84° C.), and while the refluxing is taking place over a 2 hour period, 400 grams (4.0 moles) of methyl methacrylate having the structure:

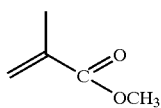

is added to the reaction mass. The reaction mass is refluxed for an additional 2 hour period at 84° C. The reaction mass is then cooled and admixed with an equal volume of a 50:50 mixture of water and acetic acid. The resulting product is then heated with stirring at 95–100° C. over period of 4 hours. The reaction mass is then admixed with an equal volume of saturated sodium bicarbonate.

The resulting mixture now exists in two phases: an aqueous phase and an organic phase. The organic phase is separated from the aqueous phase and dried over anhydrous magnesium sulfate. The resulting dried product is then fractionally distilled yielding the following fractions:

| Fraction No. | Vapor Temperature | Liquid Temperature | Vacuum mm/Hg | Reflux Ratio |
|---|---|---|---|---|
| 1 | 23/33 | 23/110 | 200/15 | 100% |
| 2 | 112 | 137 | 1 | 100% |
| 3 | 113/127 | 138/185 | 1 | 100% |
| 4 | 178 | 191 | 0.8 | 100% |
| 5 | 183 | 210 | 0.8 | 100% |

The resulting product is confirmed by NMR, GLC and mass spectral analysis to be a mixture of compounds having the structures:

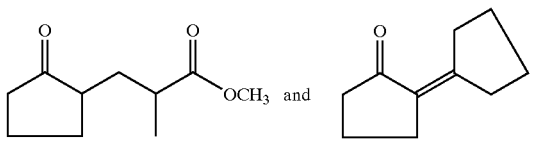

with the compound having the structure:

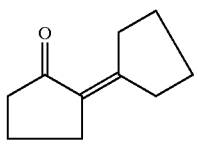

to be a minor component.

EXAMPLE III(B)

Reactions:

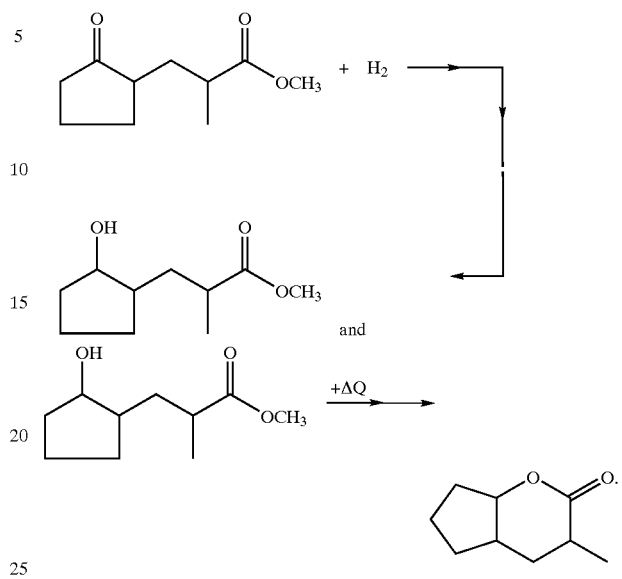

Into a 1 liter autoclave equipped with hydrogen feed line are place 4.5 grams of Raney nickel, 45 grams of anhydrous isopropyl alcohol and 410 grams of compound having the structure:

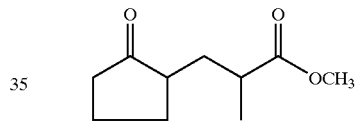

prepared according to Example III(A).

The autoclave is sealed and pressurized to 550 psia with hydrogen while the temperature is maintained at 130–135° C. The hydrogen pressurization at 550 psia is maintained for a period of 8 hours. At the end of the 8 hour period, the autoclave is cooled, depressurized and opened. The contents of the autoclave are filtered and fractionally distilled, yielding the following fractions:

| Fraction No. | Vapor Temperature | Liquid Temperature | Vacuum mm/Hg | Reflux Ratio |
|---|---|---|---|---|
| 1 | 23/42 | 23/210 | 760/760 | 100% |
| 2 | 105 | 131 | 3 | 9:1 |
| 3 | 116 | 128 | 3 | 9:1 |
| 4 | 124 | 129 | 2 | 9:1 |
| 5 | 122 | 126 | 2 | 9:1 |
| 6 | 122 | 127 | 2 | 9:1 |
| 7 | 124 | 129 | 2 | 9:1 |
| 8 | 123 | 131 | 2 | 1:1 |
| 9 | 122 | 132 | 2 | 1:1 |
| 10 | 122 | 131 | 2 | 1:1 |
| 11 | 123 | 131 | 2 | 1:1 |
| 12 | 123 | 133 | 2 | 1:1 |
| 13 | 123 | 139 | 2 | 1:1 |
| 14 | 115 | 172 | 1 | 1:1 |

Fractions 4–12 are bulked. Bulked distillation fractions 4–12 are confirmed by NMR, IR and mass spectral analyses to have the structure:

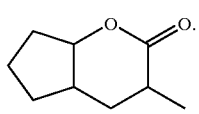

EXAMPLE IV

Preparation of 2-oxaspiros[5.7]tridecan-3-one

EXAMPLE IV(A)

Reactions:

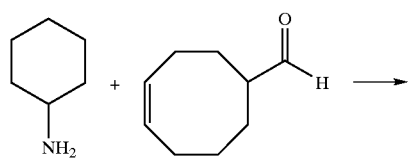

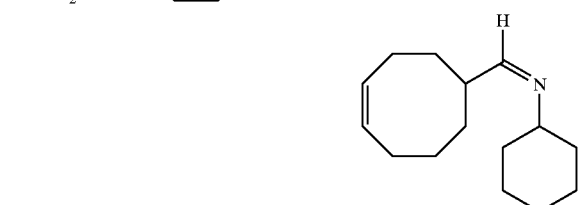

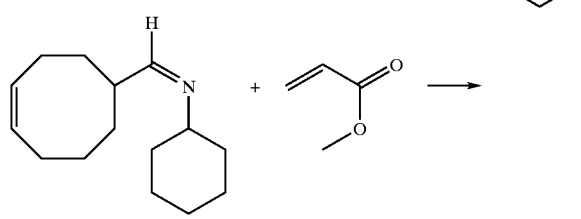

and

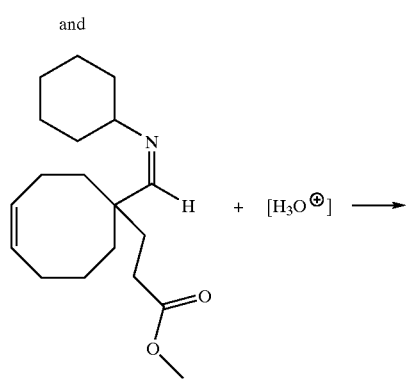

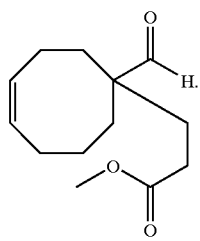

Into a 2 liter reaction vessel equipped with stirrer, thermometer, heating mantle, reflux condenser and Bidwell water recovery apparatus are placed 324 grams of the compound having the structure:

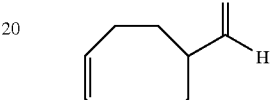

(2.35 moles); 246 grams of cyclohexyl amine (2.5 moles); and 300 ml of anhydrous toluene.

The resulting mixture is refluxed at 149° C. and water of the reaction is recovered using the Bidwell water recovery apparatus. The reaction takes place over a period of 2 hours. At the end of the 2 hour reaction period, the reaction mass is cooled to 110° C. and 258 grams (3.0 moles) of methyl acrylate having the structure:

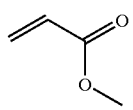

is added to the reaction mass. The reaction product is then stirred at reflux for a period of 10 hours. At the end of the 10 hour period, the reaction mass is cooled to 35° C. and an equal volume of 5% aqueous hydrochloric acid is added to the reaction mass.

The reaction mass is then stirred at 40° C. for a period of 2 hours. At the end of the 2 hour period, the reaction mass is washed with 1 equal volume of water followed by 1 equal volume of saturated sodium bicarbonate. The reaction mass is then dried over anhydrous magnesium sulfate and fractionally distilled yielding the following fractions:

| Fraction No. | Vapor Temperature | Liquid Temperature | Vacuum mm/Hg | Reflux Ratio |
|---|---|---|---|---|
| 1 | 23/41 | 29/120 | 210/15 | 100% |
| 2 | 132 | 171 | 0.8 | 100% |
| 3 | 152 | 184 | 0.8 | 100% |
| 4 | 157 | 210 | 0.8 | 100% |
| 5 | 187 | 230 | 0.8 | 100% |

NMR, IR, GLC and mass spectral analyses yield the information that the resulting reaction product is the compound having the structure:

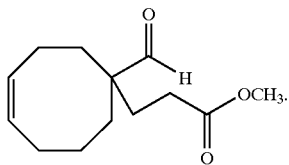

EXAMPLE IV(B)

Reactions:

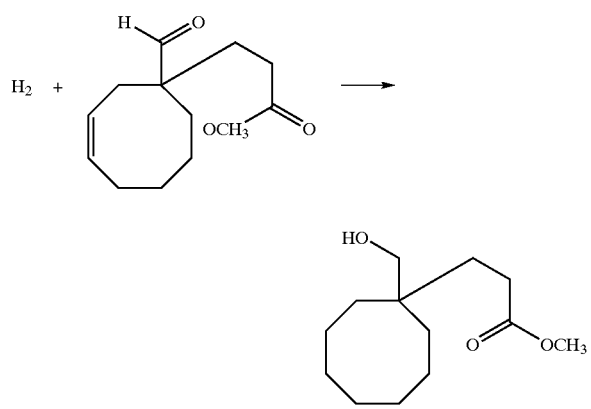

and

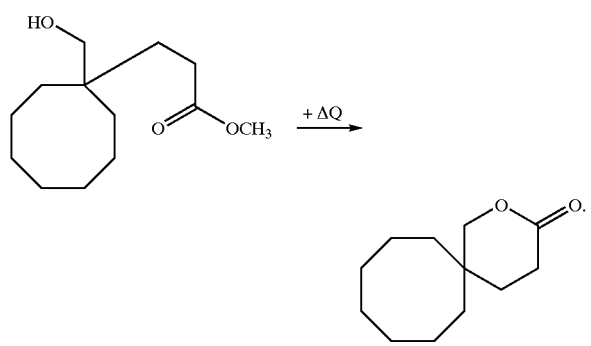

Into a 1 liter autoclave equipped with hydrogen line are placed 240 grams of the compound having the structure:

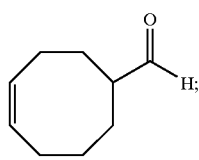

60 grams of anhydrous isopropyl alcohol; and 2.5 grams of Raney nickel.

The autoclave is sealed and pressurized to 400 psia with hydrogen. The contents of the autoclave are heated to 130° C. and maintained at 130° C. with a 400 psia pressurization with hydrogen for a period of 8 hours. The autoclave is cooled to room temperature and opened and the contents are filtered. The resulting material contains a minor quantity of the compound having the structure:

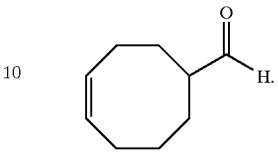

As a result, 8 grams of sodium borohydride are added to the material and the resulting mixture is heated to 80° C. for a period of 2 hours. The resulting product which is the compound having the structure:

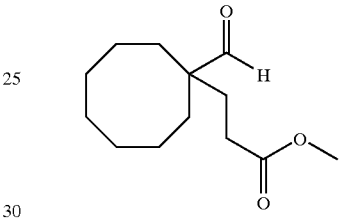

is then fractionally distilled, yielding the following fractions:

| Fraction No. | Vapor Temperature | Liquid Temperature | Vacuum mm/Hg | Reflux Ratio |
|---|---|---|---|---|
| 1 | 23/62 | 23/20 | 760/760 | 100% |
| 2 | 119 | 170 | 5 | 4:1 |
| 3 | 116 | 182 | 4 | 4:1 |
| 4 | 124 | 185 | 4 | 4:1 |
| 5 | 178 | 188 | 3 | 4:1 |
| 6 | 181 | 196 | 3 | 4:1 |
| 7 | 187 | 209 | 3 | 4:1 |
| 8 | 87 | 220 | 5 | 1:1 |

Bulked fractions 5–7 are the compound having the structure:

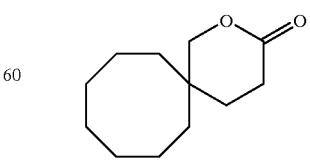

as confirmed by GLC, NMR, IR and mass spectral analyses.

EXAMPLE V

Preparation of 9-Methyl-2-oxaspiro[5.5]undecan-3-one

EXAMPLE V(A)

Reactions:

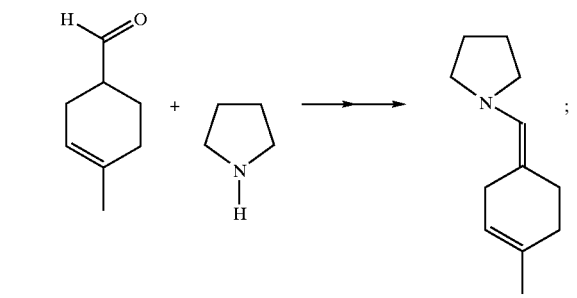

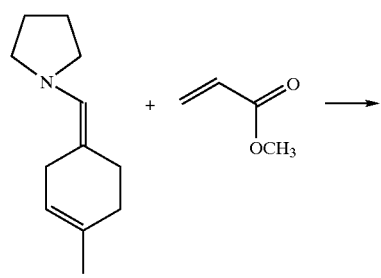

and

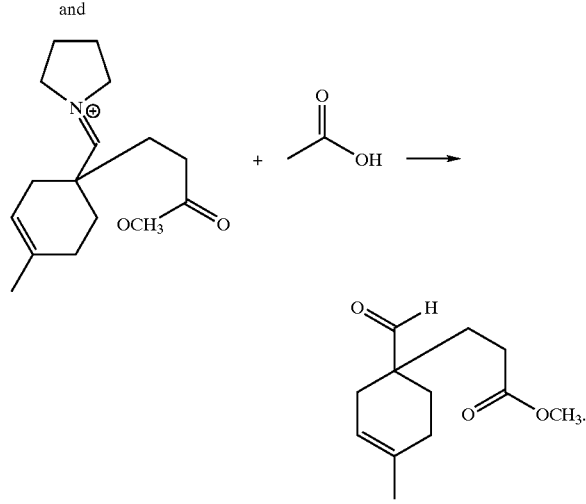

Into a 2 liter reaction vessel equipped with stirrer, thermometer, reflux condenser, heating mantle and Bidwell water recovery apparatus are placed 356 grams (3.6 moles) of cyclohexyl amine; 400 ml anhydrous toluene; and 435 grams (3.5 moles) of the compound having the structure:

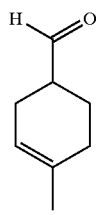

The resulting mixture is heated to reflux and maintained at reflux for a period of 2 hours at a temperature of 147° C. At the end of the 2 hour period, the reaction mass is cooled to 110° C., and over a period of 2 hours, while maintaining the reaction mass at 110–120° C., 400 grams (4.0 moles) of ethyl acrylate having the structure:

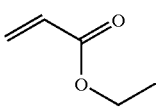

is fed into the reaction mass. The reaction mass is then heated for a period of 6 hours at a temperature of 120° C. At the end of the 6 hour period, the reaction mass is cooled to 35° C. and at admixed with one equal volume of 5% aqueous hydrochloric acid. The reaction mass is heated with stirring to 40° C. and maintained at 40° C. for a period of 2 hours. The resulting product is washed with one equal volume of distilled water, followed by one equal volume of a saturated aqueous solution of sodium bicarbonate.

The aqueous phase is separated from the organic phase, and the organic phase is dried over anhydrous magnesium sulfate. The resulting organic phase is then fractionally distilled yielding the following fractions:

| Fraction No. | Vapor Temperature | Liquid Temperature | Vacuum mm/Hg | Reflux Ratio |
|---|---|---|---|---|
| 1 | 23/37 | 40/100 | 200/80 | 100% |
| 2 | 47 | 115 | 10 | 100% |
| 3 | 134 | 155 | 0.7 | 100% |
| 4 | 140 | 160 | 0.6 | 100% |
| 5 | 138 | 180 | 0.6 | 100% |

NMR, IR, GLC and mass spectral analyses confirm that the distillation product has the structure:

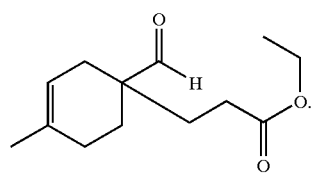

EXAMPLE V(B)

Reaction:

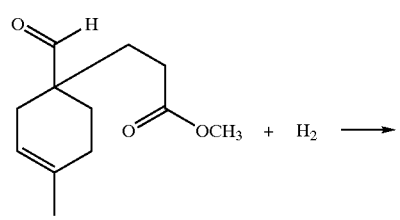

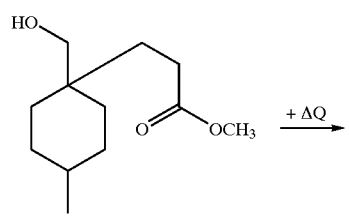

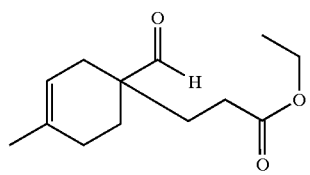

Into a 1 liter autoclave equipped with hydrogen feed line are placed 404 grams of the compound having the structure:

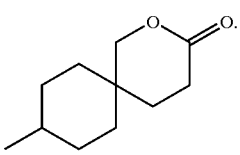

prepared according to Example V(A); 100 grams of anhydrous isopropyl alcohol; and 8 grams of Raney nickel. The autoclave is sealed and pressurized with hydrogen to 400 psia, and the temperature of the mixture within the autoclave is raised to 135° C. The pressure within the autoclave is maintained at 400 psia for a period of 6 hours, while maintaining the temperature therein at 135° C. At the end of the 6 hour period, the autoclave is cooled and opened, and the contents are filtered. The resulting liquid product is fractionally distilled yielding the following fractions:

| Fraction No. | Vapor Temperature | Liquid Temperature | Vacuum mm/Hg | Reflux Ratio |
| --- | --- | --- | --- | --- |
| 1 | 11 23/178 | 23/200 | 760/760 | 100% |
| 2 | 141 | 142 | 0.8 | 4:1 |
| 3 | 140 | 148 | 1 | 1:1 |
| 4 | 142 | 152 | 1 | 1.1 |
| 5 | 144 | 158 | 1 | 1:1 |
| 6 | 145 | 156 | 1 | 1:1 |
| 7 | 145 | 157 | 1 | 1:1 |
| 8 | 145 | 163 | 1.5 | 1:1 |
| 9 | 146 | 164 | 1.5 | 1:1 |
| 10 | 147 | 165 | 1.5 | 1:1 |
| 11 | 148 | 169 | 1.5 | 1:1 |
| 12 | 142 | 173 | 1 | 1:1 |
| 13 | 111 | 189 | 1 | 1:1 |

NMR, IR, GLC and mass spectral analyses yield the information that the resulting product has the structure:

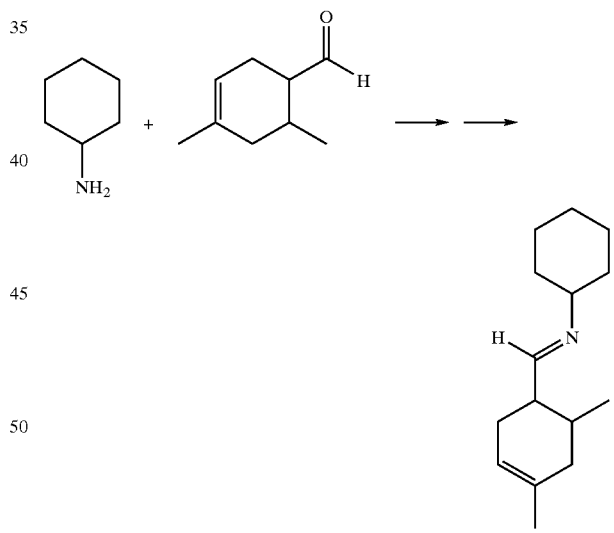

EXAMPLE VI

Preparation of 9,11-dimethyl-2-oxaspiro[5.5]undec-8-en-3-one

EXAMPLE VI(A)

Reactions:

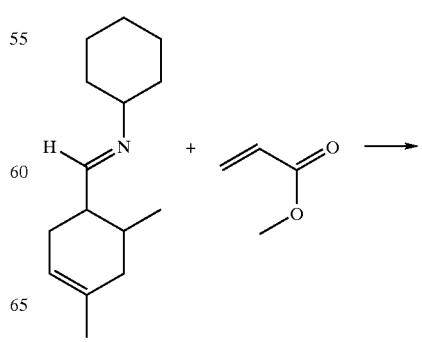

-continued and

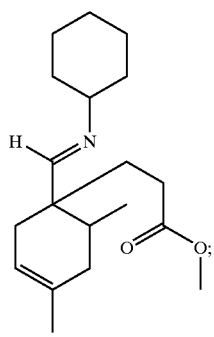

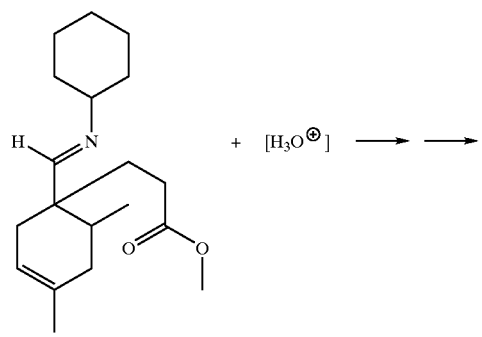 + [H₃O⊕] ⟶ ⟶

Into a 2 liter reaction vessel equipped with stirrer, thermometer, reflux condenser, heating mantle and Bidwell water recovery apparatus are placed 414 grams (3.0 moles) of the aldehyde having the structure:

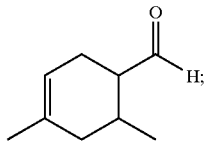

325 grams (3.3 moles) of cyclohexyl amine and 300 ml anhydrous toluene.

The reaction mixture is heated to reflux at 146° C. while removing water from the reaction via the Bidwell water recovery apparatus. The refluxing is continued for a period of 2 hours. At the end of the 2 hour period, the reaction mass is cooled to 110° C. Over a 2.5 hour period, 300 grams (3.5 moles) of methyl acrylate having the structure:

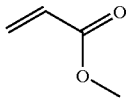

is added to the reaction mass. The reaction mass is then heated for a period of 6 hours at 110° C. with stirring. At the end of the 6 hour period, the reaction mass is cooled to 35° C. and an equal volume of 5% aqueous hydrochloric acid is added to the reaction mass. The reaction mass is then heated again to 110° C. and maintained with stirring at 110° C. for a period of 4 hours. At the end of the 4 hour period, the reaction mass is cooled to room temperature and washed consecutively with one equal volume of distilled water, followed by one equal volume of saturated aqueous sodium bicarbonate.

The organic phase is separated from the aqueous phase, and the organic phase is dried over anhydrous magnesium sulfate. The dried product is then fractionally distilled yielding the following fractions:

| Fraction No. | Vapor Temperature | Liquid Temperature | Vacuum mm/Hg | Reflux Ratio |
|---|---|---|---|---|
| 1 | 23/41 | 23/120 | 260/40 | 100% |
| 2 | 65 | 147 | 5 | 100% |
| 3 | 150 | 185 | 2 | 100% |
| 4 | 152 | 195 | 1 | 100% |

NMR, IR, GLC and mass spectral analyses confirm that the resulting product has the structure:

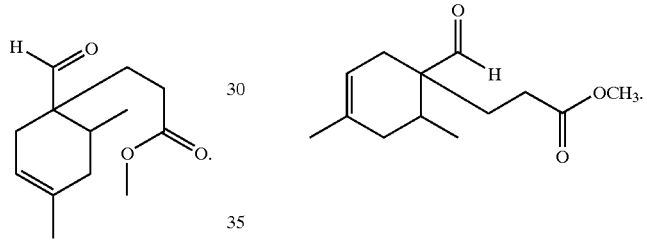

EXAMPLE VI(B)

Reactions:

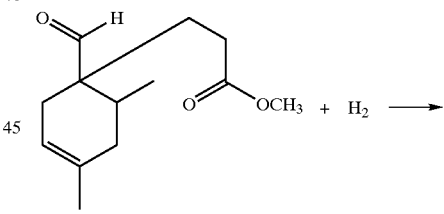 + H₂ ⟶

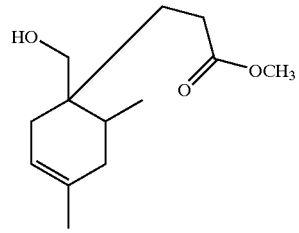

and

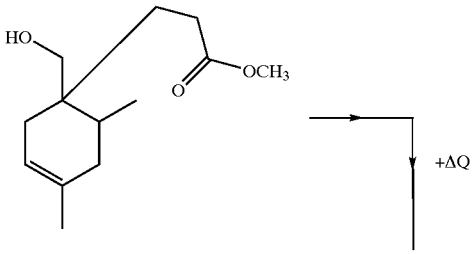

+ΔQ

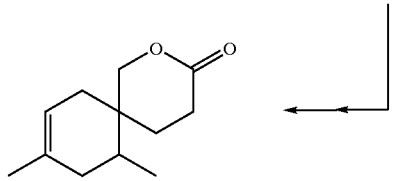

Into a 1 liter autoclave equipped with hydrogen feed line are placed 355 grams of the reaction product of Example VI(A) having the structure:

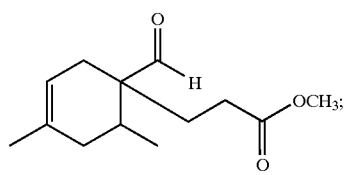

50 grams of anhydrous isopropyl alcohol; and 7.1 grams of a copper chromite catalyst, to wit: CuCr. The autoclave is sealed and hydrogenated to a pressure of 500 psia while raising the temperature of the contents of the autoclave to 155° C. The autoclave is maintained at a pressure of 440 psia over a period of 2.5 hours during pressurization with hydrogen, while the temperature thereof is maintained at 155° C. At the end of the 2.5 hour period, the autoclave is cooled to room temperature and opened. The contents of the autoclave are filtered and the isopropyl solvent is distilled up to 210° C. The resulting product is then fractionally distilled yielding the following fractions:

| Fraction No. | Vapor Temperature | Liquid Temperature | Vacuum mm/Hg | Reflux Ratio |
|---|---|---|---|---|
| 1 | 23/74 | 73/240 | 760/760 | 100% |
| 2 | 158 | 167 | 1 | 4:1 |
| 3 | 153 | 162 | 0.8 | 4:1 |
| 4 | 156 | 166 | 0.8 | 4:1 |
| 5 | 154 | 163 | 0.8 | 4:1 |
| 6 | 156 | 165 | 0.8 | 1:1 |
| 7 | 153 | 167 | 0.8 | 1:1 |
| 8 | 154 | 167 | 0.8 | 1:1 |
| 9 | 155 | 169 | 0.8 | 1:1 |
| 10 | 156 | 168 | 0.8 | 1:1 |
| 11 | 158 | 172 | 0.8 | 1:1 |
| 12 | 160 | 176 | 1 | 1:1 |
| 13 | 113 | 195 | 1 | 1:1 |

NMR, GLC, IR and mass spectral analyses yield the information that the resulting product has the structure:

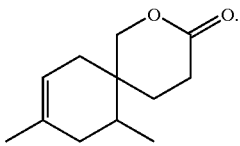

EXAMPLE VII

CHAMOMILE FORMULATIONS

The following chamomile formulations are prepared:

| Ingredients | Example VII(A) | Example VII(B) | Example VII(C) |
|---|---|---|---|
| Oil of chamomile | 12.0 | 12.0 | 12.0 |
| Citronellol | 4.0 | 4.0 | 4.0 |
| Geraniol | 4.0 | 4.0 | 4.0 |
| The compound having the structure: 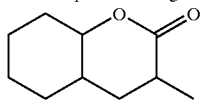 prepared according to Example I(B), bulked distillation fractions 7–9. | 24.0 | 0 | 0 |
| The compound having the structure: 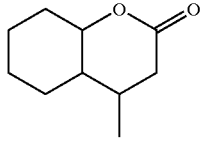 prepared according to Example II(B), bulked distillation fractions 4–9. | 0 | 24.0 | 0 |

-continued

| Ingredients | Example VII(A) | Example VII(B) | Example VII(C) |
|---|---|---|---|
| The compound having the structure: 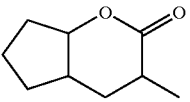 prepared according to Example III(B), bulked distillation fractions 4–12. | 0 | 0 | 24.0 |

The product of Example 1(B) imparts to this chamomile aroma intense and substantive jasmine, floral, coumarinic, fruity, nutty and hay-like undertones with cooling nuances. Accordingly, the perfume composition of Example VII(A) can be described as "a chamomile aroma with jasmine, floral, coumarinic, fruity, nutty and hay-like undertones with cooling nuances."

The product of Example VII(B) has an excellent chamomile aroma with intense and substantive sweet, coumarinic, tonka, tobacco and lactonic undertones with nutty and hay-like topnotes. Accordingly, the perfume composition of Example VII(B) can be described as "a chamomile aroma with sweet, coumarinic, tonka, tobacco and lactonic undertones with nutty and hay-like topnotes."

The product of Example VII(C) has an excellent chamomile aroma with intense and substantive nutty, lactonic, green, tagette and coumarinic undertones with "cooling" nuances. Accordingly, the perfume composition of Example VII(C) can be described as "a chamomile aroma with nutty, lactonic, green, tagette and coumarinic undertones with cooling nuances."

EXAMPLE VIII

CHAMOMILE FORMULATIONS

The following chamomile formulations are prepared:

| Ingredients | Example VIII(A) | Example VIII(B) | Example VIII(C) |
|---|---|---|---|
| Oil of chamomile | 12.0 | 12.0 | 12.0 |
| Citronellol | 4.0 | 4.0 | 4.0 |
| Geraniol | 4.0 | 4.0 | 4.0 |
| The compound having the structure: 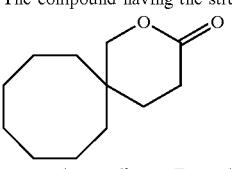 prepared according to Example IV(B), bulked distillation fractions 5–7. | 24.0 | 0 | 0 |
| The compound having the structure: 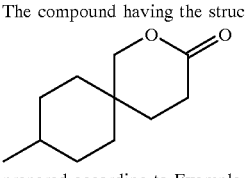 prepared according to Example V(B), bulked distillation fractions 4–10. | 0 | 24.0 | 0 |
| The compound having the structure: 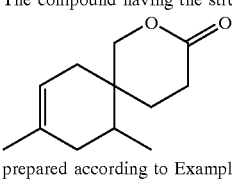 prepared according to Example VI(B), bulked distillation fractions 4–10. | 0 | 0 | 24.0 |

The product of Example VIII(B) has an excellent chamomile aroma with intense and substantive lactonic, woody, earthy, ambery and green undertones. Accordingly, the perfume composition of Example VIII(A) can be described as "a chamomile aroma with lactonic, woody, earthy, ambery and green undertones."

The product of Example VIII(B) has an excellent chamomile aroma with intense and substantive woody, orris, coconut and coumarinic undertones with orris, woody and coumarinic topnotes. Accordingly, the perfume composition of Example VIII(B) can be described as "a chamomile aroma with woody, orris, coconut and coumarinic undertones with orris, woody and coumarinic topnotes."

The product of Example VIII(C) has an excellent chamomile aroma with intense and substantive lactonic, spicy and cinnamon undertones. Accordingly, the perfume composition of Example VIII(C) can be described as "a chamomile aroma with lactonic, spicy and cinnamon undertones."

EXAMPLE IX

COSMETIC POWDER PREPARATIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Perfumery Substance | Perfumery Nuance |
|---|---|
| The compound having the structure:<br />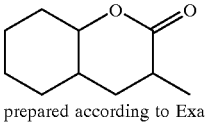<br />prepared according to Example I(B), bulked distillation fractions 7–9 | A fruity, nutty, hay-like and coumarmic aroma with "cooling" nuances and with jasmine and floral undertones. |
| The compound having the structure:<br />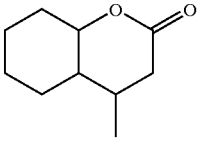<br />prepared according to Example II(B), bulked distillation fractions 4–9. | A sweet, coumarinic, tonka, tobacco and lactonic aroma with nutty and hay-like topnotes. |
| The compound having the structure:<br />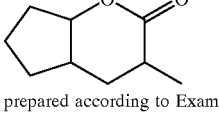<br />prepared according to Example III(B), bulked distillation fractions 4–12. | A green, tagette, coumarinic aroma with "cooling" nuances and nutty, lactonic undertones. |
| The compound having the structure:<br />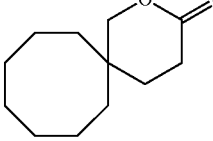<br />prepared according to Example IV(B), bulked distillation fractions 5–7. | A woody, earthy, ambery, green aroma with lactonic and woody undertones. |
| The compound having the structure:<br />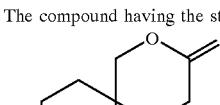<br />prepared according to Example V(B), bulked distillation fractions 4–10. | A woody, orris, coconut, coumarinic aroma with orris, woody and coumarinic topnotes. |
| The compound having the structure:<br />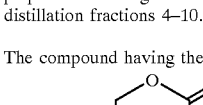<br />prepared according to Example VI(B), bulked distillation fractions 4–10. | Lactonic, spicy, cinnamon aroma with lactonic, spicy and cinnamon undertones. |

TABLE II-continued

| Perfumery Substance | Perfumery Nuance |
|---|---|
| The perfume composition of Example VII(A). | A chamomile aroma with jasmine, floral, coumarinic, fruity, nutty and hay-like undertones with cooling nuances. |
| The perfume composition of Example VII(B). | A chamomile aroma with sweet, coumarinic, tonka, tobacco and lactonic undertones with nutty and hay-like topnotes. |
| The perfume composition of Example VII(C). | A chamomile aroma with nutty, lactonic, green, tagette and coumannic undertones with cooling nuances. |
| The perfume composition of Example VIII(A). | A chamomile aroma with lactonic, woody, earthy, ambery and green undertones. |
| The perfume composition of Example VIII(B). | A chamomile aroma with woody, orris, coconut and coumarmnic undertones with orris, woody and coumannic topnotes. |
| The perfume composition of Example VIII(C). | A chamomile aroma with lactonic, spicy and cinnamon undertones. |

EXAMPLE X

Perfumed Liquid Detergent

Concentrated liquid detergents (lysine salt of n-dodecylbenzene sulfonic acid as more specifically described in U.S. Pat. No. 3,948,818 issued on Apr. 6, 1976, the specification for which is incorporated by reference herein) with aromas as set forth in Table II of Example IX, supra, are prepared containing 0.10%, 0.15%, 0.20%, 0.25%, 0.30% and 0.35% of each of the substances of Table II of Example IX. They are prepared by adding and homogeneously admixing the appropriate quantity of one of the substances of Table II of Example IX in the liquid detergent. The detergents all possess excellent aromas as set forth in Table II of Example IX, supra, the intensity increasing with greater concentrations of substance as set forth in Table II of Example IX, supra.

EXAMPLE XI

PREPARATION OF COLOGNES AND HANDKERCHIEF PERFUMES

The substances set forth in Table II of Example IX are incorporated separately into colognes at concentrations of 2.0%, 2.5%, 3.0%, 3.5%, 4.0%, 4.5% and 5.0% in 80%, 85%, 90% and 95% aqueous food grade ethanol solutions and into handkerchief perfumes at concentrations of 15%, 20%, 25% and 30% in 80%, 85%, 90% and 95% aqueous food grade ethanol solutions. Distinctive aromas as set forth in Table II of Example IX, supra, are imparted to the colognes and to the handkerchief perfume compositions at all levels indicated.

EXAMPLE XII

PREPARATION OF SOAP COMPOSITION

100 Grams of soap chips (per sample) (IVORY®, produced by the Procter & Gamble Company of Cincinnati, Ohio) are each mixed with 1 gram samples substances as set forth in Table II of Example IX, supra, until homogeneous compositions are obtained. In each of the cases, the homogeneous compositions are heated under 8 atmospheres pressure at 180° C. for a period of 3 hours and the resulting liquid samples are placed in soap molds. The resulting soap cakes, on cooling, manifest aromas as set forth in Table II of Example IX.

EXAMPLE XIII

PREPARATION OF SOLID DETERGENT COMPOSITIONS

Detergents are prepared from the following ingredients according to Example I of Canadian Letters Patent No. 1,007,948, the specification for which is incorporated by reference herein:

| Ingredients | Parts by Weight |
|---|---|
| NEODOL ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, brighteners | q.s. |

This detergent is a phosphate-free detergent. Samples of 100 grams each of this detergent are admixed with 0.10, 0.15, 0.20 and 0.25 grams of each of the substances of Table II of Example IX, supra. Each of the detergent samples has an excellent aroma as set forth in Table II of Example IX.

EXAMPLE XIV

DRYER-ADDED FABRIC SOFTENER ARTICLE

Utilizing the procedure of Example I at column 15 of U.S. Pat. No. 3,632,396, the specification for which is incorporated by reference herein, non-woven cloth substrates useful as dryer-added fabric softening articles of manufacture are prepared wherein the substrate, the substrate coating, the outer coating and the perfuming material are as follows:

1. a water "dissolvable" paper ("Dissolvo Paper");
2. Adogen 448 (m.p. about 140° F.) as the substrate coating; and
3. an outer coating having the following formulation:
    57%—$C_{20}$–$C_{22}$ HAPS;
    22%—isopropyl alcohol;
    20%—antistatic agent; and
    1%—of one of the substances of Table II of Example XI, supra.

Fabric softening compositions prepared according to Example I at column 15 of U.S. Pat. No. 3,632,396, having aroma characteristics as set forth in of Table II of Example IX, supra, consist of a substrate coating having a weight of about 3 grams per 100 square inches of substrate; a first coating located directly on the substrate coating consisting of about 1.85 grams per 100 square inches of substrate; and a outer coating coated on the first coating consisting of about 1.4 grams per 100 square inches of substrate. One of the substances of Table II of Example IX, supra, is admixed in each case, with the outer coating mixture, thereby providing a total aromatized outer coating weight ratio to substrate of about 0.5:1 by weight of the substrate. The aroma characteristics are imparted in a pleasant manner to the headspace in a dryer on operation thereof in each case using said dryer-added fabric softener non-woven fabrics, and these aroma characteristics are described in Table II of Example IX, supra.

EXAMPLE XV

HAIR SPRAY FORMULATIONS

The following hair spray formulation is prepared by first dissolving PVP/VA E-735 copolymer, manufactured by the GAF Corporation of 140 West $51^{st}$ Street, New York, N.Y., in 91.62 grams of 95% food grade ethanol. 8.0 Grams of the polymer are dissolved in the alcohol. The following ingredients are added to the PVP/VA alcoholic solution:

| Ingredients | Weight Percent |
| --- | --- |
| Dioctyl substrate | 0.05 |
| Benzyl alcohol | 0.10 |
| Dow Corning 473 fluid (prepared by the Dow Corning Corporation) | 0.10 |
| TWEEN ® 20 surfactant (prepared by the ICI America Corporation) | 0.03 |
| One of the perfumery substances as set forth in Table II of Example IX, supra. | 0.10 |

The perfume substances as set forth in Table II of Example IX, supra, add aroma characteristics as set forth in Table II of Example IX, supra, which are rather intense and aesthetically pleasing to the users of the soft-feel, good-hold pump hair sprays.

EXAMPLE XVI

CONDITIONING SHAMPOOS

Monoamid CMA (prepared by the Mona Industries Company) (3.0 weight percent) is melted with 2.0 weight percent coconut fatty acid (prepared by the Procter & Gamble Company of Cincinnati, Ohio); 1.0 weight percent ethylene glycol distearate (prepared by the Armak Corporation); and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is COMPOSITION A.

GAFQUAT® 755N polymer (manufactured by GAF Corporation of 140 West $51^{st}$ Street, New York, N.Y.) (5.0 weight percent) is admixed with 0.1 weight percent sodium sulfite and 1.4 weight percent polyethylene glycol 6000 distearate produced by Armak Corporation. This material is COMPOSITION B.

The resulting COMPOSITION A and COMPOSITION B are then mixed in a 50:50 weight ratio of A:B and cooled to 45° C., and 0.3 weight percent of a perfuming substance as set forth in Table II of Example IX, supra, is added to the mixture. The resulting mixture is cooled to 40° C., and blending is carried out for an additional one hour in each case. At the end of this blending period, the resulting material has a pleasant fragrance as indicated in Table II of Example IX, supra.

EXAMPLE XVII

Each of the fragrance materials of Table II of Example IX, supra, are added to a 50:50 weight:weight mixture of low density polyethylene:polyepsilon caprolactone PCL-700 forming scented pellets with scents as set forth in Table II of Example IX, supra.

Using the apparatus of U.S. Pat. No. 3,505,432 issued on Apr. 7, 1970 (the specification for which is incorporated by reference herein), 75 lbs. of a 50:50 mixture of PCL-700 polyepsilon caprolactone (manufactured by the Union Carbide Corporation of New York, N.Y.), having a melting point of about 180–190° F.:low-density polyethylene, are heated to about 250° F. 25 Lbs. of each of the fragrance materials as set forth in Table II of Example IX is then quickly added to the liquefied polymer mixture. The temperature is then raised to about 250° F., and the mixing is effected for 5–15 minutes. The molten polymer enriched with perfume ingredients is then formed into polymer beads or pellets having pronounced scents as described in Table II of Example IX. Analysis demonstrates that the pellets contain about 25% of the perfume material so that almost no losses in the scenting substance did occur. These pellets may be called "master pellets."

50 Lbs. of each batch of the scent containing "master pellets" are then added to 1,000 lbs. of unscented polypropylene, and the mass is heated to the liquid state. The liquid is molded into thin sheets of films. The thin sheets of films have pronounced aromas as set forth in Table II of Example IX, supra. The sheets of films are cut into strips of 0.25 inches in width×3 inches in length and placed into room air fresheners.

On operation of the room air fresheners after 4 minutes, the room in each case has an aesthetically pleasing aroma with no foul odor being present,the aroma being described in Table II of Example IX, supra.

What is claimed is:

1. A process for augmenting, enhancing or imparting an aroma in or to a consumable material selected from the group consisting of perfume compositions, perfumed articles, colognes and perfume polymers, comprising the step of intimately admixing with a consumable material base an aroma augmenting, enhancing or imparting quantity and concentration of bicyclic lactone having the structure:

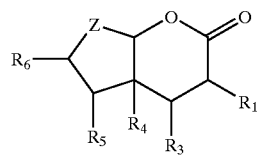

wherein Z is the moiety:

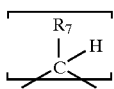

and wherein one of $R_1$ or $R_3$ is methyl and the other is hydrogen; wherein $R_4$, $R_5$, $R_6$, and $R_7$ are hydrogen or nonadjacent $C_1$–$C_3$ alkyl;

and completes a $C_5$ cycloalkyl, cycloalkadienyl or cycloalkenyl ring moiety.

2. The process of claim 1 wherein the bicyclic lactone has the structure:

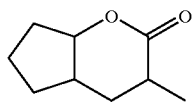

3. The process of claim 1 wherein the consumable material is a detergent composition or a fabric softener composition.

4. The process of claim 2 wherein the consumable material is a detergent composition or a fabric softener composition.

5. A perfumed article comprising a perfumed article base and an aroma augmenting, enhancing or imparting quantity and concentration of a bicyclic lactone having the structure:

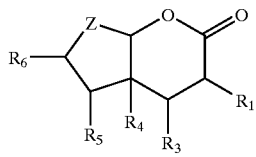

wherein Z is the moiety:

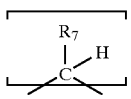

and wherein one of $R_1$ or $R_3$ is methyl and the other is hydrogen; wherein $R_4$, $R_5$, $R_6$, and $R_7$ are hydrogen or nonadjacent $C_1$–$C_3$ alkyl;

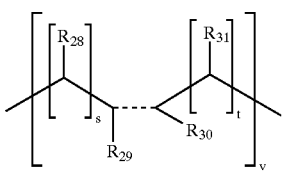

and completes a $C_5$ cycloalkyl, cycloalkadienyl or cycloalkenyl ring moiety.

6. A perfume composition comprising a perfume base and intimately admixed therewith an aroma augmenting, enhancing or imparting quantity of a bicyclic lactone having the structure:

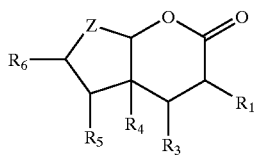

wherein Z is the moiety:

and wherein one of $R_1$ or $R_3$ is methyl and the other is hydrogen; wherein $R_4$, $R_5$, $R_6$, and $R_7$ are hydrogen or nonadjacent $C_1$–$C_3$ alkyl;

and completes a $C_5$ cycloalkyl, cycloalkadienyl or cycloalkenyl ring moiety.

7. A bicyclic lactone having the structure:

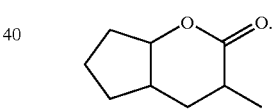

* * * * *